US010645938B2

(12) United States Patent
Riley

(10) Patent No.: US 10,645,938 B2
(45) Date of Patent: May 12, 2020

(54) ENDOPHYTE COMPOSITIONS AND THE METHODS FOR IMPROVEMENT OF PLANT TRAITS

(71) Applicant: Indigo Ag, Inc., Boston, MA (US)

(72) Inventor: Raymond Riley, Woodbury, MN (US)

(73) Assignee: Indigo Ag, Inc., Boston, MA (US)

( * ) Notice: Subject to any disclaimer, the term of this patent is extended or adjusted under 35 U.S.C. 154(b) by 0 days.

(21) Appl. No.: 15/829,844

(22) Filed: Dec. 1, 2017

(65) Prior Publication Data

US 2018/0249716 A1   Sep. 6, 2018

Related U.S. Application Data

(60) Provisional application No. 62/465,818, filed on Mar. 1, 2017, provisional application No. 62/466,250, filed on Mar. 2, 2017, provisional application No. 62/467,734, filed on Mar. 6, 2017, provisional application No. 62/465,833, filed on Mar. 2, 2017, provisional application No. 62/465,820, filed on Mar. 2, 2017, provisional application No. 62/467,737, filed on Mar. 6, 2017, provisional application No. 62/551,724, filed on Aug. 29, 2017.

(51) Int. Cl.

| | |
|---|---|
| A01N 63/04 | (2006.01) |
| C12N 1/14 | (2006.01) |
| A01N 63/00 | (2020.01) |
| A01H 17/00 | (2006.01) |
| C12N 15/82 | (2006.01) |
| A01H 3/00 | (2006.01) |
| A01H 5/02 | (2018.01) |
| A01H 5/04 | (2018.01) |
| A01H 5/10 | (2018.01) |
| A01C 1/06 | (2006.01) |
| A01H 5/06 | (2018.01) |
| C12Q 1/6895 | (2018.01) |
| C12Q 1/689 | (2018.01) |
| C12R 1/01 | (2006.01) |
| C12N 1/20 | (2006.01) |
| C12R 1/66 | (2006.01) |
| C12R 1/645 | (2006.01) |

(52) U.S. Cl.
CPC ............... *A01N 63/04* (2013.01); *A01C 1/06* (2013.01); *A01H 3/00* (2013.01); *A01H 5/02* (2013.01); *A01H 5/04* (2013.01); *A01H 5/06* (2013.01); *A01H 5/10* (2013.01); *A01H 17/00* (2013.01); *A01N 63/00* (2013.01); *C12N 1/14* (2013.01); *C12N 1/20* (2013.01); *C12N 15/8261* (2013.01); *C12Q 1/689* (2013.01); *C12Q 1/6895* (2013.01); *C12R 1/01* (2013.01); *C12R 1/645* (2013.01); *C12R 1/66* (2013.01)

(58) Field of Classification Search
None
See application file for complete search history.

(56) References Cited

U.S. PATENT DOCUMENTS

| | | | |
|---|---|---|---|
| 2,200,532 | A | 5/1940 | Sherman |
| 4,940,834 | A | 7/1990 | Hurley et al. |
| 5,041,290 | A | 8/1991 | Gindrat et al. |
| 5,113,619 | A | 5/1992 | Leps et al. |
| 5,229,291 | A | 7/1993 | Nielsen et al. |
| 5,292,507 | A | 3/1994 | Charley |
| 5,415,672 | A | 5/1995 | Fahey et al. |
| 5,730,973 | A | 3/1998 | Morales et al. |
| 5,919,447 | A | 7/1999 | Marrone et al. |
| 5,994,117 | A | 11/1999 | Bacon et al. |
| 6,072,107 | A | 6/2000 | Latch et al. |
| 6,077,505 | A | 6/2000 | Parke et al. |
| 6,337,431 | B1 | 1/2002 | Tricoli et al. |
| 6,495,133 | B1 | 12/2002 | Xue |
| 6,602,500 | B1 | 8/2003 | Kharbanda et al. |
| 6,681,186 | B1 | 1/2004 | Denisov et al. |
| 6,689,880 | B2 | 2/2004 | Chen et al. |
| 6,823,623 | B2 | 11/2004 | Minato et al. |
| 7,037,879 | B2 | 5/2006 | Imada et al. |
| 7,084,331 | B2 | 8/2006 | Isawa et al. |
| 7,335,816 | B2 | 2/2008 | Kraus et al. |
| 7,341,868 | B2 | 3/2008 | Chopade et al. |
| 7,485,451 | B2 | 2/2009 | VanderGheynst et al. |
| 7,555,990 | B2 | 7/2009 | Beaujot |
| 7,632,985 | B2 | 12/2009 | Malven et al. |
| 7,763,420 | B2 | 7/2010 | Stritzker et al. |
| 7,906,313 | B2 | 3/2011 | Henson et al. |
| 7,977,550 | B2 | 7/2011 | West et al. |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Search of Agricultural Research Service Culture Collection (NRRL) for NRRL-67466, conducted on Jun. 20, 2019, 2 pages. (Year: 2019).*

(Continued)

*Primary Examiner* — Channing S Mahatan
(74) *Attorney, Agent, or Firm* — Goodwin Procter LLP

(57) ABSTRACT

This invention relates to methods and materials for modulating the characteristics of a plant, said plant having been heterologously disposed to an endophyte or a plurality of endophytes, or derived from a plant reproductive element heterologously disposed to an endophyte or a plurality of endophytes.

15 Claims, 2 Drawing Sheets

Specification includes a Sequence Listing.

(56) References Cited

U.S. PATENT DOCUMENTS

| | | | |
|---|---|---|---|
| 8,143,045 B2 | 3/2012 | Miansnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | Von Maltzahn et al. |
| 10,076,120 B2 | 9/2018 | von Maltzahn et al. |
| 10,104,862 B2 | 10/2018 | Vujanovic et al. |
| 2005/0072047 A1 | 4/2005 | Conkling et al. |
| 2006/0046246 A1 | 3/2006 | Zeng et al. |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2010/0064392 A1 | 3/2010 | Yang et al. |
| 2010/0095396 A1 | 4/2010 | Voeste et al. |
| 2010/0205690 A1 | 8/2010 | Biasing et al. |
| 2010/0227357 A1 | 9/2010 | Redman et al. |
| 2011/0182862 A1 | 7/2011 | Green et al. |
| 2012/0108431 A1 | 5/2012 | Williams et al. |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | Von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | von Maltzahn et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0153174 A1* | 6/2018 | Riley ............... A01H 3/00 |
| 2018/0177196 A1 | 6/2018 | Sword |
| 2018/0213800 A1 | 8/2018 | Djonovic et al. |
| 2018/0251776 A1 | 9/2018 | Riley |
| 2019/0133136 A1* | 5/2019 | Comby ............. A01N 63/00 |

FOREIGN PATENT DOCUMENTS

| | | |
|---|---|---|
| CA | 2562175 | 1/2013 |
| CN | 1604732 | 4/2005 |
| CN | 101311262 A | 11/2008 |
| CN | 101423810 A | 5/2009 |
| CN | 101570738 | 11/2009 |
| CN | 101693881 A | 4/2010 |
| CN | 102168022 A | 8/2011 |
| CN | 102352327 A | 2/2012 |
| CN | 102010835 B | 4/2012 |
| CN | 102533601 B | 10/2013 |
| CN | 103642725 A | 3/2014 |
| CN | 104560742 A | 1/2015 |
| CN | 104388356 A | 3/2015 |
| EP | 0192342 | 8/1986 |
| EP | 0223662 | 5/1987 |
| EP | 0378000 | 7/1990 |
| EP | 0494802 | 7/1992 |
| EP | 0818135 | 1/1998 |
| EP | 1621632 | 2/2006 |
| EP | 1935245 | 6/2008 |
| EP | 2676536 | 12/2013 |
| JP | 2009/072168 | 4/2009 |
| KR | 20100114806 A | 10/2010 |
| KR | 101091151 | 12/2011 |
| KR | 20130023491 | 12/2011 |
| WO | WO 1988/009114 | 1/1988 |
| WO | WO 1994/016076 | 7/1994 |
| WO | WO 2000/029607 | 5/2000 |
| WO | WO 2001/083697 | 11/2001 |
| WO | WO 2001/083818 | 11/2001 |
| WO | WO 2002/065836 | 8/2002 |
| WO | WO 2004/046357 | 6/2004 |
| WO | WO 2005/003328 | 1/2005 |
| WO | WO 2007/021200 | 2/2007 |
| WO | WO 2007/107000 | 9/2007 |
| WO | WO 2008/103422 | 8/2008 |
| WO | WO 2009/012480 A2 | 1/2009 |
| WO | WO 2009/078710 A1 | 6/2009 |
| WO | WO 2009/126473 A1 | 10/2009 |
| WO | WO 2010/109436 | 9/2010 |
| WO | WO 2010/115156 | 10/2010 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | WO 2012/034996 | 3/2012 |
| WO | WO 2013/016361 | 1/2013 |
| WO | WO 2013/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |
| WO | WO 2014/121366 | 8/2014 |
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |

(56) References Cited

FOREIGN PATENT DOCUMENTS

| WO | WO 2015/192172 | 12/2015 |
|---|---|---|
| WO | WO 2015/200852 | 12/2015 |
| WO | WO 2015/200902 | 12/2015 |
| WO | WO 2016/090212 | 6/2016 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |
| WO | WO 2016/057991 | 3/2019 |

OTHER PUBLICATIONS

Sequence Alignment of Seq ID No. 32 with Seq ID No. 38 of USPGUB 20180153174. Search conducted on Jun. 11, 2019, 3 pages. (Year: 2019).*
Sequence Alignment of Seq ID No. 33 with Seq ID No. 39 of USPGPUB 20180153174, Search conducted on Jun. 2019, 3 pages. (Year: 2019).*
NCBI, GenBank No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Langille, M.G.I. et al., "Predictive functional profiling of microbial communities using 16S rRNA marker gene sequences," Nature Biotechnology, 2013, vol. 31, No. 9, pp. 814-821.
Li, W. et al., "Ultrafast clustering algorithms for metagenomic sequence analysis," Briefings in Bioinformatics, Nov. 1, 2012, vol. 13, No. 6., pp. 656-668.
Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.
Artursson, V., et al., "Interactions between *arbuscular mycorrhizal* fungi and bacteria and their potential for stimulating plant growth", Environmental Microbiology, vol. 8, No. 1, Jan. 1, 2006, pp. 1-10.
Azcon, R., et al., "Selective interactions between different species of mycorrhizal fungi and *Rhizobium meliloti* strains, and their effects on growth, N2-fixation (15N) and nutrition of *Medicago sativa* L.," New PhytoL., 1991, vol. 117, pp. 399-404.
Bing, LA, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.
Compant, S., et al., "Endophytic colonization of *Vitis vinfera* L. by *Burkholderia phytofirmans* strain PsJN: from the rhizosphere to inflorescence tissues," FEMS Microbiol Ecol, 2008, pp. 84-93, vol. 63.
NCBI GenBank: Accession No. JX880250.1, "*Enterobacteriaceae bacterium* Clero1 16S ribosomal RNA gene, partial sequence," NIH, Jun. 24, 2015, 2 Pages, can be retreived at <URL:https://www.ncbi.nlm.nih.gov/nucleotide/JX880250.1?report=genbank&log$=nuclalign&blast_rank=80&RID=KWUPBV08015>.
NCBI, GenBank Accession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at <URL:https://www.ncbi.nlm.nih.gov/nuccore/KX641980>.
Database EMBL [Online] Oct. 1, 2001, 2 Pages, "*Setosphaeria monoceras* 28S ribosomal RNA gene, partial sequence," XP002777918, retrieved from EBI accession No. EM_STD:AY016368 Database accession No. AY016368 sequence.
Fox, G., et al., "How close is close: 16S rRNA sequence identity may not be sufficient to guarantee species identity." International Journal of Systematic and Evolutionary Microbiology 42.1, 1992, pp. 166-170.
Hubbard, M., et al., 2011. "Agricultural Potential of Fungal Endophytes of Grasses, Cereals and Wheat," in: Wheat: Genetics, Crops and Food Production. Nova Science Publishers Hauppauge, NY, USA. pp. 333-345.

Impullitti, A.E., et al., "Fungal endophyte diversity in soybean", Journal of Applied Microbiolog, vol. 114, No. 5, May 1, 2013, pp. 1500-1506.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Nassar, A., et al., "Promotion of plant growth by an auxin-producing isolate of the yeast Williopsis saturnus endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Sarkar, S., et al., "New report of additional enterobacterial species causing wilt in West Bengal, India," Canadian Journal of Microbiology, 2015, vol. 61, No. 7, pp. 477-486.
Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.
Zhang, Y., et al., BcGsl, a glycoprotein from Botrytis cinerea, elicits defence response and improves disease resistance in host plants. Biochemical and biophysical research communications, Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2014/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.

(56) References Cited

OTHER PUBLICATIONS

PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT Invitation to Pay Additional Fees, PCT Application No. PCT/US2017/064292, dated Mar. 5, 2018, 15 Pages.
PCT International Search Report and Written Opinion, PCT Application No. PCT/USS2017/068255, dated Mar. 19, 2018, 14 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,916,678, dated Feb. 8, 2017, 8 Pages.
Canadian Patent Office, Office Action, Canadian Patent Application No. 2,935,218, dated Jun. 13, 2017, 5 Pages.
Canadian Patent Office, Office Action, Canadian Patent Application No. 2,935,218, dated May 8, 2018, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).
Chinese Patent Office, 2nd Office Action for Chinese Patent Application No. CN 201480072142.7, dated Oct. 30, 2017, 13 Pages, (with English translation).
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report for European Patent Application No. 15810847.2, dated Feb. 28, 2018, 19 Pages.
European Patent Office, Supplementary European Search Report, European Patent Application No. EP 15812324.0, dated Nov. 2, 2017, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
Intellectual Property Australia, Examination Report for Australian Patent Application No. 2016202480, dated Apr. 28, 2016, 2 Pages.
Intellectual Property Australia, Examination Report for Australian Patent Application No. 2014346664, dated Nov. 24, 2016, 3 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
Intellectual Property Australia, Examination Report No. 1 for Australian Patent Application No. AU 2017201009, dated Apr. 4, 2018, 3 Pages.
Intellectual Property Australia, Examination Report No. 1 for Australian Patent Application No. AU 2017210482, dated May 15, 2018, 4 Pages.
New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 715728, dated Dec. 5, 2016, 3 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, Further Examination Report, New Zealand Patent Application No. 726116, dated Feb. 27, 2018, 6 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Ukraine Patent Office, Office Action for Ukrainian Patent Application No. a201508515, dated May 19, 2017, 14 Pages (with English translation).
Ukraine Patent Office, Office Action for Ukrainian Patent Application No. a201508515, dated Feb. 20, 2018, 9 Pages (with English translation).
Office Action for Israel Patent Application No. IL 255682, dated Mar. 15, 2018, 2 Pages (Translation).
Office Action for Israel Patent Application No. IL255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).

(56) References Cited

OTHER PUBLICATIONS

Office Action for Israel Patent Application No. IL 245385, dated Mar. 23, 2018, 3 Pages (With Concise Explanation of Relevance).
Abarenkov, K., et al., "PlutoF-A Web Based Workbench for Ecological and Taxonomic Research, with an Online Implementation for Fungal ITS Sequences," Evol Bioinform Online, 2010, pp. 189-196, vol. 6.
Abarenkov, K., et al., "The Unite Database for Molecular Identification of Fungi—Recent Updates and Future Perspectives," New Phytol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdellatif, L., et al., "Characterization of virulence and PCR-DGGE profiles of *Fusarium avenaceum* from western Canadian Prairie Ecozone of Saskatchewan,"Canadian Journal of Plant Pathology, 2010, pp. 468-480.
Abdou, R., et al., "Botryorhodines A-D, antifungal and cytotoxic depsidones from *Botryosphaeria rhodina*, an endophyte of the medicinal plant *Bidens pilosa*," Phytochemistry, 2010, vol. 71, pp. 110-116.
Abou-Shanab, R. A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Adhikari, M., et al., "A New Record of *Pseudeurotium bakeri* from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promoting Activities," Microbiol Res., 2008, pp. 173-181, vol. 163.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
Amann, R., et al., "The Identification of Microorganisms by Fluorescence in Situ Hybridisation," Curr Opin Biotechnol., 2001, pp. 231-236, vol. 12.
Amatuzzi, R.F., et al., "Universldade Federal Do Parana," Jan. 1, 2014, 52 Pages. (With English Abstract).
Amatuzzi, R.F., et al., "Potential of endophytic fungi as biocontrol agents of *Duponchelia fovealis* (Zeller) (Lepidoptera:Crambidae)," Brazilian Journal of Biology, Nov. 9, 2017, 7 Pages.
Apel, K., et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar *Ascomycota* and in vitro establishment of their symbiotic associations," Appl. Environ. Microbiol., 2016, pp. 2943-2949, vol. 82, No. 10.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Aveskamp, M., et al., "DNA phylogeny reveals polyphyly of Phoma section Peyronellaea and multiple taxonomic novelties," Mycologia, 2009, vol. 101, No. 3, pp. 363-382.
Bacon, C. W., et al., "Isolation, in Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev Phytopathol., 1966, pp. 311-334,vol. 4.
Baltruschat, H., et al., "Salt tolerance of barley induced by the root endophyte *Piriformospora indica* is associated with a strong increase in antioxidants," New Phytologist., 2008, pp. 501-510, vol. 180.
Bensch, K., et al., "Species and ecological diversity within the *Cladosporium cladosporioides* complex (Davidiellaceae, Capnodiales)," Studies in Mycology, 2010, pp. 1-94, vol. 67.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
Block, C. C., et al., "Seed Transmission of *Pantoea stewartii* in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005.
Bulgarelli, D., et al., "Structure and Functions of the Bacterial Microbiota of Plants," Annu Rev Plant Biol., 2013, pp. 807-838, vol. 64.
Buttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbial Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," Power Point Presentation dated Mar. 23, 2013.
Castillo, D., et al., "Fungal Endophytes: Plant Protective Agents Against Herbivores," Power Point Presentation dated Aug. 4, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chagas, F., et al., "A Mixed Culture of Endophytic Fungi Increases Production of Antifungal Polyketides," J. Chem Ecol., Oct. 2013, pp. 1335-1342, vol. 39.
Chernin, L. S., et al., "Chitinolytic Activity in *Chromobacterium violaceum*: Substrate Analysis and Regulation by Quorum Sensing," J Bacteriol., 1998, pp. 4435-4441, vol. 180, No. 17.
Clark, E. M., et al., "Improved Histochemical Techniques for the Detection of *Acremonium coenophilum* in Tall Fescue and Methods of in vitro Culture of the Fungus," J. Microbiol Methods, 1983, pp. 149-155, vol. 13.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Clay, K., "Effects of fungal endophytes on the seed and seedling biology of *Lolium perenne* and *Festuca arundinacea*," Oecologia, 1987, pp. 358-362, vol. 73.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Coombs, J. T., et al., "Isolation and Identification of Actinobacteria from Surface-Sterilized Wheat Roots," Applied and Environmental Microbiology, 2003, pp. 5603-5608, vol. 69, No. 9.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) Merril) Against Challenge Inoculation with *R. solani*," Journal of Applied Science and Research, 2014, pp. 70-84, vol. 2, No. 5.

(56) References Cited

OTHER PUBLICATIONS

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.

Dbget, "Orthology: K14454," 2005, 2 pages, can be retrieved at <URL:http://www.genome.jp/dbget-bin/www_bget?ko:K14454>.

De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "*Epicoccum nigrum* P16, a Sugarcane Endophyte, Produces Antifungal Compounds and Induces Root Growth," PLoS One, 2012, pp. 1-10, vol. 7, No. 6.

De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Djordjevic, D., et al., "Microtiter Plate Assay for Assessment of *Listeria monocytogenes* Biofilm Formation," Annl Environ Microbiol., 2002, pp. 2950-2958, vol. 68, No. 6.

Don, R. H., et al., "Properties of Six Pesticide Degradation Plasmids Isolated From Alcaligenes Paradoxus and *Alcaligenes eutrophus*," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 1 Page.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than Blast," Bioinformatics, 2010, pp. 2460-2461, vol. 26, No. 19.

Edgar, R. C., "UPARSE: Highly Accurate OTU Sequences From Microbial Amplicon Reads," Nat Methods, 2013, pp. 996-998, vol. 10, No. 10.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS One, 2013, vol. 8, No. 6, 13 pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013, 18 Pages.

El-Shanshoury, A. R., "Growth Promotion of Wheat Seedlings by *Streptomyces atroolivaceus*," Journal of Agronomy and Crop Science, 1989, pp. 109-114, vol. 163.

Emerson, D., et al., Identifying and Characterizing Bacteria in an Era of Genomics and Proteomics, BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

Faria, D. C., et al., "Endophytic Bacteria Isolated from Orchid and Their Potential to Promote Plant Growth," World J Microbiol Biotechnol., 2013, pp. 217-221, vol. 29.

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161, vol. 8.

Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.

Fincher, G. B., "Molecular and Cellular Biology Associated with Endosperm Mobilization in Germinating Cereal Grains," Annu Rev Plant Phvsiol Plant Mol Biol., 1989, pp. 305-346, vol. 40.

Fisher, P. J., et al., "Fungal saprobes and pathogens as endophytes of rice (*Oryza sativa* L.)," New Phytol., 1992, pp. 137-143, vol. 120.

Fisher, P. R., et al., "Isolation and Characterization of the Pesticide-Degrading Plasmid pJP1 from *Alcaligenes paradoxus*," J Bacteriol., 1978, pp. 798-804, vol. 135, No. 3.

Franco, C., et al., "Actinobacterial Endophytes for Improved Crop Performance," Australasian Plant Pathology, 2007, pp. 524-531, vol. 36.

Fulthorpe, R. R., et al., "Distantly Sampled Soils Carry Few Species in Common," ISME J., 2008, pp. 901-910, vol. 2.

Gantner, S., et al., "Novel Primers for 16S rRNA-based Archaeal Community Analyses in Environmental Samples," J Microbiol Methods, 2011, pp. 12-18, vol. 84.

Gao, Z., et al., "Quantitation of Major Human Cutaneous Bacterial and Fungal Populations," J Clin Microbiol., 2010, pp. 3575-3581, vol. 48, No. 10.

Garazzino, S., et al., "Osteomyelitis Caused by *Enterobacter cancerogenus* Infection following a Traumatic Injury: Case Report and Review of the Literature," J Clin Microbiol., Mar. 2005, vol. 43, No. 3, pp. 1459-1461.

Gasser, I., et al., "Ecology and Characterization of Polyhydroxyalkanoate-Producing Microorganisms on and in Plants," FEMS Microbiol Ecol., 2010, pp. 142-150, vol. 70.

Gavrish, E, et al., "*Lentzea* sp. MS6 16S Ribosomal RNA Gene, Partial Sequence," NCBI GenBank Accession No. EF599958. Submitted May 9, 2007, 1 page.

Gebhardt, J., et al., "Characterization of a single soybean cDNA encoding cytosolic and glyoxysomal isozymes of aspartate aminostransferase," Plant Molecular Biology, 1998, pp. 99-108, vol. 37.

GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 pages, can be retrieved at <URL:https://www.ncbi.nlm.nih.gov/nuccore/AF034210>.

GenBank: JN210900.1, "*Enterobacter* sp. WS05 16S ribosomal RNA gene, partial sequence," NCBI, Sep. 24, 2012, 1 page, can be retrieved at <URL:https://www.ncbi.nlm.nih.gov/nuccore/jn210900>.

GenBank: NP_001237541.1, "Aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1>.

NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.

NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1>.

NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.

NCBI GenBank: EBI accession No. EM Std:JQ759988, "*Dothideomycetes* sp. genotype 226 isolate FL0175 internal transcribed spacer 1, partial sequence; 5.85 ribosomal RNA gene and

(56) References Cited

OTHER PUBLICATIONS internal transcribed spacer 2, complete sequence; and 28S ribosomal RNA gene, partial sequence," May 17, 2012, 2 Pages.
NCBIi GenBank: EBI accession No. EM Std:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. EU 977189, Jan. 21, 2009, 4 Pages, Smith, S.A., et al., "Bioactive endophytes warrant intensified exploration and conservation," PloS One 3(8):E3052, 2008.
GenEmbl database, GenEmbl Record No. KF011597, *Paenibacillus* strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, Seq ID 1." Aug. 15, 2013, 1 Page.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of *Sarocladium* (Hypocreales)," Persoonia, 2015, pp. 10-24, vol. 34.
Gitaitis, R., et al., "The Epidemiology and Management of Seedborne Bacterial Diseases," Annu Rev Phytopathol., 2007, pp. 371-397, vol. 45.
Grondona, I., et al., "Tusal® , a commercial biocontrol formulation based on Trichoderma," Bulletin OILB/SROP, 2004, pp. 285-288, vol. 27, No. 8.
Gu, O., et al., "*Glycomyces sambucus* sp. nov., an endophytic actinomycete islolated from the stem of *Sambucus adnata* Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in *Pseudomonas aeruginosa*," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hamayun, M., et al., "*Cladosporium sphaerospermum* as a new plant growth-promoting endophyte from the roots of *Glycine max* (L.) Merr," World Journal of Microbiology and Biotechnology, Kluwer Academic Publishers, Feb. 15, 2009, pp. 627-632, vol. 25, No. 4.
Hanson, L.E., "Reduction of Verticillium Wilt Symptoms in Cotton Following Seed Treatment with *Trichoderma virens*," The Journal of Cotton Science, 2000, pp. 224-231, vol. 4, No. 4.

Hanson, L.E., "Reduction of Verticillium Wilt Symptoms in Cotton Following Seed Treatment with *Trichoderma virens*," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P. R., et al., "Dynamics of Seed-Borne Rice Endophytes on Early Plant Growth Stages," PLoS One, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "*Enterobacter cloacae* is an endophytic symbiont of corn," Mycopathologia, 1995, pp. 117-125, vol. 129.
Hoffman, M., et al., "Diverse Bacteria Inhabit Living Hyphae of Phylogenetically Diverse Fungal Endophytes," Applied and Environmental Microbiology, Jun. 2010, pp. 4063-4075, vol. 76, No. 12.
Hoffman, M., et al., "Endohyphal Bacterium Enhances Production of Indole-3-Acetic Acid by a Foliar Fungal Endophyte," PLoS One, Sep. 24,2013, pp. 1-8, vol. 8, Issue 9, e73132.
Howell, C.R., et al., "Induction of Terpenoid Synthesis in Cotton Roots and Control of *Rhizoctonia solani* by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.
Humann, J., et al., "Complete genome of the onion pathogen *Enterobacter cloacae* EcWSU1," Standard in Genomic Sciences, Dec. 31, 2011, vol. 5, No. 3, pp. 279-286.
Hung, P.Q., et al., "Isolation and Characterization of Endophytic Bacteria in Soybean (*Glycine* sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.
Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.

(56) References Cited

OTHER PUBLICATIONS

Johnston-Monje, D., et al., "Conservation and Diversity of Seed Associated Endophytes in *Zea* Across Boundaries of Evolution, Ethnography and Ecology," PLoS One, vol. 6, No. 6, Jun. 3, 2011, p. e20396, 22 Pages.

Johnston-Monje, D., et al., "Plant and Endophyte Relationships: Nutrient Management," Comprehensive Biotechnol., 2011, pp. 713-727, vol. 4.

Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Jung, C., et al., "The Effects of Endohyphal Bacteria on Anti-Cancer and Anti-Malaria Metabolites of Endophytic Fungi," Honors Thesis, University of Arizona, May 2012, 15 Pages.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Point Presentation dated Jan. 7, 2013.

Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.

Kasana, R. C., et al., "A Rapid and Easy Method for the Detection of Microbial Cellulases on Agar Plates Using Gram's Iodine," Curr Microbiol., 2008, pp. 503-507, vol. 57.

Khan, A.L., et al., "Salinity Stress Resistance Offered by Endophytic Fungal Interaction Between Penicillium minioluteum LHL09 and *Glycine max.* L," J. Microbiol. Biotechnol., 2011, pp. 893-902, vol. 21, No. 9.

Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.

Klaubauf, S., et al., "Molecular diversity of fungal conmunities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.

Kruger, M., et al., "DNA-Based Species Level Detection of Glomeromycota: One PCR Primer Set for All *Arbuscular mycorrhizal* Fungi," New Phvtol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.

Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.

Kusari, S., et al. "Chemical ecology of endophytic fungi: origins of secondary metabolites," Cell Press, Chem & Biol., 2012, pp. 792-798, vol. 19.

Labeda, D.P., et al., "Phylogenetic study of the species within the family Streptomycetaceae," Antonie van Leeuwenhoek, 2012, vol. 101, pp. 73-104, Springer.

Lanver, D., et al., "Sho1 and Msb2-Related Proteins Regulate Appressorium Development in the Smut Fungus *Ustilago aydis*," Plant Cell, 2010, pp. 2085-2101, vol. 22.

Laus, M. C., et al., "Role of Cellulose Fibrils and Exopolysaccharides of Rhizobium leguminosarum in Attachment to and Infection of *Vicia sativa* Root Hairs," Mol Plant Microbe Interact., 2005, pp. 533-538, vol. 18, No. 6.

Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.

Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lehman, S.G., "Treat Cotton Seed," Review of Applied Mycology, 1945, 24, 369, 16 Pages.

Lehman, S.G., "Treat Cotton Seed," Research and Farming III, Progr. Rept., 1945, 3, 5, 16 Pages.

Leonard, C. A., et al., "Random Mutagenesis of the *Aspergillus oryzae* Genome Results in Fungal Antibacterial Activity," Int J Microbiol., 2013, vol. 2013, Article ID 901697, 6 Pages.

Li, H. M., et al., "Expression of a Novel Chitinase by the Fungal Endophyte in *Poa ampla*," Mycologia, 2004, pp. 526-536, vol. 96, No. 3.

Li, H., et al., "Endophytes and their role in phytoremediation," Fungal Diversity, 2012, pp. 11-18, vol. 54.

Li, Q., "*Agrobacterium tumefaciens* Strain TA-AT-10 16S Ribosomal RNA Gene, Partial Sequence: GenBank: KF673157.1," Submitted Sep. 17, 2013.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Phylogenetic relationships among ascomycetes: evidence from an RNA polymerase II subunit," Mol. Biol. Evol. 1999. vol. 16, No. 12, pp 1799-1808.

Liu, Y., et al., "Study on Diversity of Endophytic Bacterial Communities in Seeds of Hybrid Maize and their Parental Lines," Arch Microbiol., 2012, pp. 1001-1012, vol . 194.

Long, H. H., et al., "The Structure of the Culturable Root Bacterial Endophyte Community of *Nicotiana attenuata* is Organized by Soil Composition and Host Plant Ethylene Production and Perception," New Phytol., 2010, pp. 554-567, vol. 185.

Lopez-Lopez, A., et al., "*Phaseolus vulgaris* Seed-Borne Endophytic Community with Novel Bacterial Species such as *Rhizobium endophyticum* sp. nov.," Systematic Appl Microbiol., 2010, pp. 322-327, vol. 33.

Lorck, H., "Production of Hydrocyanic Acid by Bacteria," Physiol Plant, 1948, pp. 142-146, vol. 1.

Lugtenberg, B., et al., "Plant-Growth-Promoting Rhizobacteria," Ann. Rev. Microbiol., 2009, pp. 541-556, vol. 63.

Lundberg, D. S., et al., "Defining the Core *Arabidopsis thaliana* Root Microbiome," Nature, 2012, pp. 86-90, vol. 488, No. 7409.

Lundberg, D. S., et al., "Practical Innovations for High-Throughput Amplicon Sequencing," Nat Methods, 2013, pp. 999-1002, vol. 10, No. 10.

Ma, Y., et al., "Plant Growth Promoting Rhizobacteria and Endophytes Accelerate Phytoremediation of Metalliferous Soils," Biotechnology Advances, 2011, pp. 248-258, vol. 29.

Madi, L. et al., "Aggregation in Azospirillum brasilense Cd: Conditions and Factors Involved in Cell-to-Cell Adhesion," Plant Soil, 1989, pp. 89-98, vol. 115.

Mandyam, K., et al., "Mutualism-parasitism paradigm synthesized from results of root-endophyte models", Frontiers in Microbiology, Jan. 12, 2015, pp. 1-14, vol. 5.

(56) References Cited

OTHER PUBLICATIONS

Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the Its Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.
Marasco, R., et al., "A Drought Resistance-Promoting Microbiome is Selected by Root System Under Desert Farming," PLoS One, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of *Nicotiana tabacum* Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in *Rhizobium leguminosarum biovar trifolii*," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol of chickpea root rot using endophytic actinobacteria", Biocontrol, vol. 56, No. 5, Mar. 12, 2011, pp. 811-822, XP036215297.
Miyoshi-Akiyama, T., et al., "Multilocus Sequence Typing (MLST) for Characterization of *Enterobacter cloacae*," PLoS One, 2013, vol. 8, No. 6, 10 Pages, e66358.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.

Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato, " Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of *Enterobacter cloacae* on Macadamia and Identifying Associated Volatiles of Gray Kernel of Macadamia in Hawaii," Plant Disease, Oct. 2007, vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," Plos One, Jun. 2014, vol. 9, Issue 6, e97629, pp. 1-11.
Orole, O. O., et al., "Bacterial and fungal endophytes associated with grains and roots of maize," Journal of Ecology and the Natural Enviornment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M. A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, 52 Pages, [online][Retrieved Aug. 11, 2016] Retrieved from the Internet <URL:http://www.philrice.gov.ph/2012-rd-highlights/>.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval *Helicoverpa zea* (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.

(56) References Cited

OTHER PUBLICATIONS

R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.

Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.

Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.

Ravel, C., et al., "Beneficial effects of *Neotyphodium lolii* on the growth and the water status in *Perennial ryegrass* cultivated under nitrogen deficiency or drought stress," Agronomie, 1997, pp. 173-181, vol. 17.

Redman, R. S., et al., "Thermotolerance Generated by Plant/Fungal Symbiosis," Science, Nov. 2002, vol. 298, 1 Page (with 4 pages of supplemental material).

Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.

Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.

Riess, K., et al., "High genetic diversity at the regional scale and possible speciation in *Sebacina epigaea* and *S. incrustans*," BMC Evolutionary Biology, 2013, vol. 13, No. 102, 17 Pages.

Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

Rodriguez, H., et al., "Expression of a Mineral Phosphate Solubilizing Gene From *Erwinia herbicola* in Two Rhizobacterial Strains," J Biotechnol., 2001, pp. 155-161, vol. 84.

Rodriguez, R.J., et al., "Stress Tolerance in Plants via Habitat-Adapted Symbiosis," ISME J., 2008, pp. 404-416, vol. 2.

Rodriguez-Navarro, D., et al., "Soybean Interactions with Soil Microbes, Agronomical and Molecular Aspects," Agronomy for Sustainable Development, 2011, pp. 173-190, vol. 31, No. 1.

Roessner, U., et al., "Metabolic Profiling Allows Comprehensive Phenotyping of Genetically or Environmentally Modified Plant Systems," Plant Cell, 2001,pp. 11-29, vol. 13.

Rosado, A. S., et al., "Phenotypic and Genetic Diversity of *Paenibacillus azotofixans* Strains Isolated from the Rhizoplane or Rhizosphere Soil of Different Grasses," J App Microbiol., 1998, pp. 216-226, vol. 84.

Rosenblueth, A., et al., "Seed Bacterial Endophytes: Common Genera, Seed-to-Seed Variability and Their Possible Role in Plants," Acta Hort., 2012, pp. 39-48, vol. 938.

Rosenblueth, M., et al., "Bacterial Endophytes and Their Interactions With Host," Molecular Plant-Microbe Interactions, 2006, pp. 827-837, vol. 19, No. 8.

Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Samac, D.A., et al., "Recent Advances in Legume-Microbe Interactions: Recognition, Defense Response, and Symbiosis from a Genomic Perspective," Plant Physiol., 2007, pp. 582-587, vol. 144.

Samways, M.J., et al., "Assessment of the Fungus *Cladosporium oxyspoum* (Berk. and Curt.) As a Potential BioControl Agent Against Certain Homoptera," Elsevier Science Publioshers B.V., Jan. 1, 1986, pp. 231-239.

Sardi, P., et al., "Isolation of Endophytic *Streptomyces* Strains from Surface Sterilized Roots," Applied and Environmental Microbiology, 1992, pp. 2691-2693, vol. 58, No. 8.

Sarwar, M., et al., "Tryptophan Dependent Biosynthesis of Auxins in Soil," Plant Soil, 1992, pp. 207-215, vol. 147.

Saunders, M., et al., "Host-Synthesized Secondary Compounds Influence the in Vitro Interactions between Fungal Endophytes of Maize", Applied and Environmental Microbiology, Nov. 9, 2007, pp. 136-142, vol. 74 , No. 1.

Schmieder, R., et al., "Quality Control and Preprocessing of Metagenomic Datasets," Bioinformatics, 2011, pp. 863-864, vol. 27, No. 6.

Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.

Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay for the Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Shankar, M., et al.,"Root colonization of a rice growth promoting strain of *Enterobacter cloacae*," Journal of Basic Microbiology, 2011, pp. 523-530, vol. 51.

Shiraishi, A., et al., "Nodulation in black locust by the ammaproteobacteria *Pseudomonas* sp. and the *Betaproteobacteria burkholderia* sp", Systematic and Applied Microbiology, Aug. 2010, pp. 269-274, vol. 33, No. 5.

Simola, L., et al., "The Effect of Some Protein and Non-Protein Amino Acids on the Growth of *Cladosporium herbarum* and *Trichotheeium roseum*," Effect of Amino Acids on Fungi, Physiologia Plantarum, 1979, pp. 381-387, vol. 46.

Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.

Soares, M. M. C. N., et al., "Screening of Bacterial Strains for Pectinolytic Activity: Characterization of the Polygalacturonase Produced by *Bacillus* SP," Revista de Microbiolgia, 1999, pp. 299-303, vol. 30.

Soe, K.M., et al., "Effects of endophytic actinomycetes and *Bradyrhizobium japonicum* strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar *Bradyrhizobium yuanmingense* MAS34 and *Streptomyces griseoflavus* P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Germination of *Hordeum brevisubulatum* under Temperature and Water Stress Conditions," Acta Agrestia Sinica, 2010, pp. 834-837, vol. 18, No. 6. (English Abstract).

Souleimanov, A., et al., "The Major Nod Factor of *Bradyrhizobium japonicum* Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by *Rhizobium tropici*," Arch Microbiol., 2012, pp. 197-206, vol. 194.

(56) References Cited

OTHER PUBLICATIONS

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013.
Sword, G., "Fungal Endophytes to Protect Cotton from Insects and Nematodes," Power Point Presentation dated Dec. 7, 2012, 20 Pages.
Sword, G., "Natural Enemies—The Forgotten Basis of IPM?," Power Point Presentation dated Sep. 6, 2013.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.
Tamura, K., et al., "Estimation of the numbers nucleotide substitutions in the control region of mitochondrial DNA in humans and chimpanzees," Molecular Biology and Evolution, 1993, vol. 10, No. 3, pp. 512-526.
Taylor, A. G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in *Spodoptera litura* (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.
Theis, K. R., et al., "Uncultured Bacterium Clone GM2G18201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces lydicus WYEC108 and the Pea Plant (Pisum Sativum)," Applied and Environmental Microbiology, May 2002, pp. 2161-2171, vol. 68, No. 5.

Trichoderma definition, 2016, 6 Pages, [online] [Retrieved on Sep. 16, 2016,] Retrieved from the Internet <URL:https://en.wikipedia.org/wiki/Trichoderma>.
Trotel-Aziz, P., et al., "Characterization of New Bacterial Biocontrol Agents *Acinetobacter, Bacillus, Pantoea* and *Pseudomonas* spp. Mediating Grapevine Resistance Against *Botrytis cinerea*," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
U'Ren, J.M., et al., "Host and geographic structure of endophytic and endolichenic fungi at the continental scale," American Journal of Botany, May 1, 2012, pp. 898-914, vol. 99, No. 5.
Usadel, B., et al., "The Plant Transcriptome-From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Valencia, E., et al., "Mini-review: Brazilian fungi diversity for biomass degradation," Fungal Genetics and Biology, 2013, pp. 9-18, vol. 60.
Van Der Lelie, D., et al., "Poplar and its Bacterial Endophytes: Coexistence and Harmony," Critical Rev Plant Sci., 2009, pp. 346-358, vol. 28.
Verkley, G., et al., "*Paraconiothyrium*, a new genus to accommodate the mycoparasite *Coniothyrium minitans*, anamorphs of *Paraphaeosphaeria*, and four new species," Studies in Mycology, 2004, pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "*Pseudomonas thiveralensis* Strain IEHa 16S Ribosomal RNA Fene, Partial Sequence," NCBI GenBank Accession No. GQ169380.1, Submitted May 15, 2009.
Visagie, C.M., et al., "Identification and nomenclature of the genus *Penicillium*," Studies in Mycology, Jun. 2014, pp. 343-371, vol. 78.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of *Acer saccharum* in eastern North America," Mycological Progress, May 2002, pp. 147-154, vol. 1, Issue 2.
Vujanovic, V., et al., "Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol, 2007, vol. 29, p. 451.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.

(56) References Cited

OTHER PUBLICATIONS

Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulata," Arch Microbiol., 1975, pp. 207-216, vol. 105.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of *Tall fescue* and *Perennial ryegrass*," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing *Bacillus subtilis* (HYT-12-1) on Tomato Seedlings," World J Microbiol Biotechnol., 2014, pp. 835-845, vol. 30.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of *Acinetobacter* and *Enterobacter* as potential Biocontrol Agents Against Ralstonia Wilt of Tomato," Biological Control, 2009, vol. 48, pp. 252-258.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
Yezerski, A., et al., "The Effects of the Presence of Stored Product Pests on the Microfauna of a Flour Community," Journal of Applied Microbiology, 2005, pp. 507-515, vol. 98.
You, Y., et al., "Analysis of Genomic Diversity of Endophytic Fungal Strains Isolated from the Roots of *Suaeda japonica* and *S. maritima* for the Restoration of Ecosystems in Buan Salt Marsh," Korean Journal of Microbiology and Biotechnology, 2012, pp. 287-295, vol. 40, No. 4. (with English Abstract).
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal Endophyte *Paecilomyces* sp. in Cotton on the Roo-Knot Nematode Meloidogyne incognita," poster dated Jan. 7, 2013.
Zhu et al., *Helminthosporium velutinum* and *H. aquaticum* sp. nov. from aquatic habitats in Yunnan Province, China. Phytotaxa, 2016, vol. 253, No. 3, pp. 179-190.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuccaro, A., et al., "Endophytic Life Strategies Decoded by Genome and Transcriptome Analyses of the Mutualistic Root Symbiont *Piriformospora indica*," PLOS Pathogens, 2011, vol. 7, No. 10, e1002290.
Zuniga, A., et al., "Quorum Sensing and Indole-3-Acetic Acid Degradation Play a Role in Colonization and Plant Growth Promotion of *Arabidopsis thaliana* by *Burkholderia phytofirmans* PsJN," Mol Plant Microbe Interact., 2013, pp. 546-553, vol. 26, No. 5.
Govindarajan, M. et al., "Effects of the Inoculation of *Burkholderia vietnamensis* and Related Endophytic Diaztrophic Bacteria on Grain Yield of Rice", Mircobial Ecology, Apr. 4, 2007, 17 pages.
Lind, A., et al., "Drivers of genetic diversity in secondary metabolic gene clusters within a fungal species", PLOS Biology, Nov. 17, 2017, 26 pages.
Sha, T. et al., "Genetic diversity of the endemic gourmet mushroom *Thelephora ganbajun* from southwestern China", Microbiology (2008), 154, 3460-3468.
Sugita, T. et al., "Intraspecies Diversity *Cryptococcus laurentii* as Revealed by Sequences of Internal Transcribed Spacer Regions and 28S rRNA Gene and Taxonomic Position of *C. laurentii* Clinical Isolates", Journal of Clinical Microbiology, Apr. 2000, p. 1468-1471.
PCT International Search Report and Written Opinion PCT/AU2018/050387, dated Apr. 27, 2018, 8 pages.
PCT International Search Report and Written Opinion for PCT/US2018/051467, dated Feb. 4, 2019, 22 pages.
United States Patent Office, Non-Final Office Action, U.S. Appl. No. 14/766,065, dated Oct. 27, 2017, 11 Pages.
United States Patent Office, Non-Final Office Action, U.S. Appl. No. 14/964,429, dated Aug. 9, 2016, 6 Pages.
United States Patent Office, Final Office Action, U.S. Appl. No. 14/964,429, dated May 31, 2017, 9 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/063,350, dated Nov. 10, 2016, 18 Pages.
United States Patent Office, Final Office Action, U.S. Appl. No. 14/614,193, dated Dec. 22, 2016, 13 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/107,965, dated Jun. 21, 2018, 27 Pages.
Abello, J., et al., "*Agrobacterium*-mediated transformation of the endophytic fungus *Acremonium implicatum* associated with *Brachiaria* grasses", Mycological Research, pp. 407-413, vol. 112, Pt 3.
Al-Askar AA, "Microbiological studies on the in vitro inhibitory effect of *Streptomyces collinus* albescens against some phytopathogenic fungi", African Journal of Microbiology Research, 2012, 6: 3277-3283 & GenBank Accession No. AB184101, May 20, 2008.
Ardakani, M.R. et al., "Absorption of N, P, K through triple inoculation of wheat (*Triticum aestivum* L.) by *Azospirillum brasilense*,

(56) References Cited

OTHER PUBLICATIONS

*Streptomyces* sp., *Glomus intraradices* and manure application," Physiol Mol Biol Plants, 2011, vol. 17, No. 2, pp. 181-192.
Bandara, W.M.M.S., et al., "Interactions among endophytic bacteria and fungi: effects and potentials", Journal of Biosciences, Dec. 2006, vol. 31, No. 5, pp. 645-650.
Barnett, S., et al., "Selection of microbes for control of *Rhizoctonia* root rot on wheat using a high throughput pathosystem", Biological Control, 6 Jul. 2017, 113: 45-57.
Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.
Bashan, Yoav E., et al., "Alginate Beads as Synthetic Inoculant Carriers for Slow Release of Bacteria that Affect Plant Growth," Applied and Environmental Microbiology, pp. 1089-1098, May 1986.
Bragantia, et al: "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).
Chenhua Li , et al., "Change in deep soil microbial communities due to long-term fertilization," Soil Biology and Biochemistry, vol. 75, Mar. 5, 2014, pp. 264-272, XP055530941.
Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.
De Medeiros, L., et al., "Evaluation of Herbicidal Potential of Depsides from *Cladosporium uredinicola* an Endophytic Fungus found in Guava Fruit," J. Braz. Chem. Soc., 2012, vol. 23, No. 8, p. 1551-1557.
De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Fatima Z et al, "Antifungal activity of plant growth-promoting rhizobacteria isolates against *Rhizoctonia solani* in wheat", African Journal of Biotechnology, 2009, 8: 219-225.
GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.
NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hain, T., et al., "Chitinolytic transgenes from *Streptomyces albidoflavus* as phytochemicals defences against herbivorous insects, use in transgenic plants and effect in plant development", International Journal of Systematic Bacteriology, Jan. 1997, vol. 47, No. 1, pp. 202-206.
Hanshew, A., et al., "Characterization of *Actinobacteria* Associated with Three Ant-Plant Mutualisms", Microbial Ecology, Aug. 6, 2017, vol. 69, No. 1, pp. 192-203.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Iverson, C., et al, "The taxonomy of *Enterobacter sakazakii*: proposal of a new genus *Cronobacter* gen. nov. and descriptions of *Cronobacter sakazakii* comb. nov. *Cronobacter sakazakii* subsp. sakazakii, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter genomospecies I*", BMC Evolutionary Biology 2007, Apr. 17, 2017, 11 pages.
Joe, M.M. et al., "Development of alginate-based aggregate inoculants of *Methylobacterium* sp. and *Azospirillum brasilense* tested under in vitro conditions to promote plant growth," Journal of Applied Microbiology 2013, 116(2):408-423, XP055225426, Nov. 22, 2013.
Li, M., et al., "ATP Modulates the Growth of Specific Microbial Strains", Current Microbiology, May 30, 2010, vol. 62, No. 1, pp. 84-89.
Manoharan, M. J. et. Al., "Survival of flocculated cells in alginate and its inoculatin effect on growth and yield of maize under water deficit conditions," EP J of Siil Biology, Gauthier-Villars, Montrouge, FR, vol. 50, Mar. 7, 2012, pp. 198-206, XP028421147.
Murali, Gopal, et al., "Microbiome Selection Could Spur Next-Generation Plant Breeding Strategies," Frontiers in Microbiology, vol. 7, Dec. 7, 2016, XP055531064.
Ogbo, F., et al., "Some Characteristics of a Plant Growth Promoting iEnterobacter/isp. Isolated from the Roots of Maize", Advances in Microbiology, Jan. 1, 2012, vol. 2, No. 3, pp. 368-374.
Orakçi GE et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
"Sequence Alignment of JQ047949 with Instant Seq ID No. 2," Search conducted on Jan. 2, 2019. 2 pages.
Sharma et al., "Detection and identification of bacteria intimately associated with fungi of the order Sebacinales", Cellular Microbiology, Aug. 5, 2008, pp. 2235-2246, vol. 10, No. 11.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Yashiro et al., "Effect of *Streptomycin* Treatment on Bacterial Community Structure in the Apple Phyllosphere," PLOS One, May 21, 2012, vol. 7, No. 5, 10 pages.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
Bently, S.D., et al, "Complete genome sequence of the model actinomycete *Streptomyces coelicolor* A3(2)," Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of *Streptomyces* spp. in sorghum and rice", SpringerPlus, 2/1/574, pp. 1-8, http://www.springerplus.com/content/2/1/574, 2013.
Groppe, K., et al., "Interaction between the endophytic fungus *Epichloë bromicola* and the grass *Bromus erectus*: effects of endophyte infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism *Streptomyces avermitilis*," Nat Biotechnol. May 2003;21 (5) :526-31. Epub Apr. 14, 2003. (Year: 2003).
Langille, M., et al., "Predictive functional profiling of microbial communities, using 16S rRNA marker gene sequences", Nature Biotechnology, vol. 31, No. 9, Sep. 2013, 11 pages.
Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62. (Year: 2005).

(56) References Cited

OTHER PUBLICATIONS

Pacovsky, R., "Carbohydrate, protein and amino acid status of Glycine-Glomus-Bradyrhizobium symbioses," Physiologia Pantarium; 75:346-354, 1989).

Wiebold, M., et al., "Agriculture Experiment Station, College of Agriculture, Food & Natural Resources, University of Missouri, Special Report 589, pp. 1-124)."

* cited by examiner

ENDOPHYTE COMPOSITIONS AND THE METHODS FOR IMPROVEMENT OF PLANT TRAITS

CROSS REFERENCE TO RELATED APPLICATIONS

This application claims priority to Provisional Application No. 62/551,724, filed Aug. 29, 2017; Provisional Application No. 62/467,734, filed Mar. 6, 2017; Provisional Application No. 62/467,737, filed Mar. 6, 2017; Provisional Application No. 62/466,250, filed Mar. 2, 2017; Provisional Application No. 62/465,820, filed Mar. 2, 2017; Provisional Application No. 62/465,833, filed Mar. 2, 2017; and Provisional Application No. 62/465,818, filed Mar. 1, 2017, the disclosures of which are incorporated by reference in their entirety.

SEQUENCE LISTING

The instant application contains a Sequence Listing with 51 sequences which has been submitted via EFS-Web and is hereby incorporated by reference in its entirety. Said ASCII copy, created on Nov. 29, 2017, is named 39060_US_10100_Sequence_Listing.txt, and is 34,963 bytes in size.

FIELD OF THE INVENTION

This invention relates to compositions and methods for improving the traits of plants, particularly plants important for human or animal consumption, for example rice (*Oryza sativa* and related varieties), soy (*Glycine max* and related varieties), wheat (*Triticum aestivum* and related varieties), and corn (*Zea mays* and related varieties). For example, this invention describes microbes that are capable of living within or heterologously disposed to a plant, and which can be used to impart improved traits to plants with which they are or have been heterologously disposed. The disclosed invention also describes methods of improving plant element characteristics by introducing microbes to parental plants. Further, this invention also provides methods of treating plant elements with microbes that are capable of living within a plant, particularly rice, soy, wheat, and corn, to impart improved yield, and other agronomic characteristics to that plant.

BACKGROUND

According the United Nations Food and Agricultural Organization, the world's population will exceed 9.6 billion people by the year 2050, which will require significant improvements in agricultural to meet growing food demands. There is a need for improved agricultural plants that will enable the nearly doubled food production demands with fewer resources and more environmentally sustainable inputs, for plants with improved responses to various biotic and abiotic stresses.

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops, and shifts in the climate have been linked to production instability as well as changing pest and disease pressures, driving an urgent need for novel solutions to crop improvement. In addition to their long development and regulatory timelines, public fears of GM-crops and synthetic chemicals have challenged their use in many key crops and countries, resulting in a lack of acceptance for many GM traits and the exclusion of GM crops and many synthetic chemistries from some global markets. Thus, there is a significant need for innovative, effective, environmentally-sustainable, and publicly-acceptable approaches to improving the yield and other agronomically important characteristics of plants.

Provided herein are methods and compositions for improving agronomically important characteristics of plants by associating those plants with the disclosed endophytes.

SUMMARY OF INVENTION

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* as deposited under NRRL Culture Deposit No. 67466.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a modified endophyte of the genus *Periconia* derived from the endophyte as deposited under NRRL Culture Deposit No. 67466.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* as deposited under NRRL Culture Deposit No. 67466.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a modified endophyte of the genus *Periconia* derived from the endophyte as deposited under NRRL Culture Deposit No. 67466.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* as deposited under NRRL Culture Deposit No. 67466.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Periconia* derived from the endophyte as deposited under NRRL Culture Deposit No. 67466.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* as deposited under NRRL Culture Deposit No. 67467.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a modified endophyte of the genus *Curvularia* derived from the endophyte as deposited under NRRL Culture Deposit No. 67467.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* as deposited under NRRL Culture Deposit No. 67467.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a modified endophyte of the genus *Curvularia* derived from the endophyte as deposited under NRRL Culture Deposit No. 67467.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* as deposited under NRRL Culture Deposit No. 67467.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Curvularia* derived from the endophyte as deposited under NRRL Culture Deposit No. 67467.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* as deposited under NRRL Culture Deposit No. B67465.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a modified endophyte of the genus *Enterobacter* derived from the endophyte as deposited under NRRL Culture Deposit No. B67465.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33 wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* as deposited under NRRL Culture Deposit No. 67466, wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* as deposited under NRRL Culture Deposit No. 67466, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* as deposited under NRRL Culture Deposit No. 67466, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* as deposited under NRRL Culture Deposit No. 67467, wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* as deposited under NRRL Culture Deposit No. 67467, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* as deposited under NRRL Culture Deposit No. 67467, wherein the plant element is a seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the plant element is a seed.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the plant element is a seed.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the plant element is a seed.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the plant element is a seed.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* as deposited under NRRL Culture Deposit No. B67465, wherein the plant element is a seed.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a modified endophyte of the genus *Enterobacter* derived from the endophyte as deposited under NRRL Culture Deposit No. B67465, wherein the plant element is a seed.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33 wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* as deposited under NRRL Culture Deposit No. 67466, wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* as deposited under NRRL Culture Deposit No. 67466, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* as deposited under NRRL Culture Deposit No. 67466, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* as deposited under NRRL Culture Deposit No. 67467, wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* as deposited under NRRL Culture Deposit No. 67467, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* as deposited under NRRL Culture Deposit No. 67467, wherein the plant element is a seed, wherein the seed is modified.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the plant element is a seed, wherein the seed is modified.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the plant element is a seed, wherein the seed is modified.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the plant element is a seed, wherein the seed is modified.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the plant element is a seed, wherein the seed is modified.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* as deposited under NRRL Culture Deposit No. B67465, wherein the plant element is a seed, wherein the seed is modified.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a modified endophyte of the genus *Enterobacter* derived from the endophyte as deposited under NRRL Culture Deposit No. B67465, wherein the plant element is a seed, wherein the seed is modified.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a modified endophyte of the genus *Periconia* derived from the endophyte as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Periconia* derived from the endophyte as deposited under NRRL Culture Deposit No. 67466, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* as deposited under NRRL Culture Deposit No. 67467, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* as deposited under NRRL Culture Deposit No. 67467, wherein the endophyte to heterologously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the endophyte to heterolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Curvularia* as deposited under NRRL Culture Deposit No. 67467, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a modified endophyte of the genus *Curvularia* derived from the endophyte as deposited under NRRL Culture Deposit No. 67467, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* as deposited under NRRL Culture Deposit No. B67465, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a modified endophyte of the genus *Enterobacter* derived from the endophyte as deposited under NRRL Culture Deposit No. B67465, wherein the endophyte to hetergolously disposed to the plant element in a formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 98%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 98%.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 98%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is at least 98%.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is at least 98%.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is at least 98%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is at least 98%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is at least 98%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is at least 98%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is at least 98%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 99%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 99%.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is at least 99%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is at least 99%.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is at least 99%.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is at least 99%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is at least 99%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is at least 99%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is at least 99%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is at least 99%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is 100%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is 100%.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is 100%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is 100%.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is 100%.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is 100%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is 100%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is 100%.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is 100%.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is 100%.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 100 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 100 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 100 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 100 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 100 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is determined over a region of alignment of at least 100 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 100 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 100 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is determined over a region of alignment of at least 100 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is determined over a region of alignment of at least 100 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 200 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 200 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 200 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 200 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 200 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is determined over a region of alignment of at least 200 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 200 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 200 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is determined over a region of alignment of at least 200 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is determined over a region of alignment of at least 200 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 300 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 300 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 300 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 300 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 300 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is determined over a region of alignment of at least 300 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 300 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 300 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is determined over a region of alignment of at least 300 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is determined over a region of alignment of at least 300 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 400 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 400 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 400 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 400 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 400 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is determined over a region of alignment of at least 400 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 400 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 400 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is determined over a region of alignment of at least 400 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is determined over a region of alignment of at least 400 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length and root area in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 500 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, dry shoot biomass, and yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 500 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Periconia* and comprises at least one polynucleotide sequence at least 97% identical to a sequence selected from the group consisting of SEQ ID NO: 32 and 33, wherein the percent identity is determined over a region of alignment of at least 500 nucleotides.

In one aspect, the invention provides a method of improving a trait of agronomic importance in a soybean plant, comprising heterologously disposing an endophyte to a soybean plant element in an amount effective to increase a trait of agronomic importance selected from the group consisting of root length, root area and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 500 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of root length, and yield in the plant derived from the treated plant element relative to a plant derived from a reference plant element, wherein the endophyte is a member of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Asperigullus* and comprises at least one polynucleotide sequence at least 97% identical to SEQ ID NO: 39, wherein the percent identity is determined over a region of alignment of at least 500 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate, root length, dry shoot biomass, and yield in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 500 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Coniochaeta* and comprises at least one polynucleotide sequence at least 97% identical to a sequence selected from the group consisting of SEQ ID NOs: 40-43, wherein the percent identity is determined over a region of alignment of at least 500 nucleotides.

In one aspect, the invention provides a method of improving a trait of agronomic importance in a wheat plant, comprising heterologously disposing an endophyte to a wheat plant element in an amount effective to increase a trait of agronomic importance selected from the group consisting of germination rate and dry biomass in the plant derived from the treated plant element relative to a plant derived from a reference plant element, wherein the endophyte is a member of the genus *Pestalotiopsis* and comprises at least one polynucleotide sequence at least 97% identical to a sequence selected from the group consisting of SEQ ID NOs: 44-48, wherein the percent identity is determined over a region of alignment of at least 500 nucleotides.

In one aspect, the invention provides a method of improving a trait of agronomic importance in a rice plant, comprising heterologously disposing an endophyte to a rice plant element in an amount effective to increase dry root biomass in the plant derived from the treated plant element relative to a plant derived from a reference plant element, wherein the endophyte is a member of the genus *Enterobacter* and comprises at least one polynucleotide sequence at least 97% identical to a sequence selected from the group consisting of SEQ ID NOs: 49-51, wherein the percent identity is determined over a region of alignment of at least 500 nucleotides.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the oil is rapeseed or NEEM.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the oil is rapeseed or NEEM.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the oil is rapeseed or NEEM.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the oil is rapeseed or NEEM.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the oil comprises erucic acid.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the oil comprises erucic acid.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the oil comprises erucic acid.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the oil comprises erucic acid.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the oil comprises herbicidal or insecticidal properties.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the oil comprises herbicidal or insecticidal properties.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the oil comprises herbicidal or insecticidal properties.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the oil comprises herbicidal or insecticidal properties.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the surfactant is a non-ionic detergent.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the surfactant is a non-ionic detergent.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the surfactant is a non-ionic detergent.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the surfactant is a non-ionic detergent.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the surfactant is Tween 20 or Triton X-100.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the surfactant is Tween 20 or Triton X-100.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the surfactant is Tween 20 or Triton X-100.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the surfactant is Tween 20 or Triton X-100.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the endophyte is a modified endophyte of the genus

*Enterobacter* derived from the endophyte as deposited under NRRL Culture Deposit No. B67465, wherein the polymer is Flo Rite®, DISCO™, or Kannar® Universal Wonder.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the microbial active ingredient comprises a spore suspension.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the microbial active ingredient comprises a spore suspension.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the microbial active ingredient comprises a spore suspension.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the microbial active ingredient comprises a spore suspension.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the microbial active ingredient comprises spray dried spores.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the microbial active ingredient comprises spray dried spores.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the microbial active ingredient comprises spray dried spores.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the microbial active ingredient comprises spray dried spores.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the microbial active ingredient comprises whole cell broth.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the microbial active ingredient comprises whole cell broth.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the microbial active ingredient comprises whole cell broth.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, wherein the microbial active ingredient comprises whole cell broth.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, the formulation further comprising one or more of the following: fungicide, nematicide, bactericide, insecticide, or herbicide.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the endophyte is a modified endophyte of the genus *Enterobacter* derived from the endophyte as deposited under NRRL Culture Deposit No. B67465, the formulation further comprising one or more of the following: stabilizer, preservative, carrier, anticomplex agent, or any combination thereof.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Periconia* as deposited under NRRL Culture Deposit No. 67466, wherein the endophyte is shelf-stable.

In one aspect, the invention provides an agrochemically active microbial formulation, comprising at least one oil, surfactant, polymer, and a microbial active ingredient, wherein the endophyte is a modified endophyte of the genus *Periconia* derived from the endophyte as deposited under NRRL Culture Deposit No. 67466, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Curvularia* as deposited under NRRL Culture Deposit No. 67467, wherein the endophyte is shelf-stable.

In one aspect, the invention provides an agrochemically active microbial formulation, comprising at least one oil, surfactant, polymer, and a microbial active ingredient, wherein the endophyte is a modified endophyte of the genus *Curvularia* derived from the endophyte as deposited under NRRL Culture Deposit No. 67467, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Enterobacter* as deposited under NRRL Culture Deposit No. B67465, wherein the endophyte is shelf-stable.

In one aspect, the invention provides an agrochemically active microbial formulation, comprising at least one oil, surfactant, polymer, and a microbial active ingredient, wherein the endophyte is a modified endophyte of the genus

*Enterobacter* derived from the endophyte as deposited under NRRL Culture Deposit No. B67465, wherein the endophyte is shelf-stable.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is at least 98%.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is at least 98%.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is at least 98%.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is at least 98%.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is at least 98%.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is at least 99%.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is at least 99%.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is at least 99%.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is at least 99%.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is at least 99%.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is 100%.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is 100%.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is 100%.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is 100%.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is 100%.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is determined over a region of alignment of at least 100 nucleotides.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 100 nucleotides.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is determined over a region of alignment of at least 100 nucleotides.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is determined over a region of alignment of at least 100 nucleotides.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is determined over a region of alignment of at least 100 nucleotides.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is determined over a region of alignment of at least 200 nucleotides.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 200 nucleotides.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is determined over a region of alignment of at least 200 nucleotides.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is determined over a region of alignment of at least 200 nucleotides.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is determined over a region of alignment of at least 200 nucleotides.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is determined over a region of alignment of at least 300 nucleotides.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 300 nucleotides.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is determined over a region of alignment of at least 300 nucleotides.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is determined over a region of alignment of at least 300 nucleotides.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is determined over a region of alignment of at least 300 nucleotides.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is determined over a region of alignment of at least 400 nucleotides.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs:

34-38, wherein the percent identity is determined over a region of alignment of at least 400 nucleotides.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is determined over a region of alignment of at least 400 nucleotides.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is determined over a region of alignment of at least 400 nucleotides.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is determined over a region of alignment of at least 400 nucleotides.

In one aspect, the invention provides an agrochemically active microbial formulation, comprising at least one oil, surfactant, polymer, and a microbial active ingredient, wherein the microbial active ingredient is an endophyte of the genus *Periconia* and comprises at least one polynucleotide sequence at least 97% identical to a sequence selected from the group consisting of SEQ ID NO: 32 and 33, wherein the percent identity is determined over a region of alignment of at least 500 nucleotides.

In one aspect, the invention provides an agrochemically active microbial formulation, comprising at least one oil, surfactant, polymer, and a microbial active ingredient, wherein the microbial active ingredient is an endophyte of the genus *Curvularia* and comprises at least one polynucleotide sequence at least 97% identical to a sequence selected from the group consisting of SEQ ID NO: SEQ ID NOs: 34-38, wherein the percent identity is determined over a region of alignment of at least 500 nucleotides.

In one aspect, the invention provides an agrochemically active microbial formulation, comprising at least one oil, surfactant, polymer, and a microbial active ingredient, wherein the microbial active ingredient is an endophyte of the genus *Asperigullus* and comprises at least one polynucleotide sequence at least 97% identical to SEQ ID NO: 39, wherein the percent identity is determined over a region of alignment of at least 500 nucleotides.

In one aspect, the invention provides an agrochemically active microbial formulation, comprising at least one oil, surfactant, polymer, and a microbial active ingredient, wherein the microbial active ingredient is an endophyte of the genus *Coniochaeta* and comprises at least one polynucleotide sequence at least 97% identical to a sequence selected from the group consisting of SEQ ID NOs: 40-43, wherein the percent identity is determined over a region of alignment of at least 500 nucleotides.

In one aspect, the invention provides an agrochemically active microbial formulation, comprising at least one oil, surfactant, polymer, and a microbial active ingredient, wherein the microbial active ingredient is an endophyte of the genus *Enterobacter* and comprises at least one polynucleotide sequence at least 97% identical to a sequence selected from the group consisting of SEQ ID NOs: 49-51, wherein the percent identity is determined over a region of alignment of at least 500 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte is of the taxonomy *Periconia macrospinosa*.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the endophyte is of the taxonomy *Periconia macrospinosa*.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the endophyte is of the taxonomy *Periconia macrospinosa*.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the endophyte is of the taxonomy *Periconia macrospinosa*.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the plant element is of the genus *Triticum* and the improve trait of agronomic importance is selected from the group consisting of germination rate, dry shoot biomass, and yield.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the plant element is of the genus *Triticum* and the improve trait of agronomic importance is selected from the group consiting of germination rate, dry shoot biomass, and yield.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the plant element is of the genus *Triticum* and the improve trait of agronomic importance is selected from the group consisting of germination rate, dry shoot biomass, and yield.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the plant element is of the genus *Triticum* and the improve trait of agronomic importance is selected from the group consisting of germination rate, dry shoot biomass, and yield.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the plant element is of the genus *Glycine* and the improve trait of agronomic importance is selected from the group consisting of root length and root area.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the plant element is of the genus *Glycine* and the improve trait of agronomic importance is selected from the group consisting of root length and root area.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the plant element is of the genus *Glycine* and the improve trait of agronomic importance is selected from the group consisting of root length and root area.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the plant element is of the genus *Glycine* and the improve trait of agronomic importance is selected from the group consisting of root length and root area.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the plant element is of the genus *Zea* and the improve trait of agronomic importance is yield.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein said endophyte is of the taxonomy *Curvularia spicifera*.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein said endophyte is of the taxonomy *Curvularia spicifera*.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein said endophyte is of the taxonomy *Curvularia spicifera.*

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein said endophyte is of the taxonomy *Curvularia spicifera.*

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein said endophyte is of the taxonomy *Curvularia spicifera.*

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein said endophyte is of the taxonomy *Curvularia spicifera.*

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein said endophyte is of the taxonomy *Curvularia spicifera.*

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the plant element is of the genus *Triticum* and the improve trait of agronomic importance is selected from the group consisting of root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the plant element is of the genus *Glycine* and the improve trait of agronomic importance is selected from the group consisting of root length, germination rate, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the plant element is of the genus *Zea* and the improve trait of agronomic importance is yield.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the plant element is of the genus *Zea* and the improve trait of agronomic importance is yield.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein said endophyte is of the taxonomy *Asperigullus ruber*.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the plant element is of the genus *Triticum* and the improve trait of agronomic importance is yield.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein said endophyte is of the taxonomy *Asperigullus rube*, wherein the plant element is of the genus *Triticum* and the improve trait of agronomic importance is yield.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte is of the taxonomy *Coniochaeta prunicola*.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the endophyte is of the taxonomy *Coniochaeta prunicola*.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the endophyte is of the taxonomy *Coniochaeta prunicola*.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the endophyte is of the taxonomy *Coniochaeta prunicola*.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the plant element is of the genus *Triticum* and the improve trait of agronomic importance is selected from the group consisting of root length, germination rate, dry shoot biomass, and yield.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the plant element is of the genus *Triticum* and the improve trait of agronomic importance is selected from the group consisting of root length, germination rate, dry shoot biomass, and yield.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the plant element is of the genus *Triticum* and the improve trait of agronomic importance is selected from the group consisting of root length, germination rate, dry shoot biomass, and yield.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the plant element is of the genus *Triticum* and the improve trait of agronomic importance is selected from the group consisting of root length, germination rate, dry shoot biomass, and yield.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the plant element is of the genus *Oryza* and improve trait of agronomic importance is dry root biomass.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte is of the taxonomy *Pestalotiopsis neglecta*.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the endophyte is of the taxonomy *Pestalotiopsis neglecta*.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the endophyte is of the taxonomy *Pestalotiopsis neglecta*.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the endophyte is of the taxonomy *Pestalotiopsis neglecta*.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the endophyte is of the taxonomy *Pestalotiopsis neglecta*.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the plant element is of the genus *Triticum* and the improve trait of agronomic importance is selected from the group consisting of germination rate and dry shoot biomass.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the plant element is of the genus *Triticum* and the improve trait of agronomic importance is selected from the group consisting of germination rate and dry shoot biomass.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the plant element is of the genus *Triticum* and the improve trait of agronomic importance is selected from the group consisting of germination rate and dry shoot biomass.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the plant element is of the genus *Triticum* and the improve trait of agronomic importance is selected from the group consisting of germination rate and dry shoot biomass.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the plant element is of the genus *Triticum* and the improve trait of agronomic importance is selected from the group consisting of germination rate and dry shoot biomass.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein said endophyte is of the taxonomy *Enterobacter cowanii*.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein said endophyte is of the taxonomy *Enterobacter cowanii*.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein said endophyte is of the taxonomy *Enterobacter cowanii*.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein said endophyte is of the taxonomy *Enterobacter cowanii*.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein said endophyte is of the taxonomy *Enterobacter cowanii*.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the plant element is of the genus *Oryza* and the improve trait of agronomic importance is dry root biomass.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein said improved trait of agronomic importance is conferred under normal watering conditions.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein said improved trait of agronomic importance is conferred under normal watering conditions.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the plant element is a seed.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the plant element is a seed.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the plant element is a seed.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the plant element is a seed.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the plant element is a seed.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the plant element is a seed.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the plant element is a seed, wherein the seed is modified.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the plant element is a seed, wherein the seed is modified.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the plant element is a seed, wherein the seed is modified.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the plant element is a seed, wherein the seed is modified.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the synthetic composition is placed into a substrate that promotes plant growth.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the synthetic composition is placed into a substrate that promotes plant growth.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the synthetic composition is placed into a substrate that promotes plant growth.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the synthetic composition is placed into a substrate that promotes plant growth.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the synthetic composition is placed into a substrate that promotes plant growth, wherein the substrate that promotes plant growth is soil, wherein a plurality of said plant elements are placed in the soil in rows, with substantially equal spacing between each seed within each row.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, the synthetic composition further comprising a formulation that comprises one or more of the following: stabilizer, preservative, carrier, surfactant, anticomplex agent, or any combination thereof.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, the synthetic composition further comprising a formulation that comprises one or more of the following: fungicide, nematicide, bactericide, insecticide, or herbicide.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein said compositions are confined within an object selected from the group consisting of: bottle, jar, ampule, package, vessel, bag, box, bin, envelope, carton, container, silo, shipping container, truck bed, or case.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Periconia* as deposited under NRRL Culture Deposit No. 67466, wherein the synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a modified endophyte of the genus *Periconia* derived from the endophyte as deposited under NRRL Culture Deposit No. 67466, wherein the synthetic composition is capable of providing an improved trait of agronomic importance as compared to a reference plant element not further comprising the modified endophyte, wherein the synthetic combinations are shelf-stable.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Curvularia* as deposited under NRRL Culture Deposit No. 67467, wherein the synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a modified endophyte of the genus *Curvularia* derived from the endophyte as deposited under NRRL Culture Deposit No. 67467, wherein the synthetic composition is capable of providing an improved trait of agronomic importance as compared to a reference plant element not further comprising the modified endophyte, wherein the synthetic combinations are shelf-stable.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a member of the genus *Enterobacter* as deposited under NRRL Culture Deposit No. B67465, wherein the synthetic composition is capable of providing an improved trait of agronomic importance as compared to a reference plant element not further comprising the endophyte, wherein the synthetic combinations are shelf-stable.

In one aspect, the invention provides a synthetic composition comprising a plant element and a heterologously disposed endophyte, wherein the endophyte is a modified endophyte of the genus *Enterobacter* derived from the endophyte as deposited under NRRL Culture Deposit No. B67465, wherein the synthetic composition is capable of providing an improved trait of agronomic importance as compared to a reference plant element not further comprising the modified endophyte, wherein the synthetic combinations are shelf-stable.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is at least 98%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is at least 98%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is at least 98%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is at least 98%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is at least 98%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is at least 98%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is at least 98%.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is at least 98%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is at least 98%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is at least 98%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is at least 98%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is at least 98%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is at least 98%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is at least 98%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is at least 98%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is at least 98%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is at least 98%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is at least 98%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is at least 98%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is at least 98%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is at least 99%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is at least 99%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is at least 99%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is at least 99%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is at least 99%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is at least 99%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is at least 99%.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is at least 99%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is at least 99%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is at least 99%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is at least 99%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is at least 99%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is at least 99%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is at least 99%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is at least 99%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is at least 99%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is at least 99%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is at least 99%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is at least 99%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is at least 99%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is 100%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is 100%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is 100%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is 100%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is 100%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is 100%.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is 100%.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is 100%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is 100%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is 100%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is 100%.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is 100%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is 100%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is 100%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is 100%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is 100%.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is 100%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is 100%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is 100%.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is 100%.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is determined over a region of alignment of at least 100 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is determined over a region of alignment of at least 100 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is determined over a region of alignment of at least 100 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is determined over a region of alignment of at least 100 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is determined over a region of alignment of at least 100 nucleotides.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is determined over a region of alignment of at least 100 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is determined over a region of alignment of at least 100 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is determined over a region of alignment of at least 100 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is determined over a region of alignment of at least 100 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is determined over a region of alignment of at least 100 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is determined over a region of alignment of at least 100 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is determined over a region of alignment of at least 100 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is determined over a region of alignment of at least 100 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is determined over a region of alignment of at least 100 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is determined over a region of alignment of at least 100 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is determined over a region of alignment of at least 200 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is determined over a region of alignment of at least 200 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is determined over a region of alignment of at least 200 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is determined over a region of alignment of at least 200 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is determined over a region of alignment of at least 200 nucleotides.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is determined over a region of alignment of at least 200 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is determined over a region of alignment of at least 200 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is determined over a region of alignment of at least 200 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is determined over a region of alignment of at least 200 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is determined over a region of alignment of at least 200 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is determined over a region of alignment of at least 200 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is determined over a region of alignment of at least 200 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is determined over a region of alignment of at least 200 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is determined over a region of alignment of at least 200 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is determined over a region of alignment of at least 200 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is determined over a region of alignment of at least 300 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is determined over a region of alignment of at least 300 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is determined over a region of alignment of at least 300 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is determined over a region of alignment of at least 300 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is determined over a region of alignment of at least 300 nucleotides.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is determined over a region of alignment of at least 300 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is determined over a region of alignment of at least 300 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is determined over a region of alignment of at least 300 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is determined over a region of alignment of at least 300 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is determined over a region of alignment of at least 300 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is determined over a region of alignment of at least 300 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is determined over a region of alignment of at least 300 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is determined over a region of alignment of at least 300 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is determined over a region of alignment of at least 300 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is determined over a region of alignment of at least 300 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is determined over a region of alignment of at least 400 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is determined over a region of alignment of at least 400 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is determined over a region of alignment of at least 400 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is determined over a region of alignment of at least 400 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is determined over a region of alignment of at least 400 nucleotides.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is determined over a region of alignment of at least 400 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is determined over a region of alignment of at least 400 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is determined over a region of alignment of at least 400 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is determined over a region of alignment of at least 400 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is determined over a region of alignment of at least 400 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is determined over a region of alignment of at least 400 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is determined over a region of alignment of at least 400 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is determined over a region of alignment of at least 400 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is determined over a region of alignment of at least 400 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is determined over a region of alignment of at least 400 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Periconia* and comprises at least one polynucleotide sequence at least 97% identical to a sequence selected from the group consisting of SEQ ID NO: 32 and 33, wherein said synthetic composition is capable of providing an improved trait of agronomic importance as compared to reference plant element not further comprising the endophyte, wherein the endophyte comprises polynucleotide sequences at least 97% identical to each of the sequences in the group consisting of SEQ ID NO: 32 and 33, wherein the percent identity is determined over a region of alignment of at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 34-38, wherein the percent identity is determined over a region of alignment of at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 34-38, wherein the percent identity is determined over a region of alignment of at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 34-38, wherein the percent identity is determined over a region of alignment of at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97% identical to a sequence selected from the group consisting of SEQ ID NOs: 34-38, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 34-38, wherein the percent identity is determined over a region of alignment of at least 500 nucleotides.

In one aspect, the invention provides a synthetic composition comprising a plant element and a heterologously disposed endophyte, wherein the endophyte is a member of the genus *Asperigullus* and comprises at least one polynucleotide sequence at least 97% identical to SEQ ID NO. 39, wherein the synthetic composition is capable of providing an improved trait of agronomic importance as compared to reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID Nos: 40-43, wherein the percent identity is determined over a region of alignment of at least 500 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID Nos: 40-43, wherein the percent identity is determined over a region of alignment of at least 500 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a sequence selected from the group consisting of SEQ ID NOs: 40-43, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID Nos: 40-43, wherein the percent identity is determined over a region of alignment of at least 500 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 44-48, wherein the percent identity is determined over a region of alignment of at least 500 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 44-48, wherein the percent identity is determined over a region of alignment of at least 500 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least four sequences selected from the group consisting of SEQ ID NOs: 44-48, wherein the percent identity is determined over a region of alignment of at least 500 nucleotides.

In one aspect, the invention provides a synthetic composition comprising a plant element and a heterologously disposed endophyte, wherein the endophyte is a member of the genus *Pestalotiopsis* and comprises at least one polynucleotide sequence at least 97% identical to a sequence selected from the group consisting of SEQ ID NOs: 44-48, wherein said synthetic composition is capable of providing an improved trait of agronomic importance as compared to a reference plant element not further comprising the endophyte, wherein the endophyte comprises polynucleotide sequences at least 97% identical to at least five sequences selected from the group consisting of SEQ ID NOs: 44-48, wherein the percent identity is determined over a region of alignment of at least 500 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the percent identity is determined over a region of alignment of at least 500 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least two sequences selected from the group consisting of SEQ ID NOs: 49-51, wherein the percent identity is determined over a region of alignment of at least 500 nucleotides.

In one aspect, the invention provides a synthetic composition comprising a plant element and a heterologously disposed endophyte, wherein the endophyte is a member of the genus *Enterobacter* and comprises at least one polynucleotide sequence at least 97% identical to a sequence selected from the group consisting of SEQ ID NOs: 49-51, wherein said synthetic composition is capable of providing an improved trait of agronomic importance as compared to a reference plant element not further comprising the endophyte, wherein the endophyte comprises polynucleotide sequences at least 97% identical to at least three sequences selected from the group consisting of SEQ ID NOs: 49-51, wherein the percent identity is determined over a region of alignment of at least 500 nucleotides.

DETAILED DESCRIPTION

Figure 1:
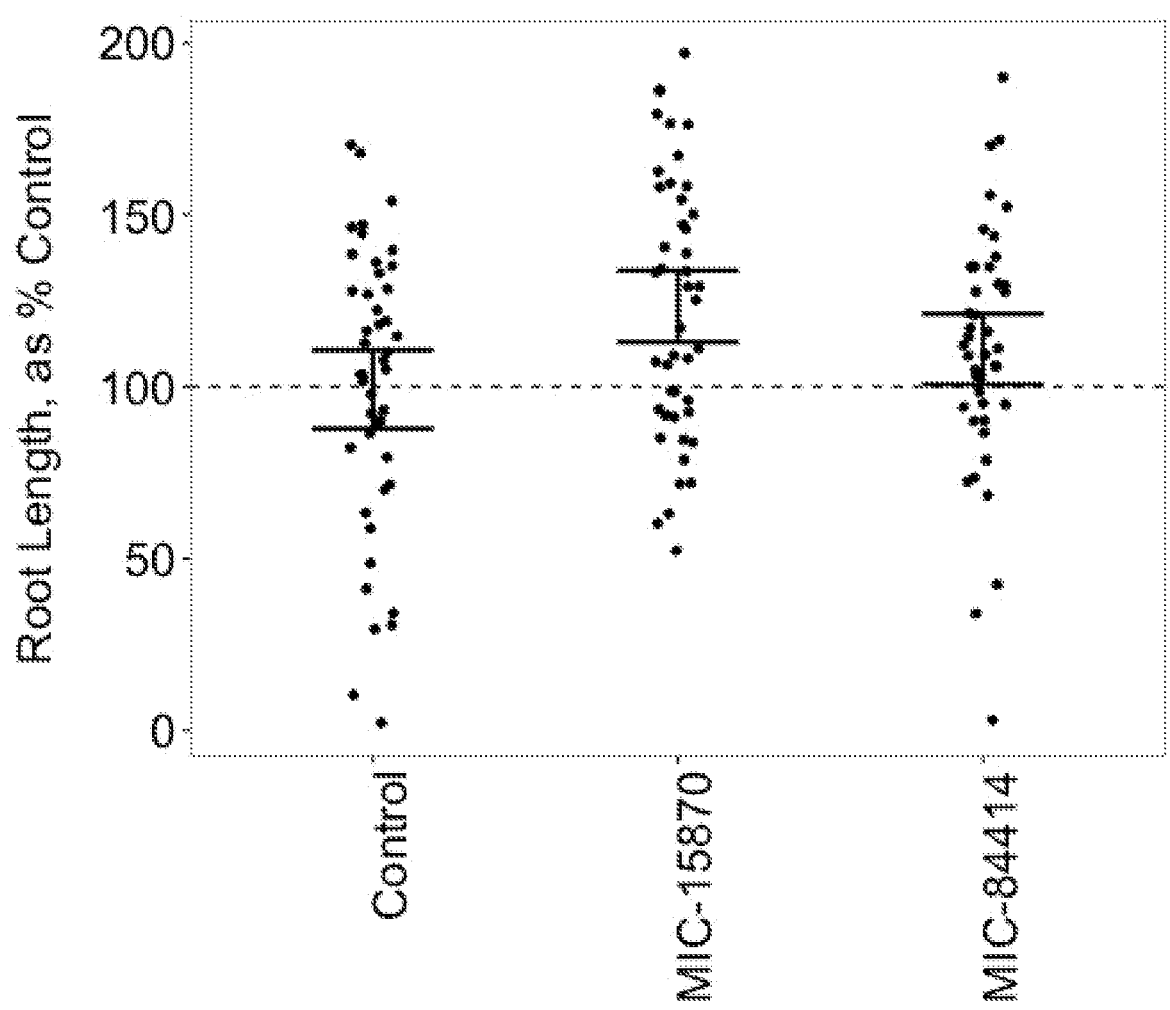
FIG. 1: Root length (cm) of soybean seedlings as percentage of the average root length of control soybean seedlings not treated with a microbe. Seedlings were grown as described in Example 4.
Figure 2:
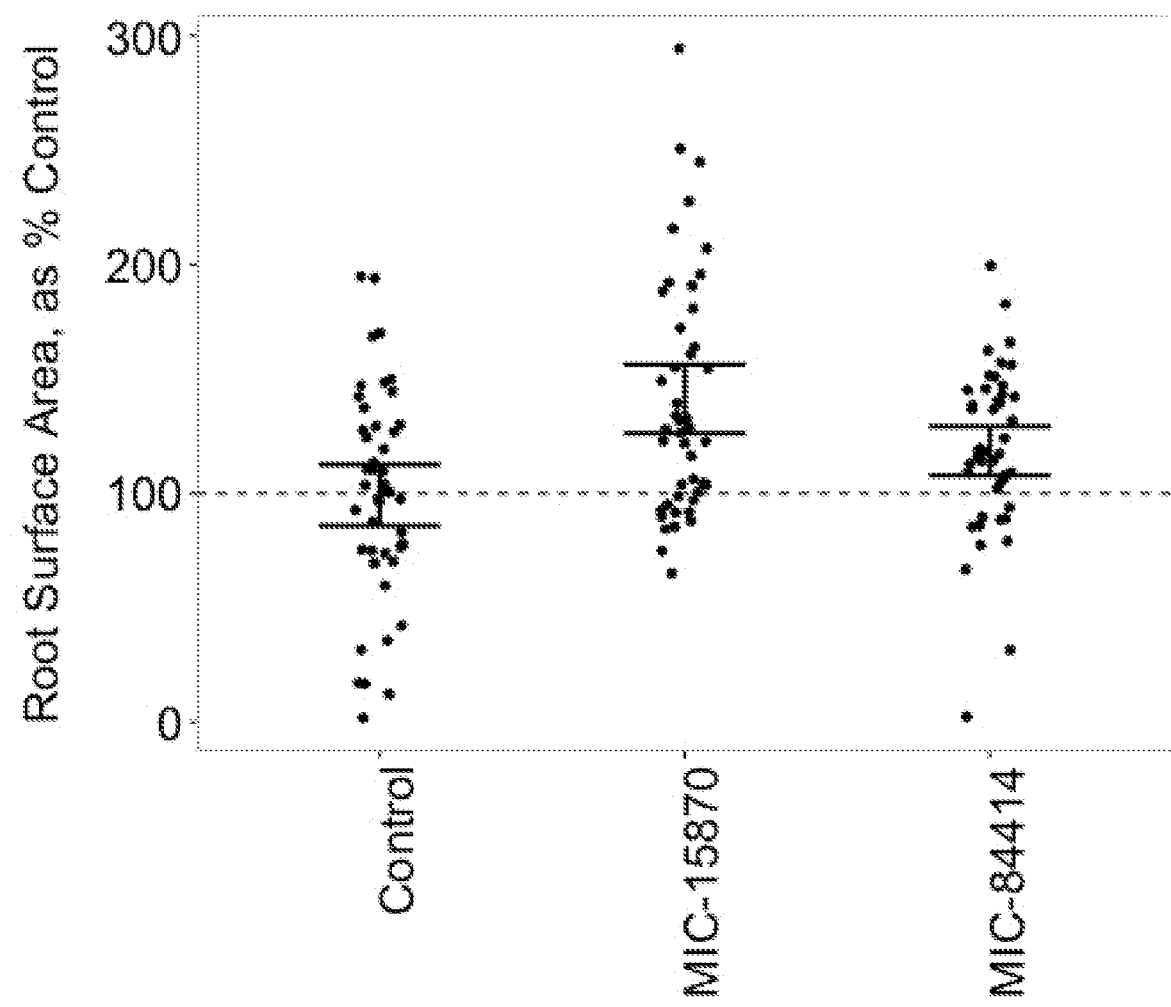
FIG. 2: Root surface area (cm²) of soybean seedlings as percentage of the average root surface area of soybean seedlings not treated with a microbe. Seedlings were grown as described in Example 4.

As demonstrated herein, agricultural plants are heterologously disposed to symbiotic microorganisms, termed endophytes, particularly bacteria and fungi, which contribute to plant survival, performance, and characteristics.

Described herein are endophytes that are capable of living within or otherwise heterologously disposed to plants to improve plant characteristics. Described herein are methods of using endophytes that are heterologously disposed to plants to impart novel characteristics to a host plant, as well as to distinct plant elements of the host plant. In some embodiments, endophyte compositions are isolated and purified from plant or fungal sources, and heterologously disposed with a plant element to impart improved agronomic potential and/or improved agronomic traits to the host plant. In some embodiments, endophytes that are capable of living within plants are isolated and purified from their native source(s) and heterologously disposed, e.g., manually, mechanically, or artificially combined, with a plant element, to impart improved agronomic potential and/or improved agronomic traits to the host plant or the host plant's elements. Such endophytes that are capable of living within plants may be further manipulated or combined with additional elements prior to combining with the plant element(s).

As described herein, endophytes can be robustly derived from heterologous, homologous, or engineered sources, optionally cultured, manually, mechanically or artificially applied heterologously to plant elements, e.g., heterologously disposed, and, as a result of the manual, mechanical or artificial application, confer multiple beneficial properties. This is surprising given the variability observed in the art in endophytic microbe isolation and the previous observations of inefficient plant element pathogen colonization of plant host's tissues.

In part, the present invention provides preparations of endophytes that are capable of living within plants, and the creation of synthetic compositions of plant elements and/or seedlings with heterologously disposed endophytes, and formulations comprising the synthetic compositions, as well as the recognition that such synthetic compositions display a diversity of beneficial and unexpected properties present in the agricultural plants and/or the heterologous endophyte populations. Beneficial properties include, but are not limited to metabolism, transcript expression, proteome alterations, morphology, resilience to a variety of environmental stresses, and any combination of such properties. The present invention also provides methods of using endophytes described herein to benefit the host plant with which they are heterologously disposed.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

An "endophyte" is an organism capable of living on a plant element (e.g., rhizoplane or phylosphere) or within a plant element, or on a surface in close physical proximity with a plant element, e.g., the rhizosphere, or e.g., on a seed. A "beneficial" endophytes does not cause disease or harm the host plant otherwise. Endophytes can occupy the intracellular or extracellular spaces of plant tissue, including the leaves, stems, flowers, fruits, seeds, or roots. An endophyte can be, for example, a bacterial or fungal organism, and can confer a beneficial property to the host plant such as an increase in yield, biomass, resistance, or fitness. An endophyte can be a fungus or a bacterium. As used herein, the term "microbe" is sometimes used to describe an endophyte.

A "population" of endophytes, or an "endophyte population", refers to one or more endophytes that share a common genetic derivation, e.g., one or more propagules of a single endophyte, i.e., endophytes grown from a single picked colony. In some embodiments, a population refers to endophytes of identical taxonomy. In some cases, a population of endophytes refers to one or more endophytes of the same genus. In some cases, a population of endophytes refers to one or more endophytes of the same OTU.

A "plurality of endophytes" means two or more types of endophyte entities, e.g., of bacteria or fungi, or combinations thereof. In some embodiments, the two or more types of endophyte entities are two or more individual endophytic organisms, regardless of genetic derivation or taxonomic relationship. In some embodiments, the two or more types of endophyte entities are two or more populations of endophytes. In other embodiments, the two or more types of endophyte entities are two or more species of endophytes. In yet other embodiments, the two or more types of endophyte entities are two or more genera of endophytes. In yet other embodiments, the two or more types of endophyte entities are two or more families of endophytes. In yet other embodiments, the two or more types of endophyte entities are two or more orders of endophytes. In yet other embodiments, the two or more types of endophyte entities are two or more classes of endophytes. In yet other embodiments, the two or more types of endophyte entities are two or more phyla of endophytes. In some embodiments, a plurality refers to three or more endophytes, either distinct individual organisms or distinct members of different genetic derivation or taxa. In some embodiments, a plurality refers to four or more either distinct individual endophytic organisms or distinct members of different genetic derivation or taxa. In some embodiments, a plurality refers to five or more, ten or more, or an even greater number of either distinct individual endophytic organisms or distinct members of different genetic derivation or taxa. In some embodiments, the term "consortium" or "consortia" may be used as a collective noun synonymous with "plurality", when describing more than one population, species, genus, family, order, class, or phylum of endophytes.

As used herein, the term "microbe" or "microorganism" refers to any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism is an endophyte, for example a bacterial or fungal endophyte, which is capable of living within a plant. In some embodiments, a microbe or microorganism encompasses individual cells (e.g., unicellular microorganisms) or more than one cell (e.g., multi-cellular microorganism). A "population of microorganisms" may thus refer to multiple cells of a single microorganism, in which the cells share common genetic derivation.

As used herein, the term "bacterium" or "bacteria" refers in general to any prokaryotic organism, and may reference an organism from either Kingdom Eubacteria (Bacteria), Kingdom Archaebacteria (Archae), or both. In some cases, bacterial genera have been reassigned due to various reasons (such as, but not limited to, the evolving field of whole genome sequencing), and it is understood that such nomenclature reassignments are within the scope of any claimed genus. For example, certain species of the genus *Erwinia* have been described in the literature as belonging to genus *Pantoea* (Zhang, Y. & Qiu, S. Antonie van Leeuwenhoek (2015) 108: 1037).

The term 16S refers to the DNA sequence of the 16S ribosomal RNA (rRNA) sequence of a bacterium. 16S rRNA gene sequencing is a well-established method for studying phylogeny and taxonomy of bacteria.

As used herein, the term "fungus" or "fungi" refers in general to any organism from Kingdom Fungi. Historical taxonomic classification of fungi has been according to morphological presentation. Beginning in the mid-1800's, it was recognized that some fungi have a pleomorphic life cycle, and that different nomenclature designations were being used for different forms of the same fungus. In 1981, the Sydney Congress of the International Mycological Association laid out rules for the naming of fungi according to their status as anamorph, teleomorph, or holomorph (Taylor J W. One Fungus=One Name: DNA and fungal nomenclature twenty years after PCR. IMA Fungus 2(2):113-120. 2011.). With the development of genomic sequencing, it became evident that taxonomic classification based on molecular phylogenetics did not align with morphological-based nomenclature (Shenoy B D, Jeewon R, Hyde K D. Impact of DNA sequence-data on the taxonomy of anamorphic fungi. Fungal Diversity 26(10) 1-54. 2007). As a result, in 2011 the International Botanical Congress adopted a resolution approving the International Code of Nomenclature for Algae, Fungi, and Plants (Melbourne Code) (International Code of Nomenclature for algae, fungi, and plants (Melbourne Code), adopted by the Eighteenth International Botanical Congress Melbourne, Australia, July 2011), with the stated outcome of designating "One Fungus=One Name" (Hawksworth DL. Managing and coping with names of pleomorphic fungi in a period of transition. IMA Fungus 3(1):15-24. 2012.). However, systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. For example, the genus *Alternaria* is the anamorph form of the teleomorph genus *Lewia* (Kwasna H and Kosiak B. *Lewia avenicola* sp. *nov.* and its *Alternaria* anamorph from oat grain, with a key to the species of *Lewia*. Mycol Res 2003; 107(Pt 3):371-6.), ergo both would be understood to be the same organism with the same DNA sequence. For example, it is understood that the genus *Acremonium* is also reported in the literature as genus *Sarocladium* as well as genus *Tilachilidium* (Summerbell R. C., C. Gueidan, H-J. Schroers3, G. S. de Hoog, M. Starink, Y. Arocha Rosete, J. Guano and J.A. Scott. *Acremonium* phylogenetic overview and revision of *Gliomastix, Sarocladium*, and *Trichothecium*. Studies in Mycology 68: 139-162. 2011.). For example, the genus *Cladosporium* is an anamorph of the teleomorph genus *Davidiella* (Bensch K, Braun U, Groenewald J Z, Crous P W. The genus *Cladosporium*. Stud Mycol. 2012 Jun. 15; 72(1): 1-401.), and is understood to describe the same organism. In some cases, fungal genera have been reassigned due to various reasons, and it is understood that such nomenclature reassignments are within the scope of any claimed genus.

"Internal Transcribed Spacer" (ITS) refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" (LSU) sequence is used to identify fungi. LSU gene sequencing is a well-established method for studying phylogeny and taxonomy of fungi. Some fungal endophytes may be described by an ITS sequence and some may be described by an LSU sequence. Both are understood to be equally descriptive and accurate for determining taxonomy.

As used herein with respect to fungi and bacteria, the term "marker gene" refers to a conserved gene comprising sequence variation among related organisms, e.g. an organism's 16S (for bacteria) or ITS (for fungi) polynucleotide sequence, fusA gene, or unique genomic regions, by which a microbe may be specifically identified and assigned taxonomic nomenclature. In some embodiments, marker genes include, but are not limited to, long subunit rRNA gene (LSU), second largest subunit of RNA polymerase II (RPB2), small subunit rRNA gene (SSU), 60S ribosomal protein L 10, beta-tubulin, and combinations thereof.

The terms "pathogen" and "pathogenic" in reference to a bacterium or fungus includes any such organism that is capable of causing or affecting a disease, disorder or condition of a host comprising the organism.

A "spore" or a population of "spores" refers to bacteria or fungi that are generally viable, more resistant to environmental influences such as heat and bactericidal or fungicidal agents than other forms of the same bacteria or fungi, and typically capable of germination and out-growth. Bacteria and fungi that are "capable of forming spores" are those bacteria and fungi comprising the genes and other necessary abilities to produce spores under suitable environmental conditions.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "isolated" is intended to specifically reference an organism, cell, tissue, polynucleotide, or polypeptide that is removed from its original source.

As used herein, an isolated endophyte or microbe is an endophyte or microbe that has been removed from its natural milieu. "Pure cultures" or "isolated cultures" are cultures in which the organisms present are only of one particular genus and species. This is in contrast to "mixed cultures," which are cultures in which more than one genus and/or species of microorganism are present. As such, the term "isolated" does not necessarily reflect the extent to which the microbe has been purified. A "substantially pure culture" of the microbe refers to a culture which contains substantially no other endophytes or microbes than the desired endophyte or microbe. In other words, a substantially pure endophyte or microbe culture is substantially free of other contaminants, which can include microbial contaminants. Further, as used herein, "biologically pure" is intended to mean the endophyte or microbe separated from materials with which it is normally found in nature. A microbe or endophyte heterologously disposed to other microbes or endophytes, or with compounds or materials that it is not normally found with in nature, is still defined as "biologically pure." A monoculture is, of course, "biologically pure." As used herein, the term "enriched culture" of an isolated microbe or endophyte refers to a culture that contains more that 50%, 60%, 70%, 80%, 90%, or 95% of the isolated endophyte or microbe.

A "host plant" includes any plant, particularly a plant of agronomic importance, within which or onto which a microbe, such as an endophyte, is heterologously disposed. As used herein, a microbe is said to colonize a plant, plant element, or seed, when it can exist as an endophyte in relationship with a plant or plant element during at least part of either the plant's or the microbe's life cycle. In some embodiments, an endophyte is said to "colonize" a plant or plant element when it can be stably detected within the plant or plant element over a period time, such as one or more days, weeks, months or years. Some of the compositions and methods described herein involve a plurality of microbes in an amount effective to colonize a plant.

A "non-host target" means an organism or chemical compound that is altered in some way after contacting a host plant that comprises an endophyte, as a result of a property conferred to the host plant by the endophyte.

As used herein, a nucleic acid has "homology" or is "homologous" to a second nucleic acid if the nucleic acid sequence has a similar sequence to the second nucleic acid sequence. The terms "identity", "percent identity", "percent sequence identity" or "identical" in the context of nucleic acid sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm (Needleman, S. B. & Wunsch, C. D. (1970) Journal of Molecular Biology. 48(3): 443-53). For example, a local alignment may be generated using an implementation of the Smith-Waterman algorithm (Smith T. F & Waterman, M. S. (1981) Journal of Molecular Biology. 147(1):195-197). Optimal global alignments using the Needleman-Wunsch algorithm and optimal local alignments using the Smith-Waterman algorithm are implemented in USEARCH, for example USEARCH version v8.1.1756_i86osx32.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment. An internal gap is a gap in an alignment which is flanked on the 3' and 5' end by positions wherein the aligned sequences are identical.

In some embodiments, the nucleic acid sequence to be aligned is a complete gene. In some embodiments, the nucleic acid sequence to be aligned is a gene fragment. In some embodiments, the nucleic acid sequence to be aligned is an intergenic sequence. In a preferred embodiment, inference of homology from a sequence alignment is make where the region of alignment is at least 85% of the length of the query sequence.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, at least 97%, 98%, 99% or 100% of the positions of the alignment, wherein the region of alignment is at least about 50%, 60%, 70%, 75%, 85%, or at least about 90%, or at least about 95%, 96%, 97%, 98%, 99% or 100% of the length of the query sequence. In a preferred embodiment, the region of alignment contains at least 100 positions inclusive of any internal gaps. In some embodiments, the region of alignment comprises at least 100 nucleotides of the query sequence. In some embodiments, the region of alignment comprises at least 200 nucleotides of the query sequence. In some embodiments, the region of alignment comprises at least 300 nucleotides of the query sequence. In some embodiments, the region of alignment comprises at least 400 nucleotides of the query sequence. In some embodiments, the region of alignment comprises at least 500 nucleotides of the query sequence. In some embodiments, the query sequence is selected from the group consisting of SEQ ID NOs 32-51.

As used herein, the terms "operational taxonomic unit," "OTU," "taxon," "hierarchical cluster," and "cluster" are used interchangeably. An operational taxon unit (OTU) refers to a group of one or more organisms that comprises a node in a clustering tree. The level of a cluster is determined by its hierarchical order. In some embodiments, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, OTUs can represent one or more organisms from the kingdoms Eubacteria, Bacteria, Protista, or Fungi, at any level of a hierarchical order. In some embodiments, an OTU represents a prokaryotic or fungal order.

In some embodiments, the present invention contemplates the synthetic compositions comprising the combination of a plant element, seedling, or whole plants and an endophyte population, in which the endophyte population is "heterologously disposed". In some embodiments, one or more endophytes of the synthetic composition are heterologously disposed when they are mechanically or manually applied, artificially inoculated or disposed onto or into a plant element, seedling, plant or onto or into a plant growth medium or onto or into a treatment formulation so that the endophyte exists on or in said plant element, seedling, plant, plant growth medium, or treatment formulation in a manner not found in nature prior to the application of one or more endophytes, e.g., said combination which is not found in nature. In some embodiments, such a manner is contemplated to be selected from the group consisting of: the presence of the endophyte; presence of the endophyte in a different number of cells, concentration, or amount; the presence of the endophyte in a different plant element, tissue, cell type, or other physical location in or on the plant; the presence of the endophyte at different time period, e.g. developmental phase of the plant or plant element, time of day, time of season, and combinations thereof. In some embodiments, one or more endophytes of a synthetic composition are heterologously disposed when the one or more endophytes are artificially inoculated, e.g., is manually or mechanically inoculated, or artificially applied, e.g. manually or mechanically applied, to a different plant element or at a different developmental stage than that with which the one or more endophytes are naturally found or at a greater concentration, number, or amount than that which is naturally found in or on said plant element, seedling, or plant. In some embodiments, "heterologously disposed" refers to the relationship between the endophyte and the inoculated host plant as compared to the type of host plant with which said endophyte is normally associated. In one example, endophytes used in a synthetic composition can be obtained from a different individual plant of the same variety as that of the host inoculated plant to which it becomes heterologously disposed, a plant of a different variety but the same genus and species, a plant of a different cultivar, or a plant of a different genus. In an embodiment, the endophyte is an endophytic microbe isolated from a different plant than the inoculated plant. For example, in an embodiment, the endophyte is an endophyte isolated from a different plant of the same species as the inoculated plant. In some cases, the endophyte is isolated from a species related to the inoculated plant. In another example, endophytes used in a synthetic composition can be obtained from different individual plants of the same variety, each of which has been subjected to different growth conditions. For example, an endophyte derived from a drought-affected plant of one variety can be isolated and coated onto the plant element that was derived from a plant of the same variety not subjected to drought. In such cases, the endophyte is considered to be heterologously disposed to the plant element onto which it is manually, mechanically, or artificially applied. In some embodiments, "heterologously disposed" means that the endophyte applied to a different tissue or cell type of the plant element than that in which the microbe is naturally found. In some embodiments, an endophyte is heterologously disposed on a seedling if that endophyte is normally found at the flowering stage of a plant and not at a seedling stage. In some embodiments, an endophyte is heterologously disposed the endophyte is normally found in the root tissue of a plant element but not in the leaf tissue, and the endophyte is applied to the leaf. In yet another non-limiting example, if an endophyte is naturally found in the mesophyll layer of leaf tissue but is being applied to the epithelial layer, the endophyte would be considered to be heterologously disposed. In some embodiments, "heterologously disposed" means that the native plant element, seedling, or plant does not contain detectable levels of the microbe in that same plant element, seedling, or plant. For example, if said plant element or seedling or plant does not naturally have the endophyte heterologously disposed to it and the endophyte is applied, the endophyte would be considered to be heterologously disposed. In some embodiments, "heterologously disposed" means that the endophyte being applied is at a greater concentration, number, or amount to the plant element, seedling, or plant, than that which is naturally found in said plant element, seedling, or plant. For example, an endophyte is heterologously disposed when present at a concentration that is at least 1.5 times greater, between 1.5 and 2 times greater, 2 times greater, between 2 and 3 times greater, 3 times greater, between 3 and 5 times greater, 5 times greater, between 5 and 7 times greater, 7 times greater, between 7 and 10 times greater, 10 times greater, or even greater than 10 times higher number, amount, or concentration than the concentration that was present prior to the disposition of said endophyte. In some embodiments, "heterologously disposed" means that the endophyte is applied to a developmental stage of the plant element, seedling, or plant in which said endophyte is not naturally found, but may be associated at other stages. In some embodiments, "heterologously disposed" means that the endophyte was isolated from plants or plant elements under an environmental condition different than that which is normally found (for example but not limited to: different soil pH, different mean air temperature, different soil temperature, different rainfall conditions, different soil nutrient composition, or different environmental salinity). In one example, if an endophyte is normally found at the flowering stage of a plant and no other stage, an endophyte applied at the seedling stage may be considered to be heterologously disposed. In another example, an endophyte that is normally heterologously disposed to leaf tissue of a plant is considered heterologous to a leaf tissue of another plant that naturally lacks said endophyte. In another example, an endophyte that is normally found at low levels in a plant is considered heterologous to that plant if a higher concentration of that endophyte is introduced into the plant. In yet another example, an endophyte that is heterologously disposed to a tropical grass species would be considered heterologous to a different grass species that naturally lacks said endophyte.

An "inoculated" plant or plant element has been artificially introduced to a heterologous endophyte at some point during the plant's or plant element's growth or development (including vegetative or reproductive phases). In some embodiments, the heterologous endophyte is transiently or permanently incorporated into the plant or plant element, and is detectable using methods known in the art or described herein. In some embodiments, a seed is inoculated with an endophyte by manually or mechanically contacting the seed with a formulation comprising said endophyte, which is detectable in or on the seed. In some embodiments, a plant is said to be inoculated with an endophyte if it is grown from a reproductive element (e.g. a seed) that was itself manually or mechanically contacted with a formulation comprising said endophyte, which is subsequently detectable in or on the plant. In some embodiments, a plant is said to be inoculated with an endophyte if any one or more if its plant elements (e.g., leaf, stem, or root) is manually or mechanically contacted with a formulation comprising said endophyte, which is subsequently detectable either in the same plant element that was originally contacted with said formulation or in a different plant element of that plant. The term "inoculation" may also refer to the manual or mechanical contact of an endophyte population to any substance, that is detectable in or on said substance subsequent to endophyte contact. In one example, said substance is soil or other plant growth medium. In another example, said substance is a storage medium such as glycerol. In some cases, "inoculation" may refer to the contact of an endophyte population to a non-plant living organism, for example, but not limited to, an insect or a fungus.

The term "isoline" is a comparative term, and references organisms that are genetically identical, but may differ in treatment. In one example, two genetically identical maize plant embryos may be separated into two different groups, one receiving a treatment (such as transformation with a heterologous polynucleotide, to create a genetically modified plant) and one control, e.g., reference, that does not receive such treatment. Any phenotypic differences between the two groups may thus be attributed solely to the treatment and not to any inherency of the plant's genetic makeup. In another example, two genetically identical soybean seeds may be treated with a formulation, one that introduces an endophyte composition and one that does not. Any phenotypic differences between the plants derived from (e.g., grown from or obtained from) those seeds may be attributed to the endophyte treatment, thus forming an isoline comparison.

Similarly, by the term "reference agricultural plant," it is meant an agricultural plant of the same species, variety, or cultivar to which a treatment, formulation, composition or endophyte preparation as described herein is not administered/contacted. A reference agricultural plant, therefore, is identical to the treated plant with the exception of the presence of the endophyte and can serve as a control for detecting the effects of the endophyte that is conferred to the plant. In some embodiments, the phrase "reference isoline plant" is used herein to describe a reference plant that is genetically identical and subject to the same conditions, i.e., a control plant, to the treated plant.

A "reference environment" refers to the environment, treatment or condition of the plant in which a measurement is made. For example, production of a compound in a plant heterologously disposed to an endophyte can be measured in a reference environment of drought stress, and compared with the levels of the compound in a reference agricultural plant under the same conditions of drought stress. Alternatively, the levels of a compound in plant heterologously disposed to an endophyte and reference agricultural plant can be measured under identical conditions of no stress.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, fruit, stolon, bulb, tuber, corm, keikis, shoot, bud. As used herein, a "plant element" is synonymous to a "portion" of a plant, and refers to any part of the plant, and can include distinct tissues and/or organs, and may be used interchangeably with the term "tissue" throughout.

Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keikis, or bud.

A "progeny seed", as used herein, refers to the seed produced by a host plant that has been inoculated with, or heterologously disposed to, an endophyte. For example, in the present invention, a seed, plant element, or whole plant may become heterologously disposed to an endophyte, and the plant that is grown from said seed, or plant that is grown in heterologous association with said endophyte, may itself produce progeny seeds that comprise altered nutritional composition compared to seeds obtained from plants that were not grown from a plant element heterologously disposed to an endophyte or obtained from a parental (host) plant that had become heterologously disposed to an endophyte at some point in its life cycle. In the general sense, the phrase "progeny seed" may be construed to represent any plant propagative unit produced by the host plant that is capable of becoming another individual of that same plant species.

A "population" of plants refers to more than one plant, that are of the same taxonomic category, typically be of the same species, and will also typically share a common genetic derivation.

As used herein, an "agricultural seed" is a seed used to grow a plant typically used in agriculture (an "agricultural plant"). The seed may be of a monocot plant, and may be planted for the production of an agricultural product, for example feed, food, fiber, fuel, industrial uses, etc. As used herein, an agricultural seed is a seed that is prepared for planting, for example, in farms for growing.

"Agricultural plants" or "plants of agronomic importance include plants that are cultivated by humans for food, feed, fiber, fuel, and/or industrial purposes. In some embodiments, plants (including seeds and other plant elements) treated in accordance with the present invention are monocots. In some embodiments, plants (including seeds or other plant elements) treated in accordance with the present invention are dicots. In some embodiments, plants treated in accordance with the present invention include, but are not limited to: agricultural row, agricultural grass plants or other field crops: wheat, rice, barley, buckwheat, beans (soybean, snap, dry), corn (grain, seed, sweet corn, silage, popcorn, high oil), cotton, canola, peas (dry, succulent), peanuts, safflower, sunflower, alfalfa hay, forage crops (alfalfa, clover, vetch, and trefoil), berries and small fruits (blackberries, blueberries, currants, elderberries, gooseberries, huckleberries, loganberries, raspberries, strawberries, bananas and grapes), bulb crops (garlic, leeks, onions, shallots, and ornamental bulbs), citrus fruits (citrus hybrids, grapefruit, kumquat, lines, oranges, and pummelos), cucurbit vegetables (cucumbers, melons, gourds, pumpkins, and squash), flowers, bedding plants, ornamentals, fruiting vegetables (eggplant, sweet and hot peppers, tomatillos, and tomatoes), herbs, spices, mints, hydroponic crops (cucumbers, tomatoes, lettuce, herbs, and spices), leafy vegetables and cole crops (arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, and mustard greens), asparagus, legume vegetable and field crops (snap and dry beans, lentils, succulent and dry peas, and peanuts), pome fruit (pears and quince), root crops (beets, sugarbeets, red beets, carrots, celeriac, chicory, horseradish, parsnip, radish rutabaga, salsify, and turnips), deciduous trees (maple and oak), pine, small grains (rye, wheat, sorghum, millet), stone fruits (apricots, cherries, nectarines, peaches, plums, and prunes), tree nuts (almonds, beech nuts, Brazil nuts, butternuts, cashews, chestnuts, filberts, hickory nuts, macadamia nuts, pecans, pistachios, and walnuts), and tuber crops (potatoes, sweet potatoes, yams, artichoke, cassava, and ginger). In a particular embodiment, the agricultural plant is selected from the group consisting of rice (*Oryza sativa* and related varieties), soy (*Glycine max* and related varieties), wheat (*Triticum aestivum* and related varieties), corn (*Zea mays* and related varieties), peanuts (*Arachis hypogaea* and related varieties), canola (*Brassica napus, Brassica rapa* and related varieties), sorghum (*Sorghum bicolor* and related varieties), coffee (*Coffea* spp.), cocoa (*Theobroma cacao*), melons, and tomatoes (*Solanum lycopsersicum* and related varieties).

A "closely related variety" comprises a common genetic derivation with a plant variety. In some embodiments, a closely related variety has at least one grandparental line in common with the plant variety. In some embodiments, a closely related variety has at least one parental line in common with the plant variety. In some embodiments, a closely related variety has at least 60%, 70%, 80%, 90%, 91%, 92%, 93%, 94%, 95%, 96%, 97%, 98%, 99%, 99.5%, 99.7%, 99.9%, 99.99% of the same SNPs detected in the plant variety. In some embodiments, a closely related variety has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or 20 or more of the same SNPs detected in the plant variety. In some embodiments, a closely related variety has at least 20, at least 30, at least 40, at least 50, at least 60, at least 70, at least 80, at least 90, at least 100, at least 200, at least 300, at least 400, at least 500, at least 600, at least 700, at least 800, at least 900, or 100 or more of the same SNPs detected in the plant variety. In some embodiments, a closely related variety has at least 1000, at least 2000, at least 3000, at least 4000, at least 5000, at least 6000, at least 7000, at least 8000, at least 9000, or 10000 or more of the same SNPs detected in the plant variety. In some embodiments, a closely related variety has at least 10000, at least 20000, at least 30000, at least 40000, at least 50000, at least 60000, at least 70000, at least 80000, at least 90000, or 100000 or more of the same SNPs detected in the plant variety.

A "synthetic composition" comprises one or more endophytes combined by human endeavor with a heterologously disposed plant element or a treatment formulation, said combination which is not found in nature. In some embodiments, the term "synthetic composition" means one or more plant elements or formulation components combined by human endeavor with an isolated, purified endophyte composition. In some embodiments, said purified endophyte composition is mechanically or manually applied, artificially inoculated or disposed on a plant element in a manner that is not found on or in the plant element before application of the purified endophyte composition, e.g., said combination or association which is not found in nature.

In some embodiments, "synthetic composition" is used to refer to a treatment formulation comprising an isolated, purified population of endophytes heterologously disposed to a plant element. In some embodiments, "synthetic composition" refers to a purified population of endophytes in a treatment formulation comprising additional compositions with which said endophytes are not found in nature.

A "treatment formulation" refers to a mixture of chemicals that facilitate the stability, storage, and/or application of the endophyte composition(s). Treatment formulations may comprise any one or more agents such as: surfactant, a buffer, a tackifier, a microbial stabilizer, a fungicide, an anticomplex agent, an herbicide, a nematicide, an insecticide, a plant growth regulator, a rodenticide, a desiccant, a nutrient, an excipient, a wetting agent, a salt.

In some embodiments, an "agriculturally compatible carrier" can be used to formulate an agricultural formulation or other composition that includes a purified endophyte preparation. As used herein an "agriculturally compatible carrier" refers to any material, other than water, that can be added to a plant element without causing or having an adverse effect on the plant element (e.g., reducing seed germination) or the plant that grows from the plant element, or the like.

"Plant health" is demonstrated by the presence or improvement of a trait of agronomic importance found in a plant or plant element as compared to a reference plant or plant element. The compositions and methods herein may provide for an improved "agronomic trait" or "trait of agronomic importance" to a host plant, which include, but are not limited to disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, increased root area, improved root architecture, modulation of a metabolite, modulation of the proteome, increased seed weight, altered seed carbohydrate composition, altered seed oil composition, altered seed protein composition, altered seed nutrient composition, and combinations thereof, as compared to reference plant derived from a seed without said seed treatment formulation.

In some embodiments, a treatment is heterologously disposed on a plant element in an amount effective to improve a trait of agronomic importance. In some embodiments, treatments capable of improving plant health are applied in an amount effective to improve a trait of agronomic importance or tolerance by at least 0.1%, at least 0.5%, at least 1%, at least 2%, at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, as compared to a reference plant element not further comprising said endophyte.

In some embodiments, an improvement in a trait of agronomic importance is measured by the "win rate". The win rate is the proportion of replicates where the treatment shows an improvement in a trait of agronomic importance relative to reference replicates. In some embodiments, replicates are individual plants. In some embodiments, replicates are plots, e.g. replicated plots within a randomized complete block design field trial. In some embodiments, replicates are field trials conducted at diverse geographies.

In some embodiments, the endophyte is capable of improving a trait of agronomic importance at concentrations detected on or in the treated plant element of at least $10^2$ CFU or spores per plant element, between $10^2$ and $10^3$ CFU or spores per plant element, about $10^3$ CFU or spores per plant element, between $10^3$ and $10^4$ CFU or spores per plant element, about $10^4$ CFU or spores per plant element, or between $10^4$, of about $10^5$ CFU or spores per plant element, at least $10^5$ CFU or spores per plant element, between $10^5$ and $10^6$ CFU or spores per plant element, about $10^6$ CFU or spores per plant element, between $10^6$ and $10^7$ CFU or spores per plant element, about $10^7$ CFU or spores per plant element, between $10^7$ and $10^8$ CFU or spores per plant element, about $10^8$ CFU or spores per plant element, or even greater than $10^8$ CFU or spores per plant element. In some embodiments, the plant element is a seed.

The phrase "nutritional quality trait" includes any measurable parameter of a seed that either directly or indirectly influences the value (nutritional or economic) of said seed, for example, but not limited to: protein, fat, carbohydrate, ash, moisture, fiber, and calories. In some cases, "nutritional quality trait" is synonymous with "nutritional quality trait" or "seed nutritional quality trait", and can refer to any composition of the associated plant element, most particularly compositions providing benefit to other organisms that consume or utilize said plant element. As used herein, "oil" and "fat" are used interchangeably.

An increased "seed yield" can refer to any increase in seed or fruit weight, size, or abundance per a unit of measure, for example, per plant, per number of plants, per mass of plants, per acre planted, per acre harvested. In some embodiments, seed yield is reported as pounds or bushels of seed produced per acre harvested. The terms seed and grain are used interchangeably herein. Yield may also refer to the recovery of a particular component of a plant tissue upon processing, for example, the amount of oil which can be extracted per unit of seed. Typically, the particular characteristic is designated when referring to increased yield, e.g., increased seed yield or increased oil yield. Where the characteristic is not specified it may be assumed yield refers to seed yield and the terms may be used interchangeably.

As used herein, the terms "water-limited condition" and "drought condition," or "water-limited" and "drought," may be used interchangeably. For example, a method or composition for improving a plant's ability to grow under drought conditions means the same as the ability to grow under water-limited conditions. In such cases, the plant can be further said to display improved tolerance to drought stress.

As used herein, the terms "normal watering" and "well-watered" are used interchangeably, to describe a plant grown under typical growth conditions with no water restriction.

Additionally, "altered metabolic function" or "altered enzymatic function" may include, but not be limited to, the following: altered production of an auxin, altered nitrogen fixation, altered production of an antimicrobial compound, altered production of a siderophore, altered mineral phosphate solubilization, altered production of a cellulase, altered production of a chitinase, altered production of a xylanase, altered production of acetoin, altered utilization of a carbon source.

"Nutrient" or "seed nutrient" refers to any composition of the associated plant element, most particularly compositions providing benefit to other organisms that consume or utilize said plant element.

"Agronomic trait potential" is intended to mean a capability of a plant element for exhibiting a phenotype, preferably an improved agronomic trait, at some point during its life cycle, or conveying said phenotype to another plant element with which it is associated in the same plant. For example, a plant element may comprise an endophyte that will provide benefit to leaf tissue of a plant from which the plant element is grown; in such case, the plant element comprising such endophyte has the agronomic trait potential for a particular phenotype (for example, increased biomass in the plant) even if the plant element itself does not display said phenotype.

In some cases, the present invention contemplates the use of compositions that are "compatible" with agricultural chemicals, including but not limited to, a fungicide, an anti-complex compound, a bactericide, a virucide, an herbicide, a nematicide, a parasiticide, a pesticide, or any other agent widely used in agricultural which has the effect of killing or otherwise interfering with optimal growth of another organism. As used herein, a composition is "compatible" with an agricultural chemical when the organism is modified, such as by genetic modification, e.g., contains a transgene that confers resistance to an herbicide, or is adapted to grow in, or otherwise survive, the concentration of the agricultural chemical used in agriculture. For example, an endophyte disposed on the surface of a plant element is compatible with the fungicide metalaxyl if it is able to survive the concentrations that are applied on the plant element surface.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

The terms "decreased," "fewer," "slower" and "increased" "faster" "enhanced" "greater" as used herein refers to a decrease or increase in a characteristic of the endophyte treated plant element or resulting plant compared to an untreated plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

As used herein, a microbe or plant or plant element is "modified" when it comprises an artificially introduced genetic or epigenetic "modification". In some embodiments, the modification is introduced by a genome engineering technology. In some embodiments, the modification is introduced by a targeted nuclease. In some embodiments, targeted nucleases include, but are not limited to, transcription activator-like effector nuclease (TALEN), zinc finger nuclease (ZNF), clustered regulatory interspaced short palindromic repeats (CRISPR), CRISPR/Cas9, CRISPR/CPFL and combinations thereof. In some embodiments, the modification is an epigenetic modification. In some embodiments, the modification is introduced by treatment with a DNA methyltransferase inhibitor such as 5-azacytidine, or a histone deacetylase inhibitor such as 2-amino-7-methoxy-3H-phenoxazin-3-one. In some embodiments, the modification is introduced via tissue culture. In some embodiments, a modified microbe or plant or plant element comprises a transgene.

Endophyte Compositions

The endophytes described herein provide several unexpected and significant advantages to agricultural plants over other plant-associated microbes, as demonstrated in the Examples.

In some embodiments, the endophyte is selected from Table 4. In some embodiments, the endophyte is selected from Table 7.

In some embodiments, the endophyte comprises a polynucleotide sequence that is at least 97% identical to at least one sequence selected from the group consisting of SEQ ID NOs: 32 and 33. In some embodiments, the endophyte comprises a polynucleotide sequence that is between 97% and 98% identical, at least 98% identical, between 98.0% identical and 99.5% identical, or at least 99.5% identical, or 100% identical to at least one sequence selected from the group consisting of SEQ ID NOs: 32 and 33. In some embodiments, the endophyte comprises two polynucleotide sequence that are between 97% and 98% identical, at least 98% identical, between 98.0% identical and 99.5% identical, or at least 99.5% identical, or 100% identical to the sequences SEQ ID NOs: 32 and 33. In some embodiments, the endophyte is a *Periconia macrospinosa*. In some embodiments, the endophyte is deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-67466. In some embodiments, the endophyte is as deposited under NRRL Culture Deposit No. NRRL-67466, and thereafter modified. In some embodiments, the modified endophyte derived from the endophyte deposited as NRRL Culture Deposit No. NRRL-67466 retains the ability to modulate the nutrient composition of a seed produced by a plant element heterologously disposed with the modified endophyte.

In some embodiments, the endophyte comprises a polynucleotide sequence that is at least 97% identical to at least one sequence selected from the group consisting of SEQ ID NOs: 34, 35, 36, 37, and 38. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 34, 35, 36, 37, and 38. In some embodiments, the endophyte comprises at least two polynucleotide sequences that are at least 97% identical to at least two sequences selected from the group consisting of SEQ ID NOs: 34, 35, 36, 37, and 38. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 34, 35, 36, 37, and 38. In some embodiments, the endophyte comprises at least three polynucleotide sequences that are at least 97% identical to at least three sequences selected from the group consisting of SEQ ID NOs: 34, 35, 36, 37, and 38. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 34, 35, 36, 37, and 38. In some embodiments, the endophyte comprises at least four polynucleotide sequences that are at least 97% identical to at least four sequences selected from the group consisting of SEQ ID NOs: 34, 35, 36, 37, and 38. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 34, 35, 36, 37, and 38. In some embodiments, the endophyte comprises at least five polynucleotide sequences that are at least 97% identical to at least five sequences selected from the group consisting of SEQ ID NOs: 34, 35, 36, 37, and 38. In some embodiments, the endophyte comprises at least five polynucleotide sequences that are between 97% and 98% identical, at least 98% identical, between 98.0% identical and 99.5% identical, or at least 99.5% identical, or 100% identical to at least five sequences selected from the group consisting of SEQ ID NOs: 34, 35, 36, 37, and 38. In some embodiments, the endophyte is a *Curvularia spicifera*. In some embodiments, the endophyte is deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-67467. In some embodiments, the endophyte is an endophyte is deposited as NRRL Culture Deposit No. NRRL-67467 and thereafter modified. In some embodiments, the modified endophyte derived from the endophyte deposited as NRRL Culture Deposit No. NRRL-67467 retains the ability to modulate the nutrient composition of a seed produced by a plant element heterologously disposed with the modified endophyte.

In some embodiments, the endophyte comprises a polynucleotide sequence that is at least 97% identical SEQ ID NO: 39. In some embodiments, the endophyte comprises a polynucleotide sequence that is between 97% and 98% identical, at least 98% identical, between 98.0% identical and 99.5% identical, at least 99.5% identical, or 100% identical to SEQ ID NO: 39. In some embodiments, the endophyte is an *Asperigullus ruber*.

In some embodiments, the endophyte comprises a polynucleotide sequence that is at least 97% identical to at least one sequence selected from the group consisting of SEQ ID NOs: 40, 41, 42, and 43. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 40, 41, 42, and 43. In some embodiments, the endophyte comprises at least two polynucleotide sequences that are at least 97% identical to at least two sequences selected from the group consisting of SEQ ID NOs40, 41, 42, and 43. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID Nos: 40, 41, 42, and 43. In some embodiments, the endophyte comprises at least three polynucleotide sequences that are at least 97% identical to at least three sequences selected from the group consisting of SEQ ID NOs: 40, 41, 42, and 43. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 40, 41, 42, and 43. In some embodiments, the endophyte comprises at least four polynucleotide sequences that are at least 97% identical to at least four sequences selected from the group consisting of SEQ ID NOs: 40, 41, 42, and 43. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 40, 41, 42, and 43. In some embodiments, the endophyte is a *Coniochaeta prunicola*.

In some embodiments, the endophyte comprises a polynucleotide sequence that is at least 97% identical to at least one sequence selected from the group consisting of SEQ ID NOs: 44, 45, 46, 47, and 48. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 44, 45, 46, 47, and 48. In some embodiments, the endophyte comprises at least two polynucleotide sequences that are at least 97% identical to at least two sequences selected from the group consisting of SEQ ID NOs: 44, 45, 46, 47, and 48. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 44, 45, 46, 47, and 48. In some embodiments, the endophyte comprises at least three polynucleotide sequences that are at least 97% identical to at least three sequences selected from the group consisting of SEQ ID NOs: 44, 45, 46, 47, and 48. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 44, 45, 46, 47, and 48. In some embodiments, the endophyte comprises at least four polynucleotide sequences that are at least 97% identical to at least four sequences selected from the group consisting of SEQ ID NOs: 44, 45, 46, 47, and 48. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 44, 45, 46, 47, and 48. In some embodiments, the endophyte comprises at least five polynucleotide sequences that are at least 97% identical to at least five sequences selected from the group consisting of SEQ ID NOs: 44, 45, 46, 47, and 48. In some embodiments, the endophyte comprises at least five polynucleotide sequences that are between 97% and 98% identical, at least 98% identical, between 98.0% identical and 99.5% identical, or at least 99.5% identical, or 100% identical to at least five sequences selected from the group consisting of SEQ ID NOs: 44, 45, 46, 47, and 48. In some embodiments, the endophyte is a *Pestalotiopsis neglecta*.

In some embodiments, the endophyte comprises a polynucleotide sequence that is at least 97% identical to at least one sequence selected from the group consisting of SEQ ID NOs: 49, 50, and 51. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 49, 50, and 51. In some embodiments, the endophyte comprises at least two polynucleotide sequences that are at least 97% identical to at least two sequences selected from the group consisting of SEQ ID NOs: 49, 50, and51. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 49, 50, and 51. In some embodiments, the endophyte comprises at least three polynucleotide sequences that are at least 97% identical to at least three sequences selected from the group consisting of SEQ ID NOs: 49, 50, and 51. In some embodiments, the endophyte is a *Enterobacter cowanii*. In some embodiments, the endophyte is deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-B67465. In some embodiments, the endophyte is as deposited under NRRL Culture Deposit No. NRRL Culture Deposit No. NRRL-B67465, and thereafter modified. In some embodiments, the modified endophyte derived from the endophyte deposited as NRRL Culture Deposit No. NRRL-B67465 retains the ability to modulate the nutrient composition of a seed produced by a plant element heterologously disposed with the modified endophyte.

In some cases, the endophyte, or one or more components thereof, is of monoclonal origin, providing high genetic uniformity of the endophyte population in an agricultural formulation or within a plant element or synthetic combination with the endophyte.

In some embodiments, the endophyte can be cultured on a culture medium or can be adapted to culture on a culture medium.

The synthetic compositions provided herein are preferably stable. The endophyte may be shelf-stable, where at least 0.01%, of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf-stable formulation is in a dry formulation, a powder formulation, or a lyophilized formulation. In some embodiments, the formulation is formulated to provide stability for the population of endophytes. In an embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

Endophytes and Synthetic Compositions with Plants and Plant Elements

It is contemplated that the methods and synthetic compositions may be used to improve a characteristic of agronomic importance to a plant.

The methods described herein can also be used with transgenic plants comprising one or more exogenous transgenes, for example, to yield additional trait benefits conferred by the newly introduced endophytic microbes.

For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In one embodiment, it is contemplated that the plant of the present invention is rice (*Oryza* spp.), in particular *O. sativa* and *O. glaberrima*, and members of the major *O. sativa* subspecies japonica, javanica, and indica. In some embodiments, the present invention contemplates the use of endophytes that can confer a beneficial agronomic trait upon a rice plant element or rice plant to which it is heterologously disposed.

In one embodiment, it is contemplated that the plant of the present invention is corn (*Zea* spp.), in particular *Zea mays* ssp. such as *Zea mays indenata, Zea mays indurata, Zea mays amylacea, Zea mays saccharata,* and *Zea mays everta.*

In one embodiment, it is contemplated that the plant of the present invention is wheat (*Triticum* spp.) including species *T. aestivum* and *T. durum* and varieties including hard red winter (HRW), hard red spring (HRS), hard white (HW), durum, soft white (SW), and soft red winter (SRW). In some embodiments, the present invention contemplates the use of endophytes that can confer a beneficial agronomic trait upon a wheat plant element or wheat plant to which it is heterologously disposed.

In one embodiment, it is contemplated that the plant of the present invention is soy (*Glycine max*). In some embodiments, the present invention contemplates the use of endophytes that can confer a beneficial agronomic trait upon a soy plant element or soy plant to which it is heterologously disposed.

In one embodiment, it is contemplated that the plant of the present invention is cotton (genus *Gossypium*, including species such as *Gossypium arboretum, Gossypium herbaceum, Gossypium hirsutum, Gossypium barbadense*). In some embodiments, the present invention contemplates the use of endophytes that can confer a beneficial agronomic trait upon a cotton plant element or cotton plant to which it is heterologously disposed.

In some embodiments, plant elements of the present invention include wild plants and domesticated varieties of the genera *Zea, Triticum, Glycine, Gossypium*. Plants elements may developed by any technique, including but not limited to directed evolution, selection, marker assisted selection, hybridization, outcrossing, backcrossing, in-breeding, polyploidization, reverse breeding, doubled haploids, induced mutation, other genetic or epigenetic modifications, and combinations thereof.

In some cases, the endophytes described herein are capable of moving from one tissue type to another. For example, the present invention's detection and isolation of endophytes within the mature tissues of plants after coating on the exterior of a plant element demonstrates their ability to move from the plant element into the vegetative tissues of a maturing plant. Therefore, in some embodiments, the population of endophytes is capable of moving from the plant element exterior into the vegetative tissues of a plant. In some embodiments, the endophyte that is coated onto the plant element of a plant is capable, upon germination of the plant element into a vegetative state, of localizing to a different tissue of the plant. For example, endophytes can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In an embodiment, the endophyte is capable of localizing to the root and/or the root hair of the plant. In another embodiment, the endophyte is capable of localizing to the photosynthetic tissues, for example, leaves and shoots of the plant. In other cases, the endophyte is localized to the vascular tissues of the plant, for example, in the xylem and phloem. In still another embodiment, the endophyte is capable of localizing to the reproductive tissues (flower, pollen, pistil, ovaries, stamen, fruit) of the plant. In another embodiment, the endophyte is capable of localizing to the root, shoots, leaves and reproductive tissues of the plant. In still another embodiment, the endophyte colonizes a fruit or plant element tissue of the plant. In still another embodiment, the endophyte is able to colonize the plant such that it is present in the surface of the plant (i.e., its presence is detectably present on the plant exterior, or the episphere of the plant). In still other embodiments, the endophyte is capable of localizing to substantially all, or all, tissues of the plant. In certain embodiments, the endophyte is not localized to the root of a plant. In other cases, the endophyte is not localized to the photosynthetic tissues of the plant.

In some cases, endophytes are capable of replicating within the host plant and colonizing the plant.

The endophyte populations described herein are capable of colonizing a host plant. Successful colonization can be confirmed by detecting the presence of the endophyte population within the plant. For example, after applying the endophyte to the plant elements, high titers of the endophyte can be detected in the roots and shoots of the plants that germinate from the plant elements. Detecting the presence of the endophyte inside the plant can be accomplished by measuring the viability of the endophyte after surface sterilization of the plant element or the plant: endophyte colonization results in an internal localization of the endophyte, rendering it resistant to conditions of surface sterilization.

The presence and quantity of endophyte can also be established using other means known in the art, for example, immunofluorescence microscopy using microbe-specific antibodies, or fluorescence in situ hybridization. Alternatively, specific nucleic acid probes recognizing conserved sequences from an endophyte can be employed to amplify a region, for example by quantitative PCR, and correlated to CFUs by means of a standard curve.

In another embodiment, the endophyte is heterologously disposed, for example, on the surface of a reproductive element of an agricultural plant, in an amount effective to be detectable in the mature agricultural plant. In some embodiments, the endophyte is heterologously disposed in an amount effective to be detectable in an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature agricultural plant.

In some cases, the endophyte is capable of colonizing particular plant elements or tissue types of the plant. In an embodiment, the endophyte is heterologously disposed on the plant element or seedling in an amount effective to be detectable within a target tissue of the mature agricultural plant selected from a fruit, a seed, a leaf, or a root, or portion thereof. For example, the endophyte can be detected in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, in the target tissue of the mature agricultural plant.

Endophytes Compatible with Agrichemicals

In certain embodiments, the endophyte is selected on the basis of its compatibility with commonly used agrichemicals. As described herein, plants, particularly agricultural plants, can be treated with a vast array of agrichemicals, including fungicides, biocides (anti-complex agents), herbicides, insecticides, nematicides, rodenticides, bactericides, virucides, fertilizers, and other agents.

In some embodiments, the endophytes display tolerance to an agrichemical selected from the group consisting of: Aeris®, Avicta® DuoCot 202, Cruiser®, Syntenta CCB® (A), Clariva®, Albaugh, Dynasty®, Apron®, Maxim®, Gaucho®, Provoke® ST, Syngenta CCB®, Trilex®, WG Purple, WG Silver, Azoxystrobin, Carboxin, Difenoconazole, Fludioxonil, fluxapyroxad, Ipconazole, Mefenoxam, Metalaxyl, Myclobutanil, Penflufen, pyraclostrobin, Sedaxane, TCMTB, Tebuconazole, Thiram, Triadimenol (Baytan®), Trifloxystrobin, Triticonazole, Tolclofos-methyl, PCNB, Abamectin, Chlorpyrifos, Clothianidin, Imidacloprid, Thiamethoxam, Thiodicarb.

In some cases, it can be important for the endophyte to be compatible with agrichemicals, particularly those with anticomplex properties, in order to persist in the plant although, as described herein, there are many such anticomplex agents that do not penetrate the plant, at least at a concentration sufficient to interfere with the endophyte. Therefore, where a systemic anticomplex agent is used in the plant, compatibility of the endophyte to be inoculated with such agents will be an important criterion.

In an embodiment, natural isolates of endophytes that are compatible with agrichemicals can be used to inoculate the plants according to the methods described herein. For example, endophytes that are compatible with agriculturally employed anticomplex agents can be isolated by plating a culture of endophytes on a petri dish comprising an effective concentration of the anticomplex agent, and isolating colonies of endophytes that are compatible with the anticomplex agent. In another embodiment, an endophyte that is compatible with an anticomplex agent is used for the methods described herein.

Bactericide-compatible endophyte can also be isolated by selection on liquid medium. The culture of endophytes can be plated on petri dishes without any forms of mutagenesis; alternatively, endophytes can be mutagenized using any means known in the art. For example, endophyte cultures can be exposed to UV light, gamma-irradiation, or chemical mutagens such as ethylmethanesulfonate (EMS), ethidium bromide (EtBr) dichlovos (DDVP, methyl methane sulphonale (MMS), triethylphosphate (TEP), trimethylphosphate (TMP), nitrous acid, or DNA base analogs, prior to selection on fungicide comprising media. Finally, where the mechanism of action of a particular bactericide is known, the target gene can be specifically mutated (either by gene deletion, gene replacement, site-directed mutagenesis, etc.) to generate an endophyte that is resilient against that particular chemical. It is noted that the above-described methods can be used to isolate endophytes that are compatible with both bacteriostatic and bactericidal compounds.

It will also be appreciated by one skilled in the art that a plant may be exposed to multiple types of anticomplex compounds, either simultaneously or in succession, for example at different stages of plant growth. Where the target plant is likely to be exposed to multiple anticomplex agents, an endophyte that is compatible with many or all of these agrichemicals can be used to inoculate the plant. An endophyte that is compatible with several agents can be isolated, for example, by serial selection. An endophyte that is compatible with the first agent can be isolated as described above (with or without prior mutagenesis). A culture of the resulting endophyte can then be selected for the ability to grow on liquid or solid media comprising the second agent (again, with or without prior mutagenesis). Colonies isolated from the second selection are then tested to confirm its compatibility to both agents.

Likewise, endophytes that are compatible to biocides (including herbicides such as glyphosate or anticomplex compounds, whether bacteriostatic or bactericidal) that are agriculturally employed can be isolated using methods similar to those described for isolating compatible endophytes. In some embodiments, mutagenesis of the endophyte population can be performed prior to selection with an anticomplex agent. In another embodiment, selection is performed on the endophyte population without prior mutagenesis. In still another embodiment, serial selection is performed on an endophyte: the endophyte is first selected for compatibility to a first anticomplex agent. The isolated compatible endophyte is then cultured and selected for compatibility to the second anticomplex agent. Any colony thus isolated is tested for compatibility to each, or both anticomplex agents to confirm compatibility with these two agents.

Compatibility with an antimicrobial agent can be determined by a number of means known in the art, including the comparison of the minimal inhibitory concentration of the unmodified and modified endophytes. In some embodiments, the present invention discloses an isolated modified endophyte, wherein the endophyte is modified such that it exhibits at least 3 fold greater, for example, at least 5 fold greater, between 5 and 10 fold greater, at least 10 fold greater, between 10 and 20 fold greater, at least 20 fold greater, between 20 and 30 fold greater, at least 30 fold greater or more minimal inhibitory concentration to an antimicrobial agent when compared with the unmodified endophyte.

In a particular embodiment, disclosed herein are endophytes with enhanced compatibility to the herbicide glyphosate. In some embodiments, the endophyte has a doubling time in growth medium comprising at least 1 mM glyphosate, for example, between 1 mM and 2 mM glyphosate, at least 2 mM glyphosate, between 2 mM and 5 mM glyphosate, at least 5 mM glyphosate, between 5 mM and 10 mM glyphosate, at least 10 mM glyphosate, between 10 mM and 15 mM glyphosate, at least 15 mM glyphosate or more, that is no more than 250%, between 250% and 100%, for example, no more than 200%, between 200% and 175%, no more than 175%, between 175% and 150%, no more than 150%, between 150% and 125%, or no more than 125%, of the doubling time of the endophyte in the same growth medium comprising no glyphosate. In one particular embodiment, the endophyte has a doubling time in growth medium comprising 5 mM glyphosate that is no more than 150% the doubling time of the endophyte in the same growth medium comprising no glyphosate.

In another embodiment, the endophyte has a doubling time in a plant tissue comprising at least 10 ppm glyphosate, between 10 and 15 ppm, for example, at least 15 ppm glyphosate, between 15 and 10 ppm, at least 20 ppm glyphosate, between 20 and 30 ppm, at least 30 ppm glyphosate, between 30 and 40 ppm, at least 40 ppm glyphosate or more, that is no more than 250%, between 250% and 200%, for example, no more than 200%, between 200% and 175%, no more than 175%, between 175% and 150%, no more than 150%, between 150% and 125%, or no more than 125%, of the doubling time of the endophyte in a reference plant tissue comprising no glyphosate. In one particular embodiment, the endophyte has a doubling time in a plant tissue comprising 40 ppm glyphosate that is no more than 150% the doubling time of the endophyte in a reference plant tissue comprising no glyphosate.

The selection process described above can be repeated to identify isolates of endophytes that are compatible with a multitude of agents.

Candidate isolates can be tested to ensure that the selection for agrichemical compatibility did not result in loss of a desired bioactivity. Isolates of endophytes that are compatible with commonly employed agents can be selected as described above. The resulting compatible endophyte can be compared with the parental endophyte on plants in its ability to promote germination.

The agrichemical compatible endophytes generated as described above can be detected in samples. For example, where a transgene was introduced to render the endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the endophyte even if it is no longer viable. Thus, commodity plant products produced using the agrichemical compatible endophytes described herein can readily be identified by employing these and related methods of nucleic acid detection.

Beneficial Attributes of Synthetic Compositions of Plant Elements and Endophytes The present invention contemplates the establishment of a relationship between a symbiont and a plant element. In some embodiments, endophyte association results in a detectable change to the plant element, or the whole plant. The detectable change can be an improvement in a number of agronomic traits (e.g., improved general health, increased response to biotic or abiotic stresses, or enhanced properties of the plant or a plant element, including fruits and grains). Alternatively, the detectable change can be a physiological or biological change that can be measured by methods known in the art. The detectable changes are described in more detail in the sections below. As used herein, an endophyte is considered to have conferred an improved agricultural trait whether or not the improved trait arose from the plant, the endophyte, or the concerted action between the plant and endophyte. Therefore, for example, whether a beneficial hormone or chemical is produced by the plant or the endophyte, for purposes, the endophyte will be considered to have conferred an improved agronomic trait upon the host plant, as compared to an isoline plant that has not been heterologously disposed to said endophyte.

In some embodiments, provided herein, are methods for producing a plant element of a plant with a heritably altered trait. The trait of the plant can be altered without known genetic modification of the plant genome, and comprises the following steps. First, a preparation of an isolated endophyte that is heterologously disposed to the plant element of the plant is provided, and optionally processed to produce an endophyte formulation. The endophyte formulation is then contacted with the plant. The plants are then allowed to go to seed, and the seeds are collected.

Improved General Health

Also described herein are plants, and fields of plants, that are heterologously disposed to beneficial endophytes, such that the overall fitness, productivity or health of the plant or a portion thereof, is maintained, increased and/or improved over a period of time. Improvement in overall plant health can be assessed using numerous physiological parameters including, but not limited to, height, overall biomass, root and/or shoot biomass, emergence, seed germination, seedling survival, photosynthetic efficiency, transpiration rate, seed/fruit number or mass, plant grain yield, leaf chlorophyll content, photosynthetic rate, root length, or any combination thereof.

Drought Tolerance

In some cases, a plant resulting from seeds or other plant elements treated with an endophyte can exhibit a physiological change, such as a compensation of the stress-induced reduction in photosynthetic activity. Fv/Fm tests whether or not plant stress affects photosystem II in a dark adapted state. Fv/Fm is one of the most commonly used chlorophyll fluorescence measuring parameter. The Fv/Fm test is designed to allow the maximum amount of the light energy to take the fluorescence pathway. It compares the dark-adapted leaf pre-photosynthetic fluorescent state, called minimum fluorescence, or Fo, to maximum fluorescence called Fm. In maximum fluorescence, the maximum number of reaction centers have been reduced or closed by a saturating light source. In general, the greater the plant stress, the fewer open reaction centers available, and the Fv/Fm ratio is lowered. Fv/Fm is a measuring protocol that works for many types of plant stress. For example, there would be a difference in the Fv/Fm after exposure of an endophyte treated plant that had been subjected to heat shock or drought conditions, as compared to a corresponding control, a genetically identical plant that does not contain the endophytes grown in the same conditions. In some cases, the inoculated plant as disclosed herein can exhibit an increased change in photosynthetic activity ΔFv(ΔFv/Fm) after heat-shock or drought stress treatment, for example 1, 2, 3, 4, 5, 6, 7 days or more after the heat-shock or drought stress treatment, or until photosynthesis ceases, as compared with corresponding control plant of similar developmental stage but not comprising endophytes. For example, a plant having an endophyte able to confer heat and/or drought-tolerance can exhibit a ΔFv/Fm of from about 0.1 to about 0.8 after exposure to heat-shock or drought stress or a ΔFv/Fm range of from about 0.03 to about 0.8 under one day, or 1, 2, 3, 4, 5, 6, 7, or over 7 days post heat-shock or drought stress treatment, or until photosynthesis ceases. In some embodiments, stress-induced reductions in photosynthetic activity can be compensated by at least about 0.25% (for example, at least about 0.5%, between 0.5% and 1%, at least about 1%, between 1% and 2%, at least about 2%, between 2% and 3%, at least about 3%, between 3% and 5%, at least about 5%, between 5% and 10%, at least about 8%, at least about 10%, between 10% and 15%, at least about 15%, between 15% and 20%, at least about 20%, between 20$ and 25%, at least about 25%, between 25% and 30%, at least about 30%, between 30% and 40%, at least about 40%, between 40% and 50%, at least about 50%, between 50% and 60%, at least about 60%, between 60% and 75%, at least about 75%, between 75% and 80%, at least about 80%, between 80% and 85%, at least about 85%, between 85% and 90%, at least about 90%, between 90% and 95%, at least about 95%, between 95% and 99%, at least about 99% or at least 100%) as compared to the photosynthetic activity decrease in a corresponding reference agricultural plant following heat shock conditions. Significance of the difference between inoculated and reference agricultural plants can be established upon demonstrating statistical significance, for example at p<0.05 with an appropriate parametric or non-parametric statistic, e.g., Chi-square test, Student's t-test, Mann-Whitney test, or F-test based on the assumption or known facts that the inoculated plant and reference agricultural plant have identical or near identical genomes (isoline comparison).

In some embodiments, the plants comprise endophytes able to increase heat and/or drought-tolerance in sufficient quantity, such that increased growth or improved recovery from wilting under conditions of heat or drought stress is observed. For example, an endophyte population described herein can be present in sufficient quantity in a plant, resulting in increased growth as compared to a plant that does not contain endophytes, when grown under drought conditions or heat shock conditions, or following such conditions. Increased heat and/or drought tolerance can be assessed with physiological parameters including, but not limited to, increased height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, wilt recovery, turgor pressure, or any combination thereof, as compared to a reference agricultural plant grown under similar conditions. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In various embodiments, endophytes heterologously disposed to the plant can confer various benefits to the plant, including but not limited to: thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. A difference between the inoculated plant (e.g., a plant to which one or more endophytes have been heterologously disposed) and a reference agricultural plant can also be measured using other methods known in the art.

Formulations for Agricultural Use

The endophyte populations described herein are intended to be useful in the improvement of agricultural plants, and as such, may be formulated with other compositions as part of an agriculturally compatible carrier. It is contemplated that such carriers can include, but not be limited to: seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics. The carrier composition with the endophyte populations, may be prepared for agricultural application as a liquid, a solid, or a gas formulation. Application to the plant may be achieved, for example, as a powder for surface deposition onto plant leaves, as a spray to the whole plant or selected plant element, as part of a drip to the soil or the roots, or as a coating onto the plant element prior to planting. Such examples are meant to be illustrative and not limiting to the scope of the invention.

The formulation useful for these embodiments generally and typically include at least one member selected from the group consisting of a buffer, a tackifier, a microbial stabilizer, a fungicide, an anticomplex agent, an herbicide, a nematicide, an insecticide, a bactericide, a virucide, a plant growth regulator, a rodenticide, a desiccant, and a nutrient.

The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified population (see, for example, U.S. Pat. No. 7,485,451). Suitable formulations that may be prepared include wettable powders, granules, gels, agar strips or pellets, thickeners, biopolymers, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, wheat or other biological materials such as seed, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In an embodiment, the formulation can include a tackifier or adherent. Such agents are useful for combining the complex population of the invention with carriers that can contain other compounds (e.g., control agents that are not biologic), to yield a coating composition. Such compositions help create coatings around the plant or plant element to maintain contact between the endophyte and other agents with the plant or plant element. In some embodiments, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, carragennan, PGA, other biopolymers, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788.

It is also contemplated that the formulation may further comprise an anti-caking agent.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl CO, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, Pluronic. In some embodiments, the surfactant is present at a concentration of between 0.01% v/v to 10% v/v. In another embodiment, the surfactant is present at a concentration of between 0.1% v/v to 1% v/v. An example of an anti-foaming agent would be Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the population used, and should promote the ability of the endophyte population to survive application on the seeds and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%. In some embodiments, components of a sugar-based microbial stabilizer include, but are not limited to, glucose, sucrose, polyvinylpyrrolidone K 30 (PVP30K), mineral oil, soy lecithin, peptone, monopotassium phosphate (KH2PO4) and dipotassium phosphate (K2HPO4). In an alternate embodiment, components of a non-sugar based microbial stabilizer include, but are not limited to, polyvinylpyrrolidone K 30 (PVP30K), polyvinylpyrrolidone/vinyl acetate (PVP-VA), soy lecithin, peptone, mineral oil, hydroxypropyl-guar (HP-Guar), monopotassium phosphate (KH2PO4) and dipotassium phosphate (K2HPO4). Components of exemplary microbial stabilizers for use with the invention described herein are depicted in Table 1 and Table 2.

TABLE 1

Exemplary Sugar Based Microbial Stabilizer

| Component | Percentage (%), by weight |
| --- | --- |
| Glucose | 11.4 |
| Sucrose | 11.4 |
| PVP30K | 2.8 |
| Mineral oil | 5.7 |
| Soy lecithin | 0.3 |
| Peptone | 11.4 |
| KH2PO4 | 0.78 |
| K2HPO4 | 0.99 |
| Non-chlorinated water | 55 |

TABLE 2

Exemplary Non-sugar Based Microbial Stabilizer

| Component | Percentage (%), by weight |
| --- | --- |
| PVP30K | 3.8 |
| PVP-VA | 3.8 |
| Soy lecithin | 0.4 |
| Peptone | 15.4 |
| Mineral oil | 6.0 |
| HP-Guar | 0.2 |
| KH2PO4 | 0.96 |
| K2HP04 | 1.23 |
| Non-chlorinated water | 68 |

In some cases, it is advantageous for the formulation to contain agents such as a fungicide, an anticomplex agent, an herbicide, a nematicide, an insecticide, a plant growth regulator, a rodenticide, a bactericide, a virucide, or a nutrient. Such agents are ideally compatible with the agricultural plant element or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, endophyte populations can be mixed or suspended in water or in aqueous solutions. Suitable liquid diluents or carriers include water, aqueous solutions, petroleum distillates, or other liquid carriers.

Solid compositions can be prepared by dispersing the endophyte populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In some cases, a flowability polymer, also referred to as a plantability polymer such as Flo Rite® e.g., Flo-Rite® 1706 (BASF, Ludwigshafen, Germany). In some embodiments, a flowability or plantability polymer is DISCO™ AG (Incotec, Enkhuizen, the Netherlands). In some embodiments, a flowability or plantability polymer is Kannar® Universal Wonder (Kannar Earth Science, Ltd., Buford, Ga.).

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil, neem oil, cottonseed oil, and other compositions such as glycerol, ethylene glycol, polyethylene glycol, propylene glycol, polypropylene glycol, etc.

In an embodiment, the formulation is ideally suited for coating of a population of endophytes onto plant elements. The endophytes populations described in the present invention are capable of conferring many fitness benefits to the host plants. The ability to confer such benefits by coating the populations on the surface of plant elements has many potential advantages, particularly when used in a commercial (agricultural) scale.

The endophyte populations herein can be combined with one or more of the agents described above to yield a formulation suitable for combining with an agricultural plant element, seedling, or other plant element. Endophyte populations can be obtained from growth in culture, for example, using a synthetic growth medium. In addition, endophytes can be cultured on solid media, for example on petri dishes, scraped off and suspended into the preparation. Endophytes at different growth phases can be used. For example, endophytes at lag phase, early-log phase, mid-log phase, late-log phase, stationary phase, early death phase, or death phase can be used. Endophytic spores may be used for the present invention, for example but not limited to: arthospores, sporangispores, conidia, chlamadospores, pycnidiospores, endospores, zoospores.

The formulations comprising endophyte populations typically contains between about 0.1 to 95% by weight, for example, between about 1% and 90%, between about 3% and 75%, between about 5% and 60%, between about 10% and 50% in wet weight of the population. It is preferred that the formulation contains at least about $10^3$ CFU per ml of formulation, for example, at least about $10^4$, at least about $10^5$, at least about $10^6$, at least about $10^7$ CFU, at least about $10^8$ CFU per ml of formulation. It is preferred that the formulation be applied to the plant element at about $10^2$ CFU/seed, between $10^2$ and $10^3$ CFU, at least about $10^3$ CFU, between $10^3$ and $10^4$ CFU, at least about $10^4$ CFU, between $10^4$ and $10^5$ CFU, at least about $10^5$ CFU, between $10^5$ and $10^6$ CFU, at least about $10^6$ CFU, between $10^6$ and $10^7$ CFU, at least about $10^7$ CFU, between $10^7$ and $10^8$ CFU, or even greater than $10^8$ CFU per seed.

Populations of Plant Elements (PEs)

In another embodiment, the invention provides for a substantially uniform population of synthetic compositions comprising plant elements (PEs), comprising two or more PEs comprising the endophytic population, as described herein above. Substantial uniformity can be determined in many ways. In some cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the PEs in the population, comprises the endophytic population in an amount effective to colonize a plant, or plants, derived from said PEs when disposed on the surface of the PEs. In other cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant element s in the population, contains at least 1, between 10 and 10, 10, between 10 and 100, or 100 CFU on the plant element surface or per gram of plant element, for example, between 100 and 200 CFU, at least 200 CFU, between 200 and 300 CFU, at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU, between 100,000 and 300,000 CFU, at least 300,000 CFU, between 300,000 and 1,000,000 CFU, or at least 1,000,000 CFU per plant element or more.

In a particular embodiment, the population of plant elements is packaged in a bag or container suitable for commercial sale. Such a bag contains a unit weight or count of the plant elements comprising the endophytic population as described herein, and further comprises a label. In an embodiment, the bag or container contains at least 100 plant elements, between 100 and 1,000 plant elements, 1,000 plant elements, between 1,000 and 5,000 plant elements, for example, at least 5,000 plant elements, between 5,000 and 10,000 plant elements, at least 10,000 plant elements, between 10,000 and 20,000 plant elements, at least 20,000 plant elements, between 20,000 and 30,000 plant elements, at least 30,000 plant elements, between 30,000 and 50,000 plant elements, at least 50,000 plant elements, between 50,000 and 70,000 plant elements, at least 70,000 plant elements, between 70,000 and 80,000 plant elements, at least 80,000 plant elements, between 80,000 and 90,000, at least 90,000 plant elements or more. In another embodiment, the bag or container can comprise a discrete weight of plant elements, for example, at least 1 lb, between 1 and 2 lbs, at least 2 lbs, between 2 and 5 lbs, at least 5 lbs, between 5 and 10 lbs, at least 10 lbs, between 10 and 30 lbs, at least 30 lbs, between 30 and 50 lbs, at least 50 lbs, between 50 and 70 lmbs, at least 70 lbs or more. The bag or container comprises a label describing the plant elements and/or said endophytic population. The label can contain additional information, for example, the information selected from the group consisting of: net weight, lot number, geographic origin of the plant elements, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas-or waterproof containments).

In some cases, a sub-population of seeds comprising the endophytic population is further selected on the basis of increased uniformity, for example, on the basis of uniformity of microbial population. For example, individual plant elements of pools collected from individual cobs, individual plants, individual plots (representing plants inoculated on the same day) or individual fields can be tested for uniformity of microbial density, and only those pools meeting specifications (e.g., at least 80% of tested plant elements have minimum density, as determined by quantitative methods described elsewhere) are combined to provide the agricultural seed sub-population.

The methods described herein can also comprise a validating step. The validating step can entail, for example, growing some plant elements collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

In some embodiments, methods described herein include planting a synthetic composition described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating plant elements. When used to coat plant elements, the composition may be applied to the plant elements and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In an embodiment, plant elements may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed.

In another embodiment, the treatment entails coating plant elements. One such process involves coating the inside wall of a round container with the composition(s) described herein, adding plant elements, then rotating the container to cause the plant elements to contact the wall and the composition(s), a process known in the art as "container coating." Plant elements can be coated by combinations of coating methods. Soaking typically entails using liquid forms of the compositions described. For example, plant elements can be soaked for about 1 minute to about 24 hours (e.g., for at least 1 min, between 1 and 5 min, 5 min, between 5 and 10 min, 10 min, between 10 and 20 min, 20 min, between 20 and 40 min, 40 min, between 40 and 80 min, 80 min, between 80 min and 3 hrs, 3 hrs, between 3 hrs and 6 hrs, 6 hr, between 6 hrs and 12 hrs, 12 hr, between 12 hrs and 24 hrs, 24 hrs).

Population of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability is caused by a multitude of factors, including uneven environmental conditions and management practices. Another possible source of variability can, in some cases, be due to the heterogeneity of the endophyte population inhabiting the plants. By providing endophyte populations onto plant reproductive elements, the resulting plants generated by germinating the plant reproductive elements have a more consistent endophyte collection, and thus are expected to yield a more uniform population of plants.

Therefore, in another embodiment, the invention provides a substantially uniform population of plants. The population can include at least 5 plants, between 5 and 10 plants at least 10 plants, between 10 and 100 plants, for example, at least 100 plants, between 100 and 300 plants, at least 300 plants, between 300 and 1,000 plants, at least 1,000 plants, between 1,000 and 3,000 plants, at least 3,000 plants, between 3,000 and 10,000 plants, at least 10,000 plants, between 10,000 and 30,000 plants, at least 30,000 plants, between 30,000 and 100,000 plants, at least 100,000 plants or more. The plants may be derived from plant reproductive elements comprising endophyte populations as described herein. The plants are cultivated in substantially uniform groups, for example in rows, groves, blocks, circles, or other planting layout.

The uniformity of the plants can be measured in a number of different ways. In some embodiments, there is an increased uniformity with respect to endophytes within the plant population. For example, In some embodiments, a substantial portion of the population of plants, for example at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant elements or plants in a population, contains a threshold number of an endophyte population. The threshold number can be at least 10 CFU, between 10 and 100 CFU, at least 100 CFU, between 100 and 300 CFU, for example at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU or more, in the plant or a part of the plant. Alternatively, in a substantial portion of the population of plants, for example, in at least 1%, between 1% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plants in the population, the endophyte population that is provided to the seed or seedling represents at least 0.1%, between 0.1% and 1% at least 1%, between 1% and 5%, at least 5%, between 5% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 80%, at least 80%, between 80% and 90%, at least 90%, between 90% and 95%, at least 95%, between 95% and 99%, at least 99%, between 99% and 100%, or 100% of the total endophyte population in the plant/seed.

In an embodiment, there is increased genetic uniformity of a substantial proportion or all detectable endophytes within the taxa, genus, or species of a component relative to an uninoculated control. This increased uniformity can be a result of the endophyte being of monoclonal origin or otherwise deriving from a population comprising a more uniform genome sequence and plasmid repertoire than would be present in the endophyte population a plant that derives its endophyte community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions. In other cases, there can be a reduction in the standard deviation in the flowering time of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions.

Commodity Plant Products

The present invention provides a commodity plant product, as well as methods for producing a commodity plant product, that is derived from a plant. As used herein, a "commodity plant product" refers to any composition or product that is comprised of material derived from a plant, seed, plant cell, or plant element of the present invention. Commodity plant products may be sold to consumers and can be viable or nonviable. Nonviable commodity products include but are not limited to nonviable plant elements and grains; processed seeds, seed parts, and plant elements; dehydrated plant tissue, frozen plant tissue, and processed plant tissue; seeds and plant elements processed for animal feed for terrestrial and/or aquatic animal consumption, oil, meal, flour, flakes, bran, fiber, paper, tea, coffee, silage, crushed of whole grain, and any other food for human or animal consumption such as the fruit or other edible portion of the plant; and biomasses and fuel products; and raw material in industry.

Industrial uses of oils derived from the agricultural plants described herein include ingredients for paints, plastics, fibers, detergents, cosmetics, lubricants, and biodiesel fuel. Plant oils may be split, inter-esterified, sulfurized, epoxidized, polymerized, ethoxylated, or cleaved. Designing and producing plant oil derivatives with improved functionality and improved oleochemistry is a rapidly growing field. For example, a mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

Methods of Using Endophytes and Synthetic Compositions Comprising Endophytes

As described herein, purified endophyte populations and synthetic compositions comprising the same (e.g., formulations) can be used to confer beneficial traits to the host plant.

The invention will be further described in the following examples, which do not limit the scope of the invention described in the claims. Each patent application, journal article, citation, and other references are herein incorporated by reference in their entirety, as if each has been incorporated by reference individually.

EXAMPLES

Example 1

Isolation and Identification of Endophytes

Isolation and cultivation of endophytic microbes from agricultural plants was performed using methods well known in the art. MIC-15870 was isolated from the roots of Zea mays domesticated variety B73. MIC-84414 was isolated from Bouteloua gracilis seed. MIC-68000 was isolated from the seeds of a Zea mays local to the southwestern United States. DNA was extracted from the ground tissues using the DNeasy DNA extraction kit (Qiagen, Hilden, Germany) according to the manufacturer's instructions. The endophytes were characterized by the sequences of genomic regions, these sequences are listed in Table 4. Primers that amplify genomic regions of the endophytes of the present invention are listed in Table 3. Additional isolation and cultivation of endophytic microbes from agricultural plants was performed using methods well known in the art. MIC-99023 was isolated from *Platycladus orientalis* tissue. MIC-19994 was isolated from *Platycladus orientalis* tissue. These endophytes were characterized by the sequences of genomic regions, these sequences are listed in Table 4. Primers that amplify genomic regions of the endophytes of the present invention are listed in Table 3. Additional isolation and cultivation of endophytic microbes from agricultural plants was performed using methods well known in the art. MIC-82330 was isolated from seed of a rye cultivar. The endophytes were characterized by the sequences of genomic regions, these sequences are listed in Table 4. Primers that amplify genomic regions of the endophytes of the present invention are listed in Table 1.

TABLE 3

Primer sequences useful in identifying microbes of the present invention

| Primers | Genomic locus |
|---|---|
| 27f (5'-AGAGTTTGATYMTGGCTCAG-3') (SEQ ID NO: 1)<br>1492r (5'-GGTTACCTTGTTACGACTT-3') (SEQ ID NO: 2) | 16S |
| 515f (5'-GTGYCAGCMGCCGCGGTAA-3') (SEQ ID NO: 3)<br>806r (5'-GGACTACNVGGGTWTCTAAT-3' (SEQ ID NO: 4) | 16S |
| ITS_1 (5'-CTTGGTCATTTAGAGGAAGTAA-3') (SEQ ID NO: 5)<br>LR5 (5'-TCCTGAGGGAAACTTCG-3') (SEQ ID NO: 6) | ITS<br>ITS |
| ITS_2 (5'-GCTGCGTTCTTCATCGATGC-3') (SEQ ID NO: 6)<br>ITS_3 (5'-GCATCGATGAAGAACGCAGC-3') (SEQ ID NO: 7) | ITS |
| MIC-15870-F01, unique genomic region, primer-amplicon F<br>(5'-TGGTCAACTAGCGAACGTGT-3') (SEQ ID NO: 9)<br>MIC-15870-R01, unique genomic region, primer-amplicon R<br>(5'-AGAGGCGAACGGGTACACT-3') (SEQ ID NO: 10) | unique genomic region |
| MIC-84414-F01, unique genomic region, primer-amplicon F<br>(5'-AAATGTTGTTCATGCGACCA-3') (SEQ ID NO: 11)<br>MIC-84414-R01, unique genomic region, primer-amplicon R<br>(5'-TCTCCCAGGAGCTTTCGTTA-3') (SEQ ID NO: 12) | unique genomic region |
| MIC-19994-F01, unique genomic region, primer-amplicon F<br>(5'-TGCTGGTAGTGCGAATGAAA-3') (SEQ ID NO: 13)<br>MIC-19994-R01, unique genomic region, primer-amplicon R<br>(5'-CTTTCGGGTTCCATCAGGT-3') (SEQ ID NO: 14) | unique genomic region |
| MIC-99023-F01, unique genomic region, primer-amplicon F<br>(5'-CCAGTTTCCTGTCCACCAA-3') (SEQ ID NO: 15)<br>MIC-99023-R01, unique genomic region, primer-amplicon R<br>(5'-TAGGCGTTGTTGTTGTTGTTGT-3') (SEQ ID NO: 16) | unique genomic region |
| MIC-82330, unique genomic region-F<br>(5'-ACGATCTCGGCGGGTAAT-3') (SEQ ID NO: 17)<br>MIC-82330, unique genomic region-R<br>(5'-GTTCGGAGCCCTATGTTGG-3') (SEQ ID NO: 18) | unique genomic region |
| 60S-506F60S, ribosomal protein L 10, primer-amplicon F<br>(5'-GHGACAAGCGTTTCTCNGG-3') (SEQ ID NO: 24)<br>60S-908F60S, ribosomal protein L 10, primer-amplicon R<br>(5'-CTTVAVYTGGAACTTGATGGT-3') (SEQ ID NO: 25) | 60S ribosomal protein L 10 |
| Btub2Fd, beta-tubulin, primer-amplicon F<br>(5'-GTBCACCTYCARACCGGYCARTG-3') (SEQ ID NO: 20)<br>Btub4Rd, beta-tubulin, primer-amplicon R<br>(5'-CCRGAYTGRCCRAARACRAAGTTGTC-3') (SEQ ID NO: 21) | Beta-tubulin |
| LR0R, long subunit rRNA gene, primer-amplicon F<br>(5'-ACCCGCTGAACTTAAGC-3') (SEQ ID NO: 26)<br>LR5, long subunit rRNA gene, primer-amplicon R<br>(5'-TCCTGAGGGAAACTTCG-3') (SEQ ID NO: 27) | long subunit rRNA gene |
| NS4, small subunit rRNA gene, primer-amplicon R<br>(5'-CTTCCGTCAATTCCTTTAAG-3') (SEQ ID NO: 28)<br>SR1R, small subunit rRNA gene, primer-amplicon F<br>(5'-TACCTGGTTGATQCTGCCAGT-3') (SEQ ID NO: 29) | small subunit rRNA gene |
| fRPB2-5F<br>(5'-GAYGAYMGWGATCAYTTYGG-3') (SEQ ID NO: 22)<br>bRPB2-7.1R<br>(5'-CCCATRGCYTGYTTMCCCATDGC-3') (SEQ ID NO: 19) | second largest subunit of RNA polymerase II |

TABLE 3-continued

Primer sequences useful in identifying microbes of the present invention

| Primers | Genomic locus |
| --- | --- |
| fRPB2-5F<br>(5'-GAYGAYMGWGATCAYTTYGG-3') (SEQ ID NO: 22)<br>fRPB2-7R<br>(5'-CCCATWGCYTGCTTMCCCAT-3') (SEQ ID NO: 23) | second largest subunit of RNA polymerase II |
| fusA-f2, elongation factor G-F<br>(5'-TCGCGTTCGTTAACAAAATGGACCGTAT-3') (SEQ ID NO: 30)<br>fusA-R2, elongation factor G-R<br>(5'-TCGCCAGACGGCCCAGAGCCAGACCCAT-3') (SEQ ID NO: 31) | elongation factor G |

TABLE 4

Exemplary sequences of endophytes of the present invention

| SEQ ID | MICID | Gene/Locus | Sequence |
| --- | --- | --- | --- |
| 32 | MIC-15870 | ITS | TCTTGGTCATTTAGAGGAAGTAAAAGTCGTAACAAGGTTTCCGTAGGTGAACCTG<br>CGGAAGGATCATTACACATTCGGGGCGCTTCGGCGCTCCTTATACACCCACCCTC<br>TGCCTACGTGTACCTCTATAGCTTCCTCGGCGGGCTCGCCCGCCGCCAGGAACCC<br>ACGAAACCCCTTGCATTATACGCGAAAACTTCTGATAACAAACCTAAATTATCAC<br>AACTTTCAACAATGGATCTCTTGGTTCTGGCATCGATGAAGAACGCAGCGAAATG<br>CGATAAGTAGTGTGAATTGCAGAATTCAGTGAATCATCGAATCTTTGAACGCACA<br>TTGCGGCCATAGGTATTCCTTTGGCCATGCCTGTTCGAGCGTCATTTACACCCTC<br>AAGCCTAGCTTGGTGTTGGGCGTCTGTCCCGCCGTTCTCGCGCGCGGACTCGCCT<br>CAAAGTCATTGGCGGCGGTCGTGCCGGCCCCCTCGCGCAGCACATTTGCGCTTCT<br>CGGAGGCCCGGCGGATCCGCGCTCCAGCAAGACCTTTCACGACTTGACCTCGGAT<br>CAGGTAGGGATACCCGCTGAACTTAAGCATATCAATAAGCGGAGGAAAAGAAACC<br>AACAGGGATTGCCCTAGTAACGGCGAGTGAAGCGGCAACAGCTCAAATTTGAAAT<br>CTGGCCCCTTTGGGGTCCGAGTTGTAATTTGCAGAGGGTGCTTTGGCGTTGGCGG<br>CGGTCTAAGTTCCTTGGAACAGGACATCGCAGAGGGTGAGAATCCCGTATGTGGT<br>CGCATGCCTTCGCCGTGTAAAGCCCCTTCGACGAGTCGAGTTGTTTGGGAATGCA<br>GCTCTAAATGGGAGGTAAATTTCTTCTAAAGCTAAATACCGGCCAGAGACCGATA<br>GCGCACAAGTAGAGTGATCGAAAGATGAAAAGCACTTTGGAAAGAGAGTCAAACA<br>GCACGTGAAATTGTTGAAAGGGAAGCGCTTGCAGCCAGACTTGCCTGTAGTTGCT<br>CACCCGGGCTCCTGCCCGGGGCACTCTTCTGCAGGCAGGCCAGCATCAGTTTGGG<br>CGGTCGGATAAAGGGCTCTGACACGTACTTCCCCTCGGGGTTGACATACAGGGGA<br>GCCGCAATGCGACCAGCCCGGACTGAGGTCCGCGCATCTGCTAGGATGCTGGCGT<br>AATGGCTGTAAGCGGCCCGTCTTGAAACACGGACCAAGGAGTCTAACATCTATGC<br>GAGTGTTTGGGTGTCAAGCCCGAGCGCGCAATGAAAGTGAACGGAGGTGGGAGCC<br>CCTCGGGGTGCACCATCGACCGATCCTGATGTCTTCGGATGGATTTGAGTAAGAG<br>CATAGCTGTTGGGACCCGAAAGATGGTGAACTATGCTTGAATAGGGTGAAGCCAG<br>AGGAAACTCTGGTGGAGGCTCGCAGCGGTTCTGACGTGCAAATCGATCGTCAAAT<br>TTGGGCATAGGGGCGAAAGACTAATC |
| 33 | MIC-15870 | Unique genomic region | TGGTCAACTAGCGAACGTGTTTGGCCGCAGGTCTCCTCTTATTTATTGCGTTGCG<br>CTTTTCGCTTTGGGGAGTGGGATTGCTGGAGGCGCCCATAATCCTGGAATGTTAA<br>TATCTGGACGTACAGTACAAGGTGTAGGCGCAGGAGGCATATATGTCCTCCTTGA<br>TATCGTGTGCTGCGATCTGGTACCACTCCGCGAGCGTGGAAAATATGTCGGCCTA<br>ATGAACTCATGGGCCGGTGTTGCTGCTGGAATTGGGCCTGTCATAGGTGGAGCCT<br>TGGCCGATACTAACTGGCGCTGGATATTCTATCTCAATCTTCCGATCTGTGGGCT<br>GGCGTTAGGCGTGGTTTTGCTTTTCATGCGAATGAAAACTGGTACGCAGGGCGAA<br>GGCGTGTTGAAGCTTCGCCAAATTGATTATCTGGGGAGTTTTATTTTCATACCGA<br>GTATGATCGCACTTCTATACGGCTTGATCACTGGAGGCATTCAATATCCGTGGTC<br>ATCGTGGCGGATTATTCTCCCATTGGTGATTGGCGTTGCCGGCTGGATACTATTC<br>CACATCCAACAGTTCTTCACGGACGTCCCAAGTGTACCCGTTCGCCTCT |
| 34 | MIC-84414 | ITS | TCTTGGTCATTTAGAGGAAGTAAAAGTCGTAACAAGGTCTCCGTAGGTGAACCTG<br>CGGAGGGATCATTACACAATAAAATACGAAGGCCGTTCGCGGCTGGACTATTTAT<br>TACCCTTGTCTTTTGCGCACTTGTTGTTTCCTGGGCGGGTTCGCTCGCCACCAGG<br>ACCACAATATAAACCTTTTTTATGCAGTTGCAATCAGCGTCAGTATAACAAATGT<br>AAATCATTTACAACTTTCAACAACGGATCTCTTGGTTCTGGCATCGATGAAGAAC<br>GCAGCGAAATGCGATACGTAGTGTGAATTGCAGAATTCAGTGAATCATCGAATCT<br>TTGAACGCACATTGCGCCCTTTGGTATTCCAAAGGGCATGCCTGTTCGAGCGTCA<br>TTTGTACCCTCAAGCTTTGCTTGGTGTTGGGCGTTTTTGTCTTTGGCCCGCCAAA<br>GACTCGCCTTAAAATGATTGGCAGCCGGCCTACTGGTTTCGCAGCGCAGCACATT<br>TTTGCGCTTGCAATCAGCAAAAGAGGACGGCAATCCATCAAGACTCCTTCTCACG<br>TTTGACCTCGGATCAGGTAGGGATACCCGCTGAACTTAAGCATATCAATAAGCGG<br>AGGAAAAGAAACCAACAGGGATTGCCCTAGTAACGGCGAGTGAAGCGGCAACAGC<br>TCAAATTTGAAATCTGGCTCTTTCAGAGTCCGAGTTGTAATTTGCAGAGGGCGCT<br>TTGGCTTTGGCAGCGGTCCAAGTTCCTTGGAACAGGACGTCACAGAGGGTGAGAA<br>TCCCGTACGTGGTCGCTAGCTATTGCCGTGTAAAGCCCCTTCGACGAGTCGAGTT<br>GTTTGGGAATGCAGCTCTAAATGGGAGGTAAATTTCTTCTAAAGCTAAATATTGG |

TABLE 4-continued

Exemplary sequences of endophytes of the present invention

| SEQ ID | MICID | Gene/Locus | Sequence |
|---|---|---|---|
| | | | CCAGAGACCGATAGCGCACAAGTAGAGTGATCGAAAGATGAAAAGCACTTTGGAA<br>AGAGAGTCAAACAGCACGTGAAATTGTTGAAAGGGAAGCGCTTGCAGCCAGACTT<br>GCTTGCAGTTGCTCATCCGGGCTTTTGCCCGGTGCACTCTTCTGCAGGCAGGCCA<br>GCATCAGTTTGGGCGGTGGGATAAAGGTCTCTGTCACGTACCTTCCTTCGGGTTG<br>GCCTTATAGGGGAGACGCCATACCACCAGCCTGGACTGAGGTCCGCGCATCTGCT<br>AGGATGCTGGCGTAATGGCTGTAAGCGGCCCGTCTTGAAACACGGACCAAGGAGT<br>CTAACATCTATGCGAGTGTTTGGGTGTCAAGCCCGAGCGCGTAATGAAAGTGAAC<br>GGAGGTGGGAACCCGCAAGGGTGCACCATCGACCGATCCTGAAGTTTACGGAAGG<br>ATTTGAGTAAGAGCATGGCTGTTGGGACCCGAAAGATGGTGAACTATGCTTGAAT<br>AGGGTGAAGCCAGAGGAAACTCTGGTGGAGGCTCGCAGCGGTTCTGACGTGCAAA<br>TCGATCGTCAAATTTGGGCATAGGGGCGAAAGACT |
| 35 | MIC-<br>84414 | RPB2 | CCCATAGCTTGCTTACCCATGGCAGATTGGTATGTGTTACGGGCGACTGGTTGT<br>GATCTGGGAAGGGAATGATACTAGCGCAAATACCCAAGATCATAGCTGGGTGAAT<br>CTCACAATGGGTGTAGGCGTGGATGCGAGGATCCGGTAGTGGCTTGAGGCGGCGG<br>AGTCGATCCTTGCCTTCAGTAGATCGCTCAGCTGCGGGCAAGCCCATCTTCATTT<br>CTCGCCATTCTTCCAAATCCTCGGGAGAGAATGTTATCATTGCAGTTTCTTCTTC<br>CTCGGCATCGAGGTATTCAACGACACCGTCTTGAATGAGACCTCTCCAGCCGTAT<br>GTAGCCTGCTCGACTTCCTCTTGACTCCAGCCTTGTCTTGTGCTGGTCTCTTGCT<br>GTTCAGCCTTGAGCTTGTTGCTGATTTCCTTGGTAAAGATGAGGTGGTTCCGGTT<br>TGGCTTCCGAATATCGTTTTCTACGACGAACAAAGGCCTCATGACACGACCCGCA<br>TCTGTGAAGATCTTGAACTCTCTGTCGCGAATATCACGAATCAAACTCATCTCGT<br>AAGACAGAGTACCATTGCGGCGAAGCTCCTGCACGACTGTGACAAGCTGCTGAGC<br>ATTTGAATGAACACCAACCCAGACACCGTTAACGAAGACCTTGGTCGCATCCGGG<br>TTCTGATTCTGGTCGTACTCCTCGAGAAGTTGCATGTTACGTTGTGTCATGAAGT<br>CGATAATGGGCGATGCATCGCTACCAACACTGACATAACACATAAGAGACAAGTT<br>CTTGACCAGACCGCAAGCCTGTCCTTCGGGCGTCTCAGCAGGGCAGACAAGACCC<br>CAATGAGAGTTGTGAAGCTGTCGCGGCTTTGCCAACTTACCATCACGTCCAACGG<br>GGGTGTTCGTTCGACGCAGATGGGACAGTGTGGAGGCATAGGTGTATCGGTTCAA<br>CACCTGCGAAACACCAGCCTTGGCAGATGCAGCCTTCTTCTGATCACCCCAATTG<br>CCTGTAGCCAGAGAGTACTTCAGGCCGTTTGTGATGATGCTGGCTTTCACAGCCA<br>TTTGAACGTTGAAGTCTTGGTTGTTTTCCACGCACCGCTGGAGGTACTTGTAGAC<br>ATCCTTGGTGAGCTTCAGGAACAAGATTCGGAACAAGTTGGCAATCAGAGGTCCA<br>GCCAGATCTAGTCGCTTCTTTCCAAAGTGATCACGATCGTCC |
| 36 | MIC-<br>84414 | RPB2 | CCCATAGCTTGCTTACCCATGGCAGATTGGTATGTGTTACGGGCGACTGGTTGT<br>GATCTGGGAAGGGAATGATACTAGCGCAAATACCCAAGATCATAGCTGGGTGAAT<br>CTCACAATGGGTGTAGGCGTGGATGCGAGGATCCGGTAGTGGCTTGAGGCGGCGG<br>AGTCGATCCTTGCCTTCAGTAGATCGCTCAGCTGCGGGCAAGCCCATCTTCATTT<br>CTCGCCATTCTTCCAAATCCTCGGGAGAGAATGTTATCATTGCAGTTTCTTCTTC<br>CTCGGCATCGAGGTATTCAACGACACCGTCTTGAATGAGACCTCTCCAGCCGTAT<br>GTAGCCTGCTCGACTTCCTCTTGACTCCAGCCTTGTCTTGTGCTGGTCTCTTGCT<br>GTTCAGCCTTGAGCTTGTTGCTGATTTCCTTGGTAAAGATGAGGTGGTTCCGGTT<br>TGGCTTCCGAATATCGTTTTCTACGACGAACAAAGGCCTCATGACACGACCCGCA<br>TCTGTGAAGATCTTGAACTCTCTGTCGCGAATATCACGAATCAAACTCATCTCGT<br>AAGACAGAGTACCATTGCGGCGAAGCTCCTGCACGACTGTGACAAGCTGCTGAGC<br>ATTTGAATGAACACCAACCCAGACACCGTTAACGAAGACCTTGGTCGCATCCGGG<br>TTCTGATTCTGGTCGTACTCCTCGAGAAGTTGCATGTTACGTTGTGTCATGAAGT<br>CGATAATGGGCGATGCATCGCTACCAACACTGACATAACACATAAGAGACAAGTT<br>CTTGACCAGACCGCAAGCCTGTCCTTCGGGCGTCTCAGCAGGGCAGACAAGACCC<br>CAATGAGAGTTGTGAAGCTGTCGCGGCTTTGCCAACTTACCATCACGTCCAACGG<br>GGGTGTTCGTTCGACGCAGATGGGACAGTGTGGAGGCATAGGTGTATCGGTTCAA<br>CACCTGCGAAACACCAGCCTTGGCAGATGCAGCCTTCTTCTGATCACCCCAATTG<br>CCTGTAGCCAGAGAGTACTTCAGGCCGTTTGTGATGATGCTGGCTTTCACAGCCA<br>TTTGAACGTTGAAGTCTTGGTTGTTTTCCACGCACCGCTGGAGGTACTTGTAGAC<br>ATCCTTGGTGAGCTTCAGGAACAAGATTCGGAACAAGTTGGCAATCAGAGGTCCA<br>GCCAGATCTAGTCGCTTCTTTCCAAAGTGATCACGATCGTCC |
| 37 | MIC-<br>84414 | Beta-tubulin | CCCGACTGGCCGAAGACGAAGTTGTCGGGCGGAAGAGCTGACCAAAGGGACCAG<br>CGCGGACAGCGTCCATGGTACCGGGCTCGAGATCGACGAGGACGGCACGGGGCAC<br>GAACTTGTTGTTGGAAGCCTGCTGCACATCAGTATTGGTCTTTTGTCTGTTGGGG<br>CTTCACCGAGGGACGTACTTCGTTGAAGTAGACGTTCATGCGCTCGAGCTGAAGG<br>TCAGAGGGTGCCGTTGTAGACACCAGAGCCGTCGAGGCCATGCTCGAGCTGAAGG<br>TCTGCCAGAAGGCGGCACCAATTTGGTTACCCTGTAGCGGCTGTTAGCAGTCGTT<br>CCCGTGGTGTTTTCAGGCGGCGCGAGACTTACGCATTGACCGGTCTGGAGGTGAA<br>CC |
| 38 | MIC-<br>84414 | Unique<br>genomic<br>region | AAATGTTGTTCATGCGACCAATGGATTTGCAAGTCATCTTGTACCCGGCCTCCGC<br>AAGAAGATCGTAGGCGCACGAGCGCACATGTCGGCTCAGCGACCAGGGGAACTAT<br>TCCCTAACAGTGGTGGCATGCGCTCATGGAGTGTGATTTATGGTGGGGAGTTTGA<br>CTATGTCACCCAACGGCCTTCCGCGGACGGTGATATCCAAGGAGATATCATGCTT<br>GGAGGCGGCTTTATGCGGTCGCTAAAGAAGGGCGTCGACCAAATTGGACTTTATG<br>ACGACGGTGATATTCTTGAGCCTCTGACCATTTCGCATATCTCAGGCGTGTTTCC<br>TGCAGTTTTCCATCCCAGATGGGGTGCTGGTGGCGGGTTGAAACAAGTGTGGTCT<br>GGAATTCTGGGATTGACTGGTGATTTACTTCCTCTGGTGGGCCGGCTGGATACAA<br>AATTGACAGGTCGAAATTCTCCGAGTCAGCACGCGCGTAGTGGATGCAAAGAGCAG |

TABLE 4-continued

Exemplary sequences of endophytes of the present invention

| SEQ ID | MICID | Gene/Locus | Sequence |
|---|---|---|---|
| | | | TTGTGGAGAGTGGGTTGCAGCCGGCTTCTGCGGGGAAGGCATGGTCTGGGCCTGG<br>CTTTGTGGAGTTGCTCTTGGAATTATGGTCGCTGGAACTGAGGAACACGATGTAA<br>CGAAAGCTCCTGGGAGA |
| 39 | MIC-<br>68000 | ITS | TCTTGGTCATTTAGAGGAAGTAAAAGTCGTAACAAGGTTTCCGTAGGTGAACCTG<br>CGGAAGGATCATTACCGAGTGCGGGCCCTCTGGGTCCAACCTCCCATCCGTGTCT<br>ATCTGTACCCTGTTGCTTCGGCGTGGCCACGGCCCGCCGGAGACTAACATTTGAA<br>CGCTGTCTGAAGTTTGCAGTCTGAGTTTTTAGTTAAACAATCGTTAAAACTTTCA<br>ACAACGGATCTCTTGGTTCCGGCATCGATGAAGAACGCAGCGAAATGCGATAATT<br>AATGTGAATTGCAGAATTCAGTGAATCATCGAGTCTTTGAACGCACATTGCGCCC<br>CCTGGTATTCCGGGGGGCATGCCTGTCCGAGCGTCATTGCTGCCCTCAAGCACGG<br>CTTGTGTGTTGGGCTTCCGTCCCTGGCAACGGGACGGGCCCAAAAGGCAGTGGC<br>GGCACCATGTCTGGTCCTCGAGCGTATGGGGCTTTGTCACCCGCTCCCGTAGGTC<br>CAGCTGGCAGCTAGCCTCGCAACCAATCTTTTTAACCAGGTTGACCTCGGATCAG<br>GTAGGGATACCCGCTGAACTTAAGCATATCAATAAGCGGAGGAAAAGAAACCAAC<br>CGGGATTGCCTCAGTAACGGCGAGTGAAGCGGCAAGAGCTCAAATTTGAAATCTG<br>GCCCCTCCGGGGTCCGAGTTGTAATTTGTAGAGGATGCTTCGGGTGCGGCCCCCG<br>TCTAAGTGCTCTGGAACGGGCCATCGGAGAGGGTGAGAATCCCGTCTGGGACGGG<br>GTGTCCGCGTCCATGTGAAGCTCCTTCGACGAGTCGAGTTGTTTGGGAATGCAGC<br>TCTAAATGGGTGGTAAATTTCATCTAAAGCTAAATACTGGCCGGAGACCGATAGC<br>GCACAAGTAGAGTGATCGAAAGATGAAAAGCACTTTGAAAAGAGAGTTAAACAGC<br>ACGTGAAATTGTTGAAAGGGAAGCGCTTGCGACCAGACTCGCTTCCGGGGTTCAG<br>CCGGCTTTCGGGCCGGTGTACTTCCCCGGGGCGGGCCAGCGTCGGTTTGGGCGG<br>CCGGTCAAAGGCCCCTGGAATGTAACGCCTCTCGGGGCGCCTTATAGCCAGGGGT<br>GTCATGCGGCCAGCCTGGACCGAGGAACGCGCTTCGGCACGGACGCTGGCATAAT<br>GGTCGTAAACGACCCGTCTTGAAACACGGACCAAGGAGTCTAACATCTACGCGAG<br>TGTTCGGGTGTCAAACCCGTGCGCGCAGTGAAAGCGAACGGAGGTGGGAGCCCCC<br>TCGCGGGGCGCACCATCGACCGATCCTGATGTCTTCGGATGGATTTGAGTAAGAG<br>CGTAGCTGTGGGGACCCGAAAGATGGTGAACTATGCCTGAATAGGGCGAAGCCAG<br>AGGAAACTCTGGTGGAGGCTCGCAGCGGTTCTGACGTGCAAATCGATCGTCAAAT<br>TTGGGTATAGGGGCGAAAGAC |
| 40 | MIC-<br>19994 | ITS | TCTTGGTCATTTAGAGGAAGTAAAAGTCGTAACAAGGTCTCCGTTGGTGAACCAG<br>CGGAGGGATCATTACAAGAAGCCGAAAGGCTACTTCAAACCATCGTGAACTTATC<br>CAAGTTGCTTCGGCGGCGCGGCTCCCCTCGCGGGGTGCCGCAGCCCCGCCCCCTC<br>GGGGGTGGTGGGCGCCCGCCGGAGGTATTAAACTCTCCCGTATTATAGTGGTATT<br>TCTGAGTAAAAACAAATAAGTTAAAACTTTCAACAACGGATCTCTTGGTTCTGGC<br>ATCGATGAAGAACGCAGCGAAATGCGATAAGTAATGTGAATTGCAGAATTCAGTG<br>AATCATCGAATCTTTGAACGCACATTGCGCCCGCTAGTATTCTAGCGGGCATGCC<br>TGTTCGAGCGTCATTTCAACCCTCAAGCCCTGCTTGGTGTTGGGGCCCTACGGCT<br>GCCGTAGGCCCTGAAAAGAAGTGGCGGGCTCGCTGCAACTCCGAGCGTAGTAATT<br>CATTATCTCGCTAGGGAGGCGCGGCGGTGCTCCTGCCGTTAAAGACCATCTTTAA<br>CCAAAGGTTGACCTCGGATCAGGTAGGAATACCCGCTGAACTTAAGCATATCAAT<br>AAGCGGAGGAAAAGAAACCAACAGGGATTGCCCTAGTAACGGCGAGTGAAGCGGC<br>AACAGCTCAAATTTGAAATCTGGCTTCGGCCCGAGTTGTAATTTGTAGAGGATGC<br>TTTTGGTGAGGTGCCTTCTGAGTTCCCTGGAACGGGACGCCAGAGAGGGTGAGAG<br>CCCCGTATAGTCGGCCACCGATCCTCTGTAAAGCTCCTTCGACGAGTCGAGTAGT<br>TTGGGAATGCTGCCAAAATGGGAGGTATATCTCTTCTAAAGCTAAATATAGGCC<br>AGAGACCGATAGCGCACAAGTAGAGTGATCGAAAGATGAAAAGCACTTTGAAAAG<br>AGGGTTAAATAGCACGTGAAATTGTTGAAAGGGAAGCGCTTGTGACCAGACTTGC<br>GCCGGGCTGATCATCCAGTGTTCTCACTGGTGCACTCGACCCGGCTCAGGCCAGC<br>GTCGGTTCTCGCAGGGGGATAAAAGCTTCGGGAACGTGGCACCTTCGGGTGTGTT<br>ATAGCCCGCTGCTTAATACCCCGGTGGGGACCGAGGTTCGCGCTCTGCAAGGACG<br>CTGGCATAATGGTCATCAGCGACCCGTCTTGAAACACGGACCAAGGAGTCGAGGT<br>TTTGCGCGAGTGTTTGGGTGTAAAACCCGCACGCGTAATGAAAGTGAACGTAGGT<br>GAGAGCTTCGGCGCATCATCGACCGATCCTGATGTATTCGGATGGATTTGAGTAA<br>GAGCGTATAGCCTCGGACCCGAAAGATGGTGAACTATGCCTGAATAGGGGGAAGC<br>CAGAGGAAACTCTGGTGGAGGCTCGCAGCGGTTCTGACGTGCAAATCGATCGTCA<br>AATTTGGGCA |
| 41 | MIC-<br>19994 | LSU | TCCTGAGGGAAACTTCGGCGGTAACCAGCTACTAGATGGTTCGATTAGTCTTTCG<br>CCCCCATGCCCAAATTTGACGATCGATTTGCACGTCAGAACCGCTGCGAGCCTCC<br>ACCAGAGTTTCCTCTGGCTTCACCCTATTCAGGCATAGTTCACCATCTTTCGGGT<br>CCGAGGCTATACGCTCTTACTCAAATCCATCCGAATACATCAGGATCGGTCGATG<br>ATGCGCCGAAGCTCTCACCTACGTTCACTTTCATTACGCGTGCGGGTTTTACACC<br>CAAACACTCGCGCAAAACCTCGACTCCTTGGTCCGTGTTTCAAGACGGGTCGCTG<br>ATGACCATTATGCCAGCGTCCTTGCAGAGCGCGAACCTCGGTCCCCACAGGGGTA<br>TTAAGCAGCGGGCTATAACACACCCGAAGGTGCCACGTTCCCGAAGCTTTTATCC<br>CCCTGCGAGAACCGACGCTGGCCTGAGCCGGGTCGAGTGCACCAGTGAGAACACT<br>GGATGATCAGCCCGGCGCAAGTCTGGTCACAAGCGCTTCCCTTTCAACAATTTCA<br>CGTGCTATTTAACCCTCTTTTCAAAGTGCTTTTCATCTTTCGATCACTCTACTTG<br>TGCGCTATCGGTCTCTGGCCTATATTTAGCTTTAGAAGAGATATACCTCCCATTT<br>TGAGCAGCATTCCCAAACTACTCGACTCGTCGAAGGAGCTTTACAGAGGATCGGT<br>GGCCGACTATACGGGGCTCTCACCCTCTCTGGCGTCCCGTTCCAGGGAACTCAGA<br>AGGCACCTCACCAAAAGCATCCTCTACAAATTACAACTCGGGCCGAAGCCAGATT |

TABLE 4-continued

Exemplary sequences of endophytes of the present invention

| SEQ ID | MICID | Gene/Locus | Sequence |
|---|---|---|---|
| | | | TCAAATTTGAGCTGTTGCCGCTTCACTCGCCGTTACTAGGGCAATCCCTGTTGGT<br>TTCTTTTCCTCCGCTTATTGATATGCTTAAGTTCAGCGGGTA |
| 42 | MIC-<br>19994 | SSU | CTTCCGTCAATTTCTTTAAGTTTCAGCCTTGCGACCATACTCCCCCCAGAACCCA<br>GAAACTTTACTTTCGTGTAAGGTGCCGAACGAGTCAAAATATAACATCGTCCGAT<br>CCCTAGTCGGCATAGTTTATGGTTAAGACTACGACGGTATCTGATCGTCTTCGAT<br>CCCCTAACTTTCGTTCCTGATTAATGAAAACATCCTTGGCAAATGCTTTCGCAGT<br>AGTTAGTCTTCAATAAATCCAAGAATTTCACCTCTGACAATTGAATACTGATGCC<br>CCCGACTGTCCCTATTAATCATTACGGCGGTCCTAGAAACCAACAAAATAGAACC<br>ACACGTCCTATTCTATTATTCCATGCTAATGTATTCGAGCATAGGCCTTCTTTAA<br>GCGATCTAATTTGTTCAAAGTAAAAGTCCTGGTTCCCCGACACACCCAGTGAAGG<br>GCATGCGGTTCCCCAGAGGGAAAGGCCCGGCCGGACCAGTGCACGCGGTGAGGCG<br>GACCGGCCAGCCAGGCCCAAGGTTCAACTACGAGCTTTTTAACTGCAACAACTTT<br>AATATACGCTATTGGAGCTGGAATTACCGCGGCTGCTGGCACCAGACTTGCCCTC<br>CAATTGTTCCTCGTTAAGGGATTTAAATTGTACTCATTCCAATTACAAGCCCAA<br>AAGAGCCCTGTATCAGTATTTATTGTCACTACCTCCCCGAATCGGGATTGGGTAA<br>TTTGCGCGCCTGCTGCCTTCCTTGGATGTAGTAGCCGTTTCTCAGGCTCCTTCTC<br>CGGGGTCGAGCCCTAACCCTCCGTTACCCGTTGTCACCATGGCTGGCCAAGACCC<br>AGCCGTCGAAAGTTGATAGGGCAGAAATTTGAATGAACCATCGCCGGCGCAAGGC<br>CGTGCGATTCGAGAAGTTATTATGAATCACCAGAGAGCCCCGAAGGGCATTGGTT<br>TTTAATCTAATAAATACATCCCTTCCGAAGTCGGGATTTTTAGCATGTATTAGCT<br>CTAGAATTACCACGGTTATCCAAGTAGTAAGGTACTATCAAATAAACGATAACTG<br>ATTTAATGAGCCATTCGCAGTTTCGCGGTATAATTGCTTATACTTAGACATGCAT<br>GGCTTAATCTTTGAGACAAGCATATGACTACTGGCAGAATCAACCAGGTAA |
| 43 | MIC-<br>19994 | Unique<br>genomic<br>19994 | TGCTGGTAGTGCGAATGAAAATGGCTGGTTCCAGGATATAACGGGTAATCGACTG<br>CACTTTAACAAGGCTATGCGAGTACTTTGCGACCATGGTCTTGCAGAAGCAGATC<br>CGCCGACGAAAGAGCACGGTTCGGAGTCTGGAGGGTACAGTGTGCACGGATGTGT<br>GCACTCCTGGATGGTAAACGTCCTCAACCAGACAGGAGATGCGGAGATGGCACGT<br>CTGGCTTTGAGGTGTGTGGCTAGCCATGTGCCAAGCACGGAGGAGGGTGAGTATT<br>GGCGGGTACAGCGGCGCCTCCTTCTGCACGCAGACCAATGCTTGAAATTGATGGA<br>AGAGGGTCAGGAGGAGGAAGGCAATGGATGGGTATTCCATAATCTAGGAGATCTC<br>TACAAAGCCCAAGGGCGGTTCAAGGAAGCAGAAGCCATGTACGAGCGGGCGCTTC<br>GAGGCAAGGAGAAGGCATGGGGACCAGACCACACGTCGACACTCGACACAGTCAA<br>CAATCTGGGTCTCGTCGCCGACAACAAAGCCAGCCACACCAAACATCAAGTTCCA<br>TTCTCGTTCCCCGTCTTTGTCGTGTGGCAGACAAAACCTGATGGAACCCGAAAG |
| 44 | MIC-<br>99023 | ITS | TGGTCATTTAGAGGAAGTAAAAGTCGTAACAAGGTCTCCGTTGGTGAACCAGCGG<br>AGGGATCATTATAGAGTTTTCTAAACTCCCAACCCATGTGAACTTACCATTGTTG<br>CCTCGGCAGAAGCTACCTGGTTACCTTACCTTGGAACGGCCTACCCTGTAGCGCC<br>TTACCCTGGAACGGCCTACCCTGTAACGGCTGCCGGTGGACTACCAAACTCTTGT<br>TATTATATTGTAATCTGAGCGTCTTATTTTAATAAGTCAAAACTTTCAACAACGG<br>ATCTCTTGGTTCTGGCATCGATGAAGAACGCAGCGAAATGCGATAAGTAATGTGA<br>ATTGCAGAATTCAGTGAATCATCGAATCTTTGAACGCACATTGCGCCCATTAGTA<br>TTCTAGTGGGCATGCCTGTTCGAGCGTCATTTCAACCCTTAAGCCTAGCTTAGTG<br>TTGGGAGCCTACTGCTTTTGCTAGCGGTAGCTCCTGAAATACAACGGCGGATCTG<br>CGATATCCTCTGAGCGTAGTAATTTTTATCTCGCTTTTGACTGGAGTTGCAGCGT<br>CTTTAGCCGCTAAACCCCCCAATTTTTAATGGTTGACCTCGGATCAGGTAGGAAT<br>ACCCGCTGAACTTAAGCATATCAATAAGCGGAGGAAAAGAAACCAACAGGGATTG<br>CCTTAGTAACGGCGAGTGAAGCGGCAACAGCTCAAATTTGAAATCTGGCCCTCGG<br>GTCCGAATTGTAATTTGTAGAGGATGATTTTGGTGCGGTATCTTCCGAGTTCCTT<br>GGAACAGGACGCCTTAGAGGGTGAGAGCCCCGTACGGTTGAATGCCTAGCCTCTG<br>TAAATCTCCTTCGACGAGTCGAGTAGTTTGGGAATGCTGCTCTAAATGGGAGGTA<br>AATTTCTTCTAAAGCTAAATATTGGCCAGAGACCGATAGCGCACAAGTAGAGTGA<br>TCGAAAGATGAAAAGCACTTTGAAAAGAGGGTTAAATAGCACGTGAAATTGTTGA<br>AAGGGAAGGATTTGTGACCAGACTTTTTCTGGGCGGATCATCCGGGGTTCTCTCC<br>GGTGCACTTTGCCCAGTAAAGGCCAGCATCGATTTTCGGCGGCGGATAAAAGCAG<br>TGGGAATGTGGCTCCCTACGGGGAGTGTTATAGCCCATTGTATAATACGCTGCTG<br>GGGATCGAGGTACGCGCTTCTGCAAGGATGCTGGCGTAATGGTTATCAATCACCC<br>GTCTTGAAACACGGACCAAGGAGTCGAACATTTATGCGAGTGTTTGGGTGTTAAA<br>CCCTCACGCGTAATGAAAGTGAACGGAGGTGAGAGCCCGTACGGGTGCATCATCG<br>ACCGATCCTGAAGTTTTCGGATGGATTTGAGTAAGAGCATAACTGTTCGGACCCG<br>AAAGATGGTGAACTATGCGTGGATAGGGTGAAGCCAGAGGAAACTTGGTGGAGG<br>CTCGCAGCGGTTCTGACGTGCAAATCGATCGTCAAATCTGCGCATGGGGCGAAA<br>G |
| 45 | MIC-<br>99023 | Unique<br>genomic<br>region | CCAGTTTCCTGTCCACCAAGGTGGCAGTCGACGCATTCACAGAATGCTTCACTGG<br>CGCATCCTGCACGACCCCAGCGACGAGCGCCGCGCCCTCGGCAACTTCTACTGCC<br>TCGACGTCGTCAGGAGCAAGCACCTCTAGCGCGGCAGCATCGGGGTCCAGCTCGG<br>GGTCCAGCGGCCTCTCCACGGGCGCCATCGTCGGCATCGCCGTCGCCTGCGGCGT<br>CGTGGGCCTGGCCCTGATCGGCGCGCCGTCTGGTTCCTGTGCTTCGCCGCCGCGG<br>CGCCGCCACGGCGACCACTCGGCCCTGGCGCAGCAGCAGCAGTTACAAAACGGCA<br>GCTACAACATGTCGGACGGCGGCTGCCCCACAAGGCCGGCATGATGATGACGCG<br>CAGCGACAAGGACCTGCCACACGTCGCCACCGACAGCCCGCAGTCGGCGTACGCC<br>CCGAGCCGCGTGCTGCGCGACTCGATGGGCAGCGGGGCCGTCGGGGCCGGCCTGA<br>TGAGCGGGAACGGCAACGACCACGTCCACGTCCACCACCACCACCACCAGCACGC |

TABLE 4-continued

Exemplary sequences of endophytes of the present invention

| SEQ ID | MICID | Gene/Locus | Sequence |
|---|---|---|---|
| | | | CAGCGTCGACATGGACCACGGCGGCGAGAGCGAAAACGACAACAACAACAACAAC<br>GCCTA |
| 46 | MIC-<br>99023 | 60S<br>ribosomal<br>protein L<br>10 | CTTCAGCTGGAACTTGATGGTGGACTTGACCTCGTTGATCCTGCCAGTAAGGTCG<br>TCGGAGTGGGAGACAGGGGTAGGGAACTTGCCGGCTGTGAGGGTTCCAAGTTAGTA<br>CAAGTCAAGAGGATCAGAACTGAAAGTGTCGCGACTTACCCTTGGACAGACCAGG<br>ACCCAAGAGACGGGGGATCTGCTTGATCAGAGAGTCCGAAGCGACGAAAGCATCG<br>TACTTGCGAGCGAGCTTCTTGATCAGCTTCTTGTTCTTGTTCAGCTTCTTCAGGT<br>CATCGGCGCTCATCTAGGTCGCGTATTAGCTCGGCTGACATGCCCATTGAAAACT<br>GTGTATCTTACGGCGTCGACACCACCGTGCTTGGCACGGTCGAGATCGTGCTGGT<br>CACCAAGAATGCAGATGGCCATGTTGGGGCGGGGGATGGTCGGCAGGCGGACGGT<br>ACCCGAGAAACGCTTGTCACG |
| 47 | MIC-<br>99023 | RPB2 | CCCATGGCTTGTTTACCCATGGCCGACTGGTAAGTGTTACGAGGAGACTGTAGAT<br>TGGGTCAGTTTTGAATTGCACAGCGCGGGATTCCTTGTGAACTTACCTGGTTGTG<br>ATCTGGGAACGGAATGATGCTTGCGCAAATACCCAGCAGCATGCTCGGATGGATC<br>TCGCAATGGGTGTACATGTGCGTGGTAGGGTTGAGCTTTGTCTTCAATCTGGCAT<br>TGAGATCCTCGCCCACATCCTGGCTGACATCGATGCCCTGCTTGGCTAGTCGATA<br>AGTTTCCAAATCTTCAGGCGTCATGCAGATCATGGCGGTCTCTTCTTCTTCGGCA<br>TCAAGGTATTCAATGACTCCCTCGTTGACAAGACCTTGCCAGCCGAAAAAGTCCT<br>CGCTGCCGGGGGGAAGCGTAGCGTCTCGTTCCAGACGTCGGATCATGTCCTTGTT<br>GAGAACCAAATTGCCAGCTTCGACACCGCGGTCGGGGTCGTCCTCCTGTTCCACA<br>ACGAACAGCGGGCGCATGACACGCCCTGCGTCGGAGAAAATCTTGAACTCGCGGT<br>CGCGAATGTCGCGGACCAGGGAAACCTCGGCAGGAATTTGGTTACTACGCCGGAG<br>CTGCTGAACATCCCTAACTAGAGCCTTGGGGTCCTGGTGAACACCAATCCAGGAT<br>CCGTTGAGGAAGATCTTGGTAGCGTTGGGATAACGCACGGCATCATACTCTTCGA<br>GTACTTCCATGTTTCTAGTAATCATGTAGTCGATGATAGGTTCCGTGCTAGTACC<br>CACACTCACAGAGCACATGAGGGACAGATTCTTGACAAGACCACAGGCCTGACCT<br>TCTGGCGTCTCTGCAGGACACACCAAGCCCCAATGCGTGTTGTGCAGCTGGCGAG<br>GCTTTGCAAGTTTTCCGTCACGTCCAATGGGCGTGTTTGTTCGTCGCAAATGGGA<br>TAGTGTAGATGCAAAGGTATATCTGTTCAAGACCTGCGAGACACCAGCTGTCGAG<br>CTCATGGCCTTCTTCTGGTCGCCCCAGTTTCCAGTGGCGAGAGAGTACTTCAGAC<br>CGTTCGTGACAATACCAGACTTGATACCGAACTGGACCTGGAAGTCCTTGTTCTG<br>CTCAACACAACGTTTGAGAGTCATCGTGATCTCGTTGGTGAGCTTCCGAACAATG<br>TTGCGGAAGAGCTTGGCAAGTAGGGGGCCGGCCAGATCCAGACGCTTCTTGCCAA<br>AGTGATCACGATCGTCC |
| 48 | MIC-<br>99023 | Beta-tubulin | GTTCACCTCCAGACCGGTCAATGCGTAAGTACATGCCAAATCCCGCGATAGCGTG<br>CCCAAAACACCAGAGCTCACATTCACCAACAGGGTAACCAAATTGGTGCTGCCTT<br>TTGGTATGTAGCCCATCTACCTCGACACGCCTCAATACGACAACCCCCCGCAACT<br>CGACAACGACGTTCTCAACAAGTGCTTGCTTGGAAACAAGGGAAAGACTTGATAC<br>TGACCGGTCCCTGATAGGCAAACCATCTCTGGCGAGCACGGTCTCGACAGCAATG<br>GAGTGTACGTACCCTTTCCTTGGCTACTTGCTTTCCCACGAACATCTCAGCTAAC<br>ACTCGTGGTTGTTCAGCTACAACGGTACCTCCGAGCTCCAGCTCGAGCGCATGAG<br>CGTCTACTTCAACGAGGCTTCCGGCAACAAGTACGTTCCTCGTGCCGTCCTCGTC<br>GATCTCGAGCCCGGTACCATGGATGCCGTCCGCGCCGGTCCTTTCGGTCAGCTCT<br>TCCGCCCTGACAACTTCGTCTTCGGTCAGTCCGGT |
| 49 | MIC-<br>82330 | fusA | TCGCGTTCGTTAACAAAATGGACCGCATGGGCGCTAACTTCCTGAAAGTTGTTGA<br>TCAGATCAAAACCCGTCTGGGCGCGAACCCGGTTCCGCTGCAGCTGGCAATTGGC<br>GCTGAAGAAGGTTTCACCGGTGTTGTTGACCTGGTGAAAATGAAAGCGATCAACT<br>GGAACGATGCTGACCAGGGCGTTACCTTCGTTTACGAAGATATCCCGGCTGAGAT<br>GCAGGACCTGGCTGACGAATGGCACCAGAACCTGATCGAATCTGCGGCGGAAGCT<br>TCAGAAGAGCTGATGGAGAAATACCTGGGTGGTGAAGACCTGACTGAAGAAGAGA<br>TCAAAACTGCTCTTCGTCAGCGTGTTCTGAACAACGAAATCATCCTGGTAACCTG<br>TGGTTCTGCGTTTAAGAACAAAGGCGTTCAGGCGATGCTGGATGCGGTAATTGAT<br>TACCTGCCGTCCCCGACTGACGTTCCGGCGATCAACGGTATGCTGGACGATGGTA<br>AAGATACCCCGGCCGAGCGTCACGCAAGCGACGAAGAGCCGTTCTCTGCACTGGC<br>GTTCAAAATCGCAACTGACCCGTTCGTAGGTAACCTGACCTTCTTCCGCGTGTAC<br>TCCGGTGTGGTTAACTCTGGTGATACCGTACTGAACTCCGTGAAATCTGCACGTG<br>AGCGTTTCGGTCGTATCGTTCAGATGCACGCTAACAAACGTGAAGAGATCAAAGA<br>AGTTCGCGCGGGCGATATCGCTGCAGCGATCGGTCTGAAAGACGTGATCACCGGT<br>GACACCCTGTGTGATCCGGACAACCCGATCATTCTGGAGCGTATGGAATTCCCGG<br>AGCCGGTAATCTCCATCGCTGTAGAACCGAAAACCAAAGCTGACCAGGAAAAAT<br>GGGTCTGGCTCTGGGCCGTCTGGCTAA |
| 51 | MIC-<br>82330 | unique<br>genomic<br>region | ACGATCTCGGCGGGTAATAACCCTGCACCGCGATGCAGGCACGTAGTGCGATCTG<br>CGGTGACAGCGTGTTGATGGGCGTGGCTGCGCCAGTGTTGTTCACCGTCGCAGTT<br>GCGCCAGCCATACTCATTGTCACACCGGCCAGCGGGACCTGTGTGCCGCCCGCAG<br>GCGCATAAATACTTGTTCCCGGGTTTTGTGTTGCCGCCAGTCGGTTGTTAGTTGC<br>TGACGGGGTATTGGATACACCCGGAGCAGTTGTCGCACTGATAGAAAACGCGCCA<br>GTTCCGAGCATCGCCTGGTGAGAATGGACCGGCATCTGAGAGATGCTCATTACAG<br>CCGTTTCCGCACCGCGCGTCTGCCCCAGCGATAGCACATTGTTATTGGGCCCAAC<br>ACCGGCTCCGACCGGGCTTCTGCCTCGCATATCCGGCAGATTAAAGGAGGTATTC<br>GCCGTCGATGAAGGGGTATAAAGGCGGGTAATTAGGGAATACAACGCCTGGGATT |

TABLE 4-continued

Exemplary sequences of endophytes of the present invention

| SEQ ID | MICID | Gene/Locus | Sequence |
|---|---|---|---|
| | | | GTTGTACTGGAATCGTCTGACCGTTCGCTTCCAGGTAGCCGCGCGGACAAAAGCT<br>TGCTGCTGTAAAGCAAACCGCGCCAACATAGGGCTCCGAAC |

MIC-15870 was deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-67466.

MIC-84414 was deposited with the Agricultural Research Service Culture Collection (NRRL), at the U.S. Department of Agriculture, 1815 North University Street, Peoria, Illi. 61604, under the terms of the Budapest Treaty, as Deposit ID: NRRL-67467.

MIC-82330 was deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-B67465.

Example 2

Isolation and Identification of Endophytes Using Marker Gene Sequences

Bacterial endophytes described herein were further characterized by the sequence of the marker gene elongation factor G. PCR amplification of the elongation factor G gene using primer sequences fusA-f2 (SEQ ID NO: 30) and fusA-r2 (SEQ ID NO: 31) is described in Miyoshi-Akiyama T, Hayakawa K, Ohmagari N, Shimojima M, Kirikae T (2013) Multilocus Sequence Typing (MLST) for Characterization of Enterobacter cloacae. PLoS ONE 8(6): e66358. doi:10.1371/journal.pone.0066358. The sequence of elongation factor G in MIC-82330 is SEQ ID NO: 49.

Endophytes described herein can be identified by the sequence of one or more of the following loci: long subunit rRNA (LSU), small subunit rRNA (SSU), second largest subunit of RNA polymerase II (RPB2), beta-tubulin, 60S ribosomal protein L 10. PCR amplification of the LSU using primer sequences LROR (SEQ ID NO: 26 and SEQ ID NO: 26) and LR5 (SEQ ID NO: 27 and SEQ ID NO: 27) is described in Stielow J B, Lévesque C A, Seifert K A, et al. One fungus, which genes? Development and assessment of universal primers for potential secondary fungal DNA barcodes. Persoonia: Molecular Phylogeny and Evolution of Fungi. 2015; 35:242-263. doi:10.3767/003158515X689135. PCR amplification of the SSU using primer sequences SR1R (SEQ ID NO: 29) and NS4 (SEQ ID NO: 28) is described in Zhu et al. (2016) Helminthosporium velutinum and H. aquaticum sp. nov. from aquatic habitats in Yunnan Province, China. Phytotaxa 253 (3): 179-190. PCR amplification of second largest subunit of RNA polymerase II (RPB2) using primer sequences fRPB2-5F (SEQ ID NO: 22) and bRPB2-7.1R (SEQ ID NO: 19) is described in Riess K, Oberwinkler F, Bauer R, Garnica S. High genetic diversity at the regional scale and possible speciation in Sebacina epigaea and S. incrustans. BMC Evolutionary Biology. 2013; 13:102. doi:10.1186/1471-2148-13-102. PCR amplification of second largest subunit of RNA polymerase II (RPB2) using primer sequences fRPB2-5F (SEQ ID NO: 22) and fRPB2-7R (SEQ ID NO: 23) is described in Liu Y, Whelen S, Hall B. Phylogenetic relationships among ascomycetes: evidence from an RNA polymerase II subunit. Mol. Biol. Evol. 1999. 16(12): 1799-1808. PCR amplification of beta-tubulin using primer sequences Btub2Fd (SEQ ID NO: 20) and Btub4Rd (SEQ ID NO: 21) is described in Aveskamp et al. (2009) DNA phylogeny reveals polyphyly of Phoma section Peyronellaea and multiple taxonomic novelties Mycologia, 101(3):363-382. PCR amplification of the gene encoding 60S ribosomal protein L 10 using primer sequences 60S-506F (SEQ ID NO: 24) and 60S-908R (SEQ ID NO: 25) is described in Stielow et al. 2015.

MIC-84414 can be identified by the sequence of one or more of the following: RPB2 sequence (SEQ ID NO: 35), RPB2 sequence (SEQ ID NO: 36), beta-tubulin sequence (SEQ ID NO: 37). MIC-19994 can be identified by the sequence of one or more of the following: its LSU sequence (SEQ ID NO: 41), SSU sequence (SEQ ID NO: 42). MIC-99023 can be identified by the sequence of one or more of the following: the gene encoding 60S ribosomal protein L 10 (SEQ ID NO: 46), RPB2 sequence (SEQ ID NO: 47), beta-tubulin sequence (SEQ ID NO: 48).

Example 3

Isolation and Identification of Bacterial and Fungal Endophytes

Classification of the bacterial strains using its 16S sequence was done by the following methodology.

To accurately characterize isolated bacterial endophytes, colonies were submitted for marker gene sequencing, and the sequences were analyzed to provide taxonomic classifications. Colonies were subjected to 16S rRNA gene PCR amplification using a primer pair 27f (5'-AGAGTTT-GATYMTGGCTCAG-3') (SEQ ID NO: 1) and 1492r (5'-GGTTACCTTGTTACGACTT-3') (SEQ ID NO: 2). Sequencing reactions were performed using primers: 27f (5'-AGAGTTTGATYMTGGCTCAG-3') (SEQ ID NO: 1), 515f (5'-GTGYCAGCMGCCGCGGTAA-3') (SEQ ID NO: 3), 806r (5'-GGACTACNVGGGTWTCTAAT-3') (SEQ ID NO: 4), and 1492r (5'-GGTTACCTTGTTACGACTT-3') (SEQ ID NO: 2). Preferably sequencing primers are chosen so that overlapping regions are sequenced. Sanger sequencing of was performed at Genewiz (South Plainfield, N.J.). Raw chromatograms were converted to sequences, and corresponding quality scores were assigned using Trace-Tuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C., 2010) with option search_global, then for all best match hits, returns lowest taxonomic rank shared by all best hits for a query), RDP Naive Bayesian rRNA Classifier version 2.11, September 2015 (Wang et al., 2007), SPINGO version 1.3 (32 bit)

(Allard et al. (2015) BMC Bioinformatics 16:324 DOI: 10.1186/s12859-015-0747-1), and UTAX version v8.1.1861_i86linux64 (Edgar, R. C. (2016) available online at drive5.com/usearch/manual/utax_algo.html), using reference databases: RDP 16S rRNA training set 15 (Cole et al., 2014), and SILVA version 119 (Quast et al., 2013). The classifier and database combinations listed in Table 3 were used to assign taxonomy to bacterial sequences.

TABLE 5

The classifier and database combinations used to classify 16S sequences

| Classifier | Database |
| --- | --- |
| LCA | SILVA, version 119 |
| RDP | RDP, 16S rRNA training set 15 |
| SPINGO | RDP, 16S rRNA training set 15 |
| UTAX | RDP, 16S rRNA training set 15 |
|  | SILVA, version 119 |

Classification of the fungal strain using ITS sequences was done by the following methodology.

Total genomic DNA was extracted from individual fungal isolates, using the DNeasy Plant Mini Kit (Qiagen, Germantown, Md.). Polymerase Chain Reaction (PCR) was used to amplify a genomic region including the nuclear ribosomal internal transcribed spacers (ITS) using a primer pair ITS_1 (5'-CTTGGTCATTTAGAGGAAGTAA-3') (SEQ ID NO: 5) and LR5 (5'-TCCTGAGGGAAACTTCG-3') (SEQ ID NO: 8). Each 25 microliter-reaction mixture included 22.5 microliters of Invitrogen Platinum Taq supermix, 0.5 microliter of each primer (10 uM), and 1.5 microliters of DNA template (~2-4 ng). Cycling reactions were run with MJ Research PTC thermocyclers and consisted of 94° C. for 5 min, 35 cycles of 94° C. for 30 s, 54° C. for 30 s, and 72° C. for 1 min, and 72° C. for 10 min. Sanger sequencing of was performed at Genewiz (South Plainfield, N.J.) using primers: ITS_1 (5'-CTTGGTCATTTAGAGGAAGTAA-3') (SEQ ID NO: 5), ITS_2 (5'-GCTGCGTTCTTCATC-GATGC-3') (SEQ ID NO: 6), ITS_3 (5'-GCATCGAT-GAAGAACGCAGC-3') (SEQ ID NO:7), and LR5 (5'-TCCTGAGGGAAACTTCG-3') (SEQ ID NO: 8). Sequencing primers were chosen so that overlapping regions were sequenced. Raw chromatograms were converted to sequences, and corresponding quality scores were assigned using TraceTuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C., 2010) with option search global, then for all best match hits, returns lowest taxonomic rank shared by all best hits for a query), SPINGO (Allard et al., 2015), and UTAX (Edgar, R. C., 2016), using the WARCUP Fungal ITS trainset 1 (Deshpande et al. (2016) Mycologia 108(1):1-5) and UNITE (Koljalg et al., 2013). The classifier and database combinations listed in Table 4 were used to assign taxonomy to fungal sequences.

TABLE 6

The classifier and database combinations used to classify ITS sequences.

| Classifier | Database |
| --- | --- |
| LCA | UNITE, Fungal ITS trainset Jul. 4, 2014 |
| RDP | UNITE, Fungal ITS trainset Jul. 4, 2014 |
|  | WARCUP, Fungal ITS trainset 1 |
| SPINGO | UNITE, Fungal ITS trainset Jul. 4, 2014 |
| UTAX | UNITE, Fungal ITS trainset Jul. 4, 2014 |
|  | WARCUP, Fungal ITS trainset 1 |

TABLE 7

Taxonomic classification of endophytes of the present invention

| SEQ ID Nos. | MIC ID | Phylum | Class | Order | Family | Genus | Species |
| --- | --- | --- | --- | --- | --- | --- | --- |
| 32, 33 | MIC-15870 | Ascomycota | Dothideomycetes | Pleosporales | Periconiaceae | *Periconia* | *macrospinosa* |
| 34, 35, 36, 37, 38 | MIC-84414 | Ascomycota | Dothideomycetes | Pleosporales | Pleosporaceae | *Curvularia* | *spicifera* |
| 39 | MIC-68000 | Ascomycota | Eurotiomycetes | Eurotiales | Aspergillaceae | *Aspergillus* | *ruber* |
| 40, 41, 42, 43 | MIC-19994 | Ascomycota | Sordariomycetes | Coniochaetales | Coniochaetaceae | *Coniochaeta* | *prunicola* |
| 44, 45, 46, 47, 48 | MIC-99023 | Ascomycota | Sordariomycetes | Xylariales | Sporocadaceae | *Pestalotiopsis* | *neglecta* |
| 49, 50, 51 | MIC-82330 | Proteobacteria | Gamma Proteobacteria | Enterobacteriales | Enterobacteriaceae | *Enterobacter* | *cowanii* |

Example 4

Assessment of Improved Plant Characteristics, Seedling Vigor

Assay of Soy Seedling Vigor

Seed preparation: The lot quality of soybean seeds was first assessed by testing germination of 100 seeds. Seeds were placed, 8 seeds per petri dish, on filter paper in petri dishes, 12 mL of water was added to each plate and plates are incubated for 3 days at 24° C. The percent germination was greater than 95%. One thousand soybean seeds were then surface sterilized by co-incubation with chlorine gas in a 20×30 cm container placed in a chemical fume hood for 16 hours. Percent germination of 50 seeds, per sterilization batch, was tested as above and confirmed to be greater than 95%.

Preparation and heterologous disposition of endophytes: Spore solutions were made by rinsing and scraping spores from agar slants which have been growing for about 1 month. Rinsing was done with 0.05% Silwet. Solutions were passed through Miracloth to filter out mycelia. Spores per ml were counted under a microscope using a hemocytometer. The stock suspension was then diluted into 10^6 spores/ml average root area of treated soybean seedlings relative to untreated soybean seedlings. Results are summarized in Table 8.

TABLE 8

Plant vigor of endophyte and control treated soybean seedlings

| Treatment | Average Root Length, cm | Stnd. Dev. Root Length | Average Root Area, cm | Stnd. Dev. Root Area | Root Length, % difference NT | Root Area, % difference NT |
|---|---|---|---|---|---|---|
| Control | 79.44 | 32.49 | 8.94 | 4.14 | 0.00 | 0.00 |
| MIC-15870 | 97.79 | 30.41 | 12.56 | 4.71 | 23.10 | 40.53 |
| MIC-84414 | 88.26 | 28.01 | 10.64 | 3.27 | 11.09 | 19.07 | utilizing water. 3 µl of spore suspension was used per seed (~10^3 CFUs/seed is obtained). Control treatments were prepared by adding equivalent volumes of sterile water to seeds.

Assay of seedling vigor: Two rolled pieces of germination paper were placed in a sterile glass gar with 50 mL sterile water, then removed when completely saturated. Then the papers were separated and inoculated seeds were placed at approximately 1 cm intervals along the length of one sheet of moistened germination paper, at least 2.5 cm from the top of the paper and 3.8 cm from the edge of the paper. The second sheet of was placed on top of the soy seeds and the layered papers and seeds were loosely rolled into a tube. Each tube was secured with a rubber band around the middle and placed in a single sterile glass jar and covered loosely with a lid. For each treatment, three jars with 15 seeds per jar were prepared. The position of jars with the growth chamber was randomized. Jars were incubated at 60% relative humidity, and 22° C. day, 18° C. night with 12 hours light and 12 hours dark for 4 days and then the lids were removed and the jars incubated for an additional 7 days. Then the germinated soy seedlings were weighed and photographed and root length and root surface area scored as follows.

Dirt, excess water, seed coats and other debris was removed from seedlings to allow accurate scanning of the roots. Individual seedlings were laid out on clear plastic trays and trays were arranged on an Epson Expression 11000XL scanner (Epson America, Inc., Long Beach Calif.). Roots were manually arranged to reduce the amount of overlap. For root measurements, shoots were removed if the shape of the shoot causes it to overlap the roots.

The WinRHIZO software version Arabidopsis Pro2016a (Regents Instruments, Quebec Canada) was used with the following acquisition settings: greyscale 4000 dpi image, speed priority, overlapping (1 object), Root Morphology: Precision (standard), Crossing Detection (normal). The scanning area was set to the maximum scanner area. When the scan was completed, the root area was selected and root length and root surface area were measured.

Statistical analysis was performed using R (R Core Team, 2016. R: A language and environment for statistical computing. R Foundation for Statistical Computing, Vienna, Austria. R-project.org/).

The endophyte treatment comprising MIC-15870 resulted in an increase of 23% in average root length of treated soybean seedlings and an increase of 40.5% in average root area of treated soybean seedlings relative to untreated soybean seedlings. The endophyte treatment comprising MIC-84414 resulted in an increase of 11% in average root length of treated soybean seedlings and an increase of 19% in Assay of Corn Seedling Vigor Seed preparation: The lot quality of corn seeds is first evaluated for germination by transfer of 100 seeds and with 3.5 mL of water to a filter paper lined petri dish. Seeds are incubated for 3 days at 24° C., and to ensure that percent germination is greater than 95%. One thousand corn seeds are then surface sterilized by co-incubation with chlorine gas in a 20×30 cm container in a chemical fume hood for 12 hours. Percent germination of 50 seeds, per sterilization batch, is tested as above and confirmed to be greater than 95%.

Optional reagent preparation: 7.5% PEG 6000 (Calbiochem, San Diego, Calif.) is prepared by adding 75 g of PEG to 1000 mL of water, then stirred on a warm hot plate until the PEG is fully dissolved. The solution is then autoclaved.

Preparation and heterologous disposition of endophytes: Spore solutions are made by rinsing and scraping spores from agar slants which have been growing for about 1 month. Rinsing is done with 0.05% Silwet. Solutions are passed through Miracloth to filter out mycelia. Spores per ml are counted under a microscope using a hemocytometer. The stock suspension is then diluted into 10^6 spores/ml utilizing water. 3 µl of spore suspension is used per seed (~10^3 CFUs/seed is obtained). Control treatments are prepared by adding equivalent volumes of sterile water to seeds.

Assay of seedling vigor: Either 25 ml of sterile water (or optionally, 25 ml of PEG solution as prepared above) is added to each Cyg™ germination pouch (Mega International, Newport, Minn.) and place into pouch rack (Mega International, Newport, Minn.). Sterile forceps are used to place corn seeds prepared as above into every other perforation in the germination pouch. Seeds are fitted snugly into each perforation to ensure they did not shift when moving the pouches. Before and in between treatments forceps are sterilized using ethanol and flame and workspace wiped down with 70% ethanol. For each treatment, three pouches with 15 seeds per pouch are prepared. The germination racks with germination pouches are placed into plastic tubs, and covered with perforated plastic wrap to prevent drying. Tubs are incubated at 60% relative humidity, and 22° C. day, 18° C. night with 12 hours light and 12 hours dark for 6 days to allow for germination and root length growth. Placement of pouches within racks and racks/tubs within the growth chamber is randomized to minimize positional effect. At the end of 6 days the corn seeds are scored manually for germination, root and shoot length.

Statistical analysis is performed using R (R Core Team, 2016. R: A language and environment for statistical computing. R Foundation for Statistical Computing, Vienna, Austria. R-project.org/).

Assay of Wheat Seedling Vigor

Seed preparation: The lot of wheat seeds was first evaluated for germination by transfer of 100 seeds and with 8 mL of water to a filter paper lined petri dish. Seeds were incubated for 3 days at 24° C., and percent germination was greater than 95%. Wheat seeds were then surface sterilized by co-incubation with chlorine gas in a 20×30 cm container in a chemical fume hood for 12 hours. Percent germination of 50 seeds, per sterilization batch, was tested as above and confirmed to be greater than 95%.

Reagent preparation: 7.5% polyethylene glycol (PEG) was prepared by adding 75 g of PEG to 1000 mL of water, then stirring on a warm hot plate until the PEG is fully dissolved. The solution was then autoclaved.

Preparation and heterologous disposition of endophytes: Spore solutions were made by rinsing and scraping spores from agar slants which had been growing for about 1 month. Rinsing was done with 0.05% Silwet. Solutions were passed through Miracloth to filter out mycelia. Spores per ml were counted under a microscope using a hemocytometer. The stock suspension was then diluted into $10^6$ spores/ml utilizing water. 3 µl of spore suspension was used per seed (~$10^3$ CFUs/seed was obtained). Seeds and spores were combined a 50 mL falcon tube and gently shaken for 5-10 seconds until thoroughly coated. Control treatments were prepared by adding equivalent volumes of sterile water to seeds.

Assay of seedling vigor: Petri dishes were prepared by adding four sheets of sterile heavy weight seed germination paper, then adding 50 mL of PEG solution as prepared above to each plate then allowing the liquid to thoroughly soak into all sheets. The sheets were positioned and then creased so that the back of the plate and one side wall were covered, two sheets were then removed and placed on a sterile surface. Along the edge of the plate across from the covered side wall 15 inoculated wheat seeds were placed evenly at least one inch from the top of the plate and half an inch from the sides. Seeds were placed smooth side up and with the pointed end of the seed pointing toward the side wall of the plate covered by germination paper. The seeds were then covered by the two reserved sheets, and the moist paper layers smoothed together to remove air bubbles and secure the seeds, and then the lid was replaced. For each treatment, at least three plates with 15 seeds per plate were prepared. The plates were then randomly distributed into stacks of 8-12 plates and a plate without seeds was placed on the top. The stacks were incubated at 60% relative humidity, and 22° C. day, 18° C. night with 12 hours light and 12 hours dark for 24 hours, then each plate was turned to a semi-vertical position with the side wall covered by paper at the bottom. The plates were incubated for an additional 5 days, then wheat seeds scored manually for germination, root and shoot length.

Statistical analysis was performed using R (R Core Team, 2016. R: A language and environment for statistical computing. R Foundation for Statistical Computing, Vienna, Austria. R-project.org/).

The endophyte treatment comprising MIC-19994 resulted in an increase of 13% in average root length of treated wheat seedlings. The endophyte treatment comprising MIC-84414 resulted in an increase of 40% in average root length of treated wheat seedlings. Results are shown in Table 9.

TABLE 9

Plant vigor of endophyte and control treated wheat seedlings.

| | Root Length, % difference NT Wheat |
|---|---|
| MIC-19994 | 13.2 |
| MIC-84414 | 40.2 |

Example 5

Methods of Culture Preparation of Endophytes for Greenhouse Experiments

Method 1

MIC-84414 and MIC-19994 were grown for 5-7 days in liquid culture utilizing molasses yeast extract broth (MYE). Biomass from these cultures was filtered to remove spent broth, and the resulting fungal material was air dried and ground through a 40 µm mesh.

Method 2

MIC-84414 and MIC-19994 were produced by solid state fermentation and subsequent spore preparations to remove growth substrate.

Method 3

MIC-84414 and MIC-19994 were produced by growing on agar-based medium for up to two weeks, at which point spore preparations were made by adding 0.05% silwet to the plates and scraping with L-shape spreaders to remove fungal growth. The resulting suspensions were filtered through sterile Miracloth. The final suspensions were quantified for viable cell/spore counts by standard dilution plating.

Method 4

Biomass for MIC-15870 was produced by growing in MYE broth for 5-7 days. Biomass from the culture was filtered to remove spent broth, and the resulting fungal material was air dried and ground through 40 µm mesh.

Method 5

Biomass for MIC-99023 was produced by growing in liquid medium (PDB). The resulting biomass was homogenized by sonication (50% amplitude for 30 seconds) or in a FastPrep-24 (MP Biomedicals, Santa Ana, Calif/, USA) set to 4.5 m/s for 30 seconds.

Example 6

Inoculation of Wheat Seeds with Dry Formulations of Endophytes for Greenhouse Experiments A 2% weight/volume solution of low viscosity methylcellulose (LVMC) for the seed coatings was prepared by the following method. 20 ml of the LVMC solution is used per each kg of seed. An Erlenmeyer flask was filled with the appropriate volume of deionized water and warmed to 50 degrees Celsius on a heat plate with agitation using a stir bar. The appropriate mass of LVMC powder for the desired final concentration solution was slowly added until dissolved. The solution was autoclaved at 121 degrees Celsius at 15 PSI for 30 minutes to sterilize. Finally, the sterilized LVMC was placed on a rotary shaker (130 rpm) at room temperature for several hours to promote re-liquifying of the solution.

Talcum powder for the powdered seed coatings was prepared by the following method. Talcum powder was aliquoted into 2.8L fembach flasks and autoclaved in dry cycle (121 degrees Celsius at 15 PSI for 30 minutes) to sterilize.

For dry-formulated strains, before seed treatment, equal parts of the powdered endophyte biomass prepared in Example 5 and sterile talcum powder were mixed. Control treatments are prepared using equivalent volumes of sterile talcum powder.

Dry formulation endophyte treated seeds were prepared by first applying 2% LVMC (16.6 ml per kg of seed) to the seeds and agitating to disperse the sodium alginate evenly on the seeds. Then the endophyte/talcum powder mixture was added and the seeds were agitated to disperse the powder evenly on the seeds. Then Flo-Rite® 1706 (BASF, Ludwigshafen, Germany) was added (2.0oz/cwt seeds) and the seeds were agitated to disperse the polymer evenly on the seeds.

For liquid-formulated strains, before seed treatment, equal parts of liquid biomass and 2% LVMC were combined. The LVMC/biomass inoculum was added to seeds and agitated to disperse the treatment evenly on the seeds. Then Flo-Rite® 1706 was added (2.0oz/cwt seeds) and the seeds were agitated to disperse the polymer evenly on the seeds. Treated seeds were planted within 2-3 hours of treatment. Doses for these strains was specific to the strain and the experiment. Target application rates for MIC-99023 included 1.25^2, 1.0^1, 1.25^0, 1.0^1, 1^2, 1.25^2, 1.0^3, and 2.5^3 CFU/seed. Target application rates for MIC-84414 included 5.0^1, 1.0^1, 5.0^1, 1.0^3, 5.0^3, and 1.0^5 CFU/seed. Target application rates for MIC-19994 included 1.0^1, 1.0^3, and 1.0^5 CFU/seed. The target application rate for MIC-15870 was based on weight of biomass per weight of seed and was 12 g/kg of seed.

Example 7

Cultivation and of Endophyte-Treated Plants in Greenhouse Experiment 3

A sandy loam and a commercial potting soil (Farfard®, Agawam, Mass.) were used in this experiment. Sandy loam was mixed in a ratio of 60% loam and 40% mortar sand (Northeast Nursery, Peabody, Mass.). Prior to mixing, both planting media were sifted through a ⅜" square steel mesh screen to remove larger particles and debris. Winter wheat seeds of Variety 6 were treated with commercial fungicidal and insecticidal treatment. Seeds were heterologously disposed with the endophyte formulations and formulation control (lacking any endophyte) as described in Example 6 untreated seeds (lacking formulation and endophyte) were also planted. Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18 C temperature for day/night period and light intensity was set at 650 μMol m$^{-2}$ s$^{-1}$. Post-planting, the seeds were watered to maintain approximately 80% soil capacity.

Wheat seedlings emergence was recorded on days 4, 5, and 7 after planting, with days 4 and 5 representing early emergence percentage and day 7 representing final emergence percentage. At day 7, all pots were thinned to 3 seedlings/pot. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded.

TABLE 10

Dry shoot biomass of endophyte treated wheat seedlings grown in commercial potting soil under normal watering conditions

|  | Average dry biomass (g) | Standard deviation | Standard error of the mean | Overall % Δ untreated control |
|---|---|---|---|---|
| Untreated control | 0.274 | 0.0405 | 0.00372 | 0.00 |
| MIC-84414 | 0.249 | 0.0396 | 0.00512 | −8.93 |
| MIC-99023 | 0.283 | 0.0387 | 0.005 | 3.30 |

TABLE 11

Dry shoot biomass of endophyte treated wheat seedlings grown in sandy loam soil under normal watering conditions

|  | Average dry biomass (g) | Standard deviation | Standard error of the mean | Overall % Δ untreated control |
|---|---|---|---|---|
| Untreated control | 0.273 | 0.0405 | 0.0037 | 0.00 |
| MIC-84414 | 0.249 | 0.0396 | 0.00512 | −8.79 |
| MIC-99023 | 0.283 | 0.0387 | 0.005 | 3.66 |

Example 8

Cultivation and of Endophyte-Treated Plants in Greenhouse Experiment 4

A sandy loam and a commercial potting soil (Farfard®, Agawam, Mass.) were used in this experiment. Sandy loam was mixed in a ratio of 60% loam and 40% mortar sand (Northeast Nursery, Peabody, Mass.). Prior to mixing, both planting media were sifted through a ⅜" square steel mesh screen to remove larger particles and debris. Winter wheat seeds of Variety 6 were treated with commercial fungicidal and insecticidal treatment. Seeds were heterologously disposed with the endophyte formulations and formulation control (lacking any endophyte) as described in Example 6 except that LVMC was not used, untreated seeds (lacking formulation and endophyte) were also planted. Endophyte treatments were applied to seed in three target doses: high (10^5 CFU/seed), medium (10^4 CFU/seed), low (10^3 CFU/seed). Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18° C. temperature for day/night period and light intensity was set at 650 μMol m$^{-2}$ s$^{-1}$. Post-planting, the seeds were watered to maintain approximately 80% soil capacity.

Wheat seedlings emergence was recorded on days 4, 5, and 7 after planting, with days 4 and 5 representing early emergence percentage and day 7 representing final emergence percentage. At day 7, all pots were thinned to 3 seedlings/pot. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded The MIC-19994 treatment resulted in a 6% ($p<0.05$) increase in dry show biomass at $10^4$ CFU/seed.

Example 9

Cultivation and of Endophyte-Treated Plants in Greenhouse Experiment 5

Standard planting trays were used (Griffin,1020 standard lightweight flat, #53-3325; inside a standard tray with no holes (1020 open flat—no holes, #59-3175)). Commercial potting soil (Fafard®, Northeast Nursery, Mass., #302101) was filled into the plating trays; trays were soaked in water and water was drained before planting. Wheat seeds were heterologously disposed with the endophyte formulations and formulation control (lacking any endophyte) as described in Example 6 untreated seeds (lacking formulation and endophyte) were also planted. Each treatment contained 8 replicates of 16 seeds. Seedlings were scored for emergence over 6 days. On day 8, shoots of seedlings were harvested; dried in oven for 3 days at 80C and weighed.

All endophyte treatments increased the dry weight of Prosper seedlings relative to controls. MIC-84414, MIC-19994 and MIC-99023 increased the dry weight of seedlings in both Prosper and Briggs 5. MIC-15870 and MIC-19994 improved germination in both varieties with largest increases seed in Variety 2.

TABLE 12

Germination rate of endophyte treated wheat seedlings under normal watering conditions

|  | Prosper, Variety 2, germination rate (% change over formulation) | Briggs, Variety 5, germination rate (% change over formulation) | Overall, germination rate (% change over formulation) |
| --- | --- | --- | --- |
| MIC-15870 | 68.42 | 6.67 | 37.55 |
| MIC-19994 | 68.42 | 13.33 | 40.88 |
| MIC-99023 | 47.37 | −10 | 18.69 |

TABLE 13

Dry shoot biomass of endophyte treated wheat seedlings under normal watering conditions

|  | Prosper, Variety 2, dry shoot weight (% change over formulation) | Briggs, Variety 5, dry shoot weight (% change over formulation) | Overall, dry shoot weight (% change over formulation) |
| --- | --- | --- | --- |
| MIC-15870 | 23.34 | −1.10 | 11.12 |
| MIC-84414 | 13.41 | 14.69 | 14.05 |
| MIC-19994 | 30.83 | 18.14 | 24.49 |
| MIC-99023 | 17.85 | 12.10 | 17.85 |

Example 10

Strains and Culture Preparations for Greenhouse Experiment 1

To prepare the culture as initial inocula for various assays, MIC-82330 was grown in one liter of 50% Trypticase soy (TS) broth in a 2.5-liter Ultra Yield flasks (Thomson Instrument Company). The culture was grown at 25° C. with continuous shaking at a speed of 130 revolutions per minute (rpm) for five days. The cultures were aliquoted into 50-mL Falcon tubes and were harvested by centrifugation at a speed of 3,500 rpm for 20 minutes. Spent broth was decanted from tubes, cells were resuspended in 40 mM sodium phosphate buffer pH 7. The bacterium titer was quantified using standard dilution plating and subsequently diluted as appropriate in 40 mM phosphate buffer to allow for desired target per seed application rates.

Fungi

Spore solutions are made by rinsing and scraping spores from agar slants on which MIC-19994 had been growing for about 1 month. Rinsing is done with 0.05% Silwet. Solutions are passed through Miracloth to filter out mycelia. Spores per ml are counted under microscope using a hemocytometer. The stock suspension is then diluted into $10^6$ spores/ml utilizing water. 3 μl of spore suspension is used per seed (~$10^3$ CFUs/seed is obtained). Control treatments are prepared by adding equivalent volumes of sterile water to seeds.

Example 11

Formulation of Endophyte Seed Treatments for Greenhouse Experiment 2

Endophyte compositions were generated comprising an oil high in erucic acid, a non-ionic surfactant, and a plantability polymer.

TABLE 14

Components of endophyte compositions to treat 50 grams of seed

| Formulation | Oil | Oil volume (mL) | 0.5% Triton X-100 volume (mL) | Flo-Rite ® (mL) |
| --- | --- | --- | --- | --- |
| A_2 | Rapeseed | 0.2545 | 0.12727 | 0.049 |
| B_2 | Rapeseed | 0.1273 | 0.2545 | 0.049 |
| C_2 | None | 0 | 0.38182 | 0.049 |
| A_1 | Rapeseed | 0.1273 | 0.2545 | 0.049 |
| A_4 | None | 0 | 0 | 0.049 |

Example 12

Inoculation of Rice Seeds with Endophytes for Greenhouse Trial 1

Endophyte treatments were heterologously disposed to rice seeds according to one of two different formulation protocols (Formulation Protocol A, Formulation Protocol B). A corresponding seed formulation control, lacking any endophyte, was also prepared included for each type of formulation. Further seeds lacking any formulation and endophyte were planted as a non-treated baseline control. Formulation A included only diluent (0.05% silwet for MIC-19994, 40 mM phosphate buffer for MIC-82330) and microbial preparations. Formulation B included the same diluents listed above and the seed plantability polymer Flo Rite® 1706 applied at 2.0 oz/cwt seed per the manufacturer. Microbe and polymer were applied sequentially.

For endophytes formulated by Formulation Protocol A, microbial preparations were applied to the seeds at a rate of 1 μL/seed and the seeds were agitated for at least 20 seconds to disperse the microbe.

For endophytes formulated by Formulation Protocol B, microbial preparations were applied to the seeds at a rate of 1 μL/seed. Then Flo Rite® 1706 plantability polymer was applied to seeds per the manufacturer's suggestion (2.0 oz/cwt of seed) and agitated for 20 seconds to disperse the polymer.

Treated seeds were planted within 2-3 hours of treatment.

Example 13

Cultivation and of Endophyte-Treated Plants in Greenhouse Experiment 2

A sandy loam growth substrate was mixed in the greenhouse and consisting of 60% loam and 40% mortar sand (Northeast Nursery, Peabody, Mass.). Prior to mixing, loam was sifted through a ⅜" square steel mesh screen to remove larger particles and debris. Rice seeds were treated with commercial fungicidal and insecticidal treatment Apron XL® (Syngenta, Basel, Switzerland) according to the manufacturer's instructions. Seeds were heterologously disposed with the endophyte formulations and formulation control (lacking any endophyte) as described in Example 11, untreated seeds (lacking formulation and endophyte) were also planted. Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate.

The experimental design called for a completely randomized pattern of each treatment within each block/replicate. Environmental conditions were set at 12 h photoperiod, at 22/18 C temperature for day/night period and light intensity was set at 650 μMol m$^{-2}$ s$^{-1}$. Post-planting, the seeds were watered to maintain approximately 80% soil capacity. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded.

TABLE 17

Dry root biomass of endophyte and formulation treated rice plants

| Rice - root biomass | Formulation | Dose | Average dry root biomass (g) | Overall, % change over untreated |
|---|---|---|---|---|
| Controls | Untreated | | 0.045 | 0 |
| | A_1 | | 0.062 | 37.36 |
| | B_1 | | 0.042 | -8.24 |
| | C_1 | | 0.067 | 47.8 |
| | A_3 | | 0.058 | 26.92 |
| | B_3 | | 0.05 | 10.44 |
| | C_3 | | 0.045 | -0.55 |
| MIC-19994 | A_1 | low | 0.058 | 26.74 |
| | | medium | 0.056 | 23.63 |
| | | high | 0.073 | 61.17 |
| MIC-82330 | A_3 | low | 0.059 | 29.67 |
| | | medium | 0.066 | 44.51 |
| | | high | 0.049 | 7.14 |

TABLE 18

Dry shoot biomass of endophyte and formulation treated rice plants

| Rice - shoot biomass | Formulation | Dose | Average dry shoot biomass (g) | Overall % change over untreated |
|---|---|---|---|---|
| Controls | Untreated | | 0.132 | 0 |
| | A_1 | | 0.131 | -0.54 |
| | B_1 | | 0.123 | -7.21 |
| | C_1 | | 0.135 | 2.02 |
| | A_3 | | 0.12 | -8.9 |
| | B_3 | | 0.122 | -7.55 |
| | C_3 | | 0.116 | -12.12 |
| MIC-19994 | A_1 | low | 0.125 | -5.45 |
| | | medium | 0.108 | -18.27 |
| | | high | 0.127 | -4.18 |
| MIC-82330 | A_3 | low | 0.134 | 1.14 |
| | | medium | 0.127 | -4.08 |
| | | high | 0.133 | 0.52 |

TABLE 19

Dry shoot biomass of endophyte and formulation treated rice plants

| Treatment | Average dry shoot biomass (g) | Standard deviation | Standard error of the mean | % change over relevant formulation control | % change over untreated control |
|---|---|---|---|---|---|
| Untreated control | 0.132 | 0.0304 | 0.00717 | 0 | 0.00% |
| Formulation control A_1 | 0.131 | 0.029 | 0.00683 | 0 | -0.76% |
| Formulation control A_3 | 0.12 | 0.0308 | 0.00726 | 0 | -9.09% |

TABLE 19-continued

Dry shoot biomass of endophyte and formulation treated rice plants

| Treatment | Average dry shoot biomass (g) | Standard deviation | Standard error of the mean | % change over relevant formulation control | % change over untreated control |
|---|---|---|---|---|---|
| Formulation control B_1 | 0.123 | 0.0445 | 0.01049 | 0 | −6.82% |
| Formulation control B_3 | 0.122 | 0.0326 | 0.0077 | 0 | −7.58% |
| Formulation control C_1 | 0.135 | 0.0348 | 0.0082 | 0 | 2.27% |
| Formulation control C_3 | 0.116 | 0.0328 | 0.00773 | 0 | −12.12% |
| MIC-19994 A_1 high | 0.127 | 0.0367 | 0.0089 | −3.66 | −3.79% |
| MIC-19994 A_1 low | 0.125 | 0.0307 | 0.00723 | −4.93 | −5.30% |
| MIC-19994 A_1 medium | 0.108 | 0.032 | 0.00753 | −17.82 | −18.18% |
| MIC-82330 A_3 high | 0.133 | 0.042 | 0.00991 | 10.34 | 0.76% |
| MIC-82330 A_3 low | 0.134 | 0.0372 | 0.00903 | 11.02 | 1.52% |
| MIC-82330 A_3 medium | 0.127 | 0.0299 | 0.00704 | 5.29 | −3.79% |

Example 14

Method of Preparing Biomass for Field Trials

Preparation of Bacterial Endophytes

An agar plug of each bacterial strain was transferred using a transfer tube to 4 mL of potato dextrose broth (PDB) in a 24 well plate and incubated at room temperature at 675 rpm on a shaker for 3 days. After growth of bacteria in broth, 200 µl was transferred into a spectrophotometer reading plate and bacteria OD was read at 600 nm absorbance. All bacteria strains were then normalized to 0.05 OD utilizing PBS 1x buffer. Once desired dilutions were made, 3 µl of the bacteria solution was applied per seed, and mixed well by shaking in a sterile Falcon tube for 5-10 seconds.

Preparation of Fungal Endophytes

Preparation of molasses broth and potato dextrose agar: Molasses broth was prepared by dissolving 30 g molasses and 5 g yeast extract per liter deionized water in an autoclavable container and autoclaving (15 psi, 121° C.) for 45 min. Potato dextrose agar (PDA) plates were prepared by dissolving 39.0 g PDA powder per liter deionized water in an autoclavable container and autoclaving (15 psi, 121° C.) for 45 min. The agar was allowed to cool to 50-60° C., before pouring into sterile petri plates (30 mL per 90 mm plate).

Liquid biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. Then the culture was placed in a blender for 5 seconds and 1 mL of the blended was centrifuged and the supernatant was discarded and the pellet resuspended in 0.5 mL 1× Phosphate Buffered Saline (PBS) to generate inoculum.

Dry biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. In sterile conditions, the liquid culture was carefully decanted using 150 mm sterile filter paper on a sterilized Buchner funnel over a sterile flask. Once all liquid had passed through the funnel, the pellet was rinsed with sterile water until the filtrate ran clear. When dry, the pellet was transferred to a drying cabinet and dried until brittle. The pellet was then ground into a fine powder, and sample used to generate CFU counts.

Preparation of Sodium Alginate and Talc for Seed Treatments

A 2% weight/volume solution of sodium alginate for the seed coatings is prepared by the following method. An Erlenmeyer flask is filled with the appropriate volume of deionized water and warmed to 50 degrees Celsius on a heat plate with agitation using a stir bar. The appropriate mass of sodium alginate powder for the desired final concentration solution is slowly added until dissolved. The solution is autoclaved at 121 degrees Celsius at 15 PSI for 30 minutes to sterilize.

Talcum powder for the powdered seed coatings is prepared by the following method. Talcum powder is aliquoted into Ziploc bags or 50 mL Falcon tubes, and autoclaved in dry cycle (121 degrees Celsius at 15 PSI for 30 minutes) to sterilize.

Heterologous Disposition of Endophytes on Wheat Seeds

Wheat seeds were treated with commercial fungicidal and insecticidal treatments. Seeds were heterologously disposed to each endophyte according to the following seed treatment protocols for liquid or dry formulation.

Liquid formulation: The 2% sodium alginate solution prepared above was added to the seeds at a rate of 15 ml per kg of seeds. Liquid fungal culture as prepared in above was added to the seeds at a rate of 8.3 ml per kg of seeds. Control treatments were prepared using equivalent volumes of sterile broth. The seeds were then agitated to disperse the solution evenly on the seeds.

Then 12.5 g of talc powder per kg of seed was added and the seeds were agitated to disperse the powder evenly on the seeds. Then 17 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Dry formulation: The 2% sodium alginate solution prepared above was added to the seeds at a rate of 20 ml per kg of seeds. Equal parts of the fungal dry biomass prepared above and the talc prepared above were mixed. The solution is applied to the prepared seeds so that an equivalent of 12.5 g of fungal dry biomass was applied per kg of seeds. Control treatments were prepared using equivalent volumes of talc. The seeds were then agitated to disperse the solution evenly on the seeds.

Then 17 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Soy Seeds

Soybean seeds of three varieties of soy seeds were treated with commercial fungicidal and insecticidal treatment CruiserMaxx® (Syngenta, Basel, Switzerland) per the manufacturer's instructions. Seeds were heterologously disposed to each endophyte according to the following seed treatment protocols for liquid or dry formulation.

Liquid formulation: The 2% sodium alginate solution prepared above was added to the seeds at a rate of 8.3 ml per kg of seeds. Liquid fungal culture as prepared above was added to the seeds at a rate of 8.3 (fungal endophytes) or 8.4 (bacterial endophytes) ml per kg of seeds. Control treatments were prepared using equivalent volumes of sterile broth. The seeds were then agitated to disperse the solution evenly on the seeds. For fungal endophytes, 15 g per kg of seed of the talc powder prepared above was added and the seeds were agitated to disperse the powder evenly on the seeds. Then 13.3 (for fungal endophyte treatments) or 2.7 (for bacterial endophyte treatments) ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Dry fungal formulation: The 2% sodium alginate was added to the seeds at a rate of 16.6 ml per kg of seeds. Equal parts of the dry fungal biomass prepared above and the talc prepared in above were mixed. The solution was applied so that an equivalent of 10 g of dry fungal biomass was applied per kg of seeds. Control treatments were prepared using equivalent volumes of talc. The seeds were then agitated to disperse the solution evenly on the seeds.

Then 13.3 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Corn Seeds

Corn seeds were treated with commercial fungicidal and insecticidal treatment. Seeds were heterologously disposed to each endophyte according to the following seed treatment protocols for liquid or dry formulation.

Dry fungal formulation: The 2% sodium alginate solution prepared above was added to the seeds at a rate of 23 ml per kg of seeds. Equal parts of the dry fungal biomass prepared in above and the talc prepared above were mixed. The solution was applied so that an equivalent of 10 g of fungal powder was applied per kg of seeds. Control treatments were prepared using equivalent volumes of talc. The seeds were then agitated to disperse the solution evenly on the seeds.

Then 16.6 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Liquid formulation: Liquid culture as prepared above was added to the seeds at a rate of 23 (for fungal endophyte treatments) or 8.4 (for bacterial endophyte treatments) ml per kg of seeds, with equivalent volumes of the prepared sodium alginate. Control treatments were prepared using equivalent volumes of sterile broth. The seeds were then agitated to disperse the solution evenly on the seeds. For fungal endophytes, 15 g per kg of seed of the talc powder prepared in sterile was added and the seeds were agitated to disperse the powder evenly on the seeds. Then 16.6 ml (for fungal endophyte treatments) or 2.4 ml (for bacterial endophyte treatments) per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Example 15

Cultivation of Endophyte-treated Plants in Field Experiment 1

Field trials were conducted in 6 different locations across the Midwest region of the United States in 2016, under non-irrigated (dryland) conditions. Four varieties of spring wheat seeds were treated with commercial fungicidal and insecticidal treatment. Seeds were heterologously disposed with the endophyte formulations and formulation control (lacking any endophyte) as described in Example 14, untreated seeds (lacking formulation and endophyte) were also planted. Two varieties were planted at each location. Seeds were sown in regularly spaced rows in soil at 1.2 million seeds/acre seeding density. At each location 4 replicate plots were planted per endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

TABLE 20

Average yield of endophyte treated spring wheat and untreated and formulation controls by location, Field Experiment 1

|  | Loc 1, yield (bu/ac) | Loc 2, yield (bu/ac) | Loc 3, yield (bu/ac) | Loc 4, yield (bu/ac) | Loc 5, yield (bu/ac) | Loc 6, yield (bu/ac) | Overall yield (bu/ac) | Overall % Δ untreated control | Overall % Δ formulation control |
|---|---|---|---|---|---|---|---|---|---|
| Untreated control | 40.48 | 35.45 | 34.21 | 25.20 | 87.73 | 39.91 | 43.83 |  | 0.5 |
| Formulation control | 40.58 | 35.34 | 34.57 | 24.89 | 87.46 | 38.74 | 43.60 | −0.5 |  |
| MIC-15870 | 41.14 | 35.78 | 35.22 | 25.11 | 88.34 | 42.91 | 44.75 | 2.1 | 2.6 |
| MIC-84414 | 40.98 | 35.83 | 34.48 | 22.03 | 89.05 | 39.82 | 43.70 | −0.3 | 0.2 |
| MIC-99023 | 40.11 | 36.25 | 33.83 | 23.81 | 87.26 | 39.02 | 43.38 | −1.0 | −0.5 |

TABLE 21

Average yield of endophyte treated spring wheat and untreated and formulation controls by plant variety, Field Experiment 1

|  | NDSU Barlow Variety 1, yield (bu/acre) | NDSU Prosper Variety 2, yield (bu/acre) | SDSU Focus Variety 3, yield (bu/acre) | SDSU Select Variety 4, yield (bu/acre) | Overall, yield (bu/acre) | Overall % Δ untreated control | Overall % Δ formulation control |
|---|---|---|---|---|---|---|---|
| Untreated control | 50.87 | 57.03 | 33.5 | 33.92 | 43.83 |  | 0.5 |
| Formulation control | 51.65 | 55.53 | 33.63 | 33.58 | 43.6 | −0.5 |  |
| MIC-15870 | 53.79 | 57.18 | 32.68 | 35.34 | 44.75 | 2.1 | 2.6 |
| MIC-84414 | 51.57 | 57.33 | 33.33 | 32.55 | 43.7 | −0.3 | 0.2 |
| MIC-99023 | 49.69 | 57.05 | 34.31 | 32.48 | 43.38 | −1 | −0.5 |

Example 16

Cultivation of Endophyte-treated Plants in Field Experiment 2

Field trials were conducted in 2016, under non-irrigated (dryland) conditions. Two varieties of spring wheat seeds were treated with commercial fungicidal and insecticidal treatment. Seeds were heterologously disposed with the endophyte formulations and formulation control (lacking any endophyte) as described in Example 14, untreated seeds (lacking formulation and endophyte) were also planted. Seeds were sown in regularly spaced rows in soil at 1.2 million seeds/acre seeding density. At each location replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield and grain percent moisture were calculated by the on-board computer.

TABLE 27

Yield of endophyte treated spring wheat and untreated and formulation controls by location, field experiment 2

|  | NDSU Barlow, Variety 1, yield (bu/acre) | NDSU Prosper, Variety 2, yield (bu/acre) | Overall, yield (bu/acre) | Overall % Δ untreated control | Overall % Δ formulation control |
|---|---|---|---|---|---|
| Untreated control | 24.832 | 26.631 | 25.73 |  | −13.3 |
| Formulation control | 31.172 | 28.217 | 29.69 | 15.4 |  |
| MIC-19994 | 31.172 | 26.892 | 29.03 | 12.8 | −2.2 |

Example 17

Cultivation of Endophyte-treated Plants in Field Experiment 3

Field trials were conducted in 2016, under non-irrigated (dryland) conditions. Four varieties of wheat seeds were treated with commercial fungicidal and insecticidal treatment. Seeds were heterologously disposed with the endophyte formulations and formulation control (lacking any endophyte) as described in Example 14, untreated seeds (lacking formulation and endophyte) were also planted. Seeds were sown in regularly spaced rows in soil at 1.2 million seeds/acre seeding density. At each location replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

TABLE 28

Yield of endophyte treated wheat and untreated and formulation controls by variety, field experiment 3

|  | NDSU Barlow Variety 1, yield (bu/acre) | NDSU Prosper Variety 2, yield (bu/acre) | SDSU Focus Variety 3, yield (bu/acre) | SDSU Select Variety 4, yield (bu/acre) | Overall, yield (bu/acre) | Overall % Δ untreated control | Overall % Δ formulation control |
|---|---|---|---|---|---|---|---|
| Untreated control | 27.9 | 27.4 | 39.8 | 43.2 | 31.70 |  | -3.4 |
| Formulation control | 31.2 | 28.2 | 39.0 | 44.2 | 32.80 | 3.5 |  |
| MIC-19994 | 31.2 | 26.9 | 40.4 | 43.9 | 32.83 | 3.6 | 0.1 |

Example 18

Cultivation of Endophyte-Treated Plants in Field Experiment 4

Field trials were conducted in 2016, under non-irrigated (dryland) conditions. Wheat seeds were heterologously disposed with the endophyte formulations and formulation control (lacking any endophyte) as described in Example 14, untreated seeds (lacking formulation and endophyte) were also planted. Seeds were sown in regularly spaced rows in soil at 1.2 million seeds/acre seeding density. At each location replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

Corn

Field trials were conducted in 5 diverse locations in the Southern, Western and Midwestern regions of the United States in 2016. Plots were non-irrigated (dryland) or maintained with suboptimal irrigation at a rate to target approximately 25% reduction in yield. Seeds were prepared with the endophyte formulations and formulation control (lacking any endophyte) as described in Example 14. Seeds were sown in regularly spaced rows in soil at planting densities typical for each region. At each location 3 replicate plots were planted per endophyte or control treatment in a ran-

TABLE 29

Yield of endophyte treated wheat and untreated and formulation controls by location, field experiment 4

|  | Location 2, yield (bu/acre) | Location 3, yield (bu/acre) | Location 4, yield (bu/acre) | Location 5, yield (bu/acre) | Location 6, yield (bu/acre) | Location 7, yield (bu/acre) | Location 8, yield (bu/acre) | Location 9, yield (bu/acre) | Overall, yield bu/ac | Overall % Δ untreated contl | Overall % Δ formulation contl |
|---|---|---|---|---|---|---|---|---|---|---|---|
| Untreated control | 35.4 | 34.2 | 25.2 | 87.7 | 39.9 | 41 | 40.5 | 29.2 | 41.6 |  | -1.2 |
| Formulation control | 35.3 | 34.6 | 24.9 | 87.5 | 38.7 | 43.6 | 40.6 | 32 | 42.2 | 1.2 |  |
| MIC-15870 | 35.8 | 35.2 | 25.1 | 88.3 | 42.9 | 43.5 | 41.1 | 34.1 | 43.3 | 3.9 | 2.6 |
| MIC-84414 | 35.8 | 34.5 | 22 | 89.1 | 39.8 | 41.8 | 41 | 40 | 43.1 | 3.3 | 2.0 |
| MIC-99023 | 36.3 | 33.8 | 23.8 | 87.3 | 39 | 42.3 | 40.1 | 37 | 42.4 | 2.0 | 0.7 |

Example 19

Assessment of Improved Plant Characteristics: Field Conditions

Wheat

Field trials were conducted in 2016, under non-irrigated (dryland) conditions. Wheat seeds were treated with commercial fungicidal and insecticidal treatment. Seeds were heterologously disposed with the endophyte formulations and formulation control (lacking any endophyte) as described in Example 14, untreated seeds (lacking formulation and endophyte) were also planted. Seeds were sown in regularly spaced rows in soil at 1.2 million seeds/acre seeding density. At each location at least 3 replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

domized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to present border effects.

Soy

Field trials were conducted in 4 different locations across the Midwest region of the United States in 2016, under non-irrigated (dryland) conditions. Seeds were prepared with the endophyte formulations and formulation control (lacking any endophyte) as described in Example 14. Seeds were sown in regularly spaced rows in soil at 180,000 seeds/acre seeding density. At each location 4 replicate plots were planted per endophyte or control treatment in a randomized complete block design). Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

TABLE 30

Median yield increase endophyte treatments in field trials in multiple crops.

|  | Wheat (Bu/acre) | Corn (Bu/acre) | Soy (Bu/acre) |
| --- | --- | --- | --- |
| MIC-15870 | 1.1 | 3.9 |  |
| MIC-84414 | 0.1 | 3.6 | 0.34 |
| MIC-68000 | 0.5 |  |  |

Example 20

Method of Determining Seed Nutritional Quality Trait Component: Fat

Seed samples from harvested plants are obtained as described in Example 19. Analysis of fat is conducted on replicate samples according to the Association of Official Agricultural Chemists Reference Method AOAC 920.39, of the Official Methods Of Analysis of AOAC International, $20^{th}$ Edition (2016), herein incorporated by reference in its entirety. Samples are weighed onto filter paper, dried, and extracted in hot hexane for 4 hrs using a Soxlhet system. Oil is recovered in pre-weighed glassware, and % fat was measured gravimetrically. Mean percent changes between the treatment (endophyte-treated seed) and control (seed treated with the formulation but no endophyte) are calculated.

Example 21

Method of Determining Seed Nutritional Quality Trait Component: Ash

Seed samples from harvested plants are obtained as described in Example 19. Analysis of fat is conducted on replicate samples according to the Association of Official Agricultural Chemists Reference Method AOAC 920.39, of the Official Methods Of Analysis of AOAC International, $20^{th}$ Edition (2016). Samples are weighed into pre-weighed crucibles, and ashed in a furnace at 600° C. for 3 hr. Weight loss on ashing is calculated as % ash. Mean percent changes between the treatment (endophyte-treated seed) and control (seed treated with the formulation but no endophyte) are calculated.

Example 22

Method of Determining Seed Nutritional Quality Trait Component: Fiber

Seed samples from harvested plants are obtained as described in Example 19. Analysis of fat is conducted on replicate samples according to the Association of Official Agricultural Chemists Reference Method AOAC 920.39, of the Official Methods Of Analysis of AOAC International, $20^{th}$ Edition (2016). Samples are weighed into filter paper, defatted and dried, and hydrolyzed first in acid, then in alkali solution. The recovered portion is dried, weighed, ashed at 600°, and weighed again. The loss on ashing is calculated as % Fiber. Mean percent changes between the treatment (endophyte-treated seed) and control (seed treated with the formulation but no endophyte) are calculated.

Example 23

Method of Determining Seed Nutritional Quality Trait Component: Moisture

Seed samples from harvested plants are obtained as described in Example 19. Analysis of fat is conducted on replicate samples according to the Association of Official Agricultural Chemists Reference Method AOAC 920.39, of the Official Methods Of Analysis of AOAC International, $20^{th}$ Edition (2016). Samples are weighed into pre-weighed aluminum dishes, and dried at 135° C. for 2 hrs. Weight loss on drying is calculated as % Moisture. Mean percent changes between the treatment (endophyte-treated seed) and control (seed treated with the formulation but no endophyte) are calculated.

Example 24

Method of Determining Seed Nutritional Quality Trait Component: Protein

Seed samples from harvested plants are obtained as described in Example 19. Analysis of fat is conducted on replicate samples according to the Association of Official Agricultural Chemists Reference Method AOAC 920.39, of the Official Methods Of Analysis of AOAC International, $20^{th}$ Edition (2016). Samples are combusted and nitrogen gas is measured using a combustion nitrogen analyzer (Dumas). Nitrogen is multiplied by 6.25 to calculate % protein. Mean percent changes between the treatment (endophyte-treated seed) and control (seed treated with the formulation but no endophyte) are calculated.

Example 25

Method of Determining Seed Nutritional Quality Trait Component: Carbohydrate

Seed samples from harvested plants are obtained as described in Example 19. Analysis of carbohydrate is determined for replicate samples as a calculation according to the following formula:

$$\text{Total Carbohydrate} = 100\% - \%(\text{Protein} + \text{Ash} + \text{Fat} + \text{Moisture} + \text{Fiber})$$

Where % Protein is determined according to the method of Example 24, % Ash is determined according to the method of Example 21, % Fat is determined according to the method of Example 20, % Moisture is determined according to the method of Example 23, and % Fiber is determined according to the method of Example 22. Mean percent changes between the treatment (endophyte-treated seed) and control (seed treated with the formulation but no endophyte) are calculated.

Example 26

Method of Determining Seed Nutritional Quality Trait Component: Calories

Seed samples from harvested plants are obtained as described in Example 19. Analysis of Calories is determined for replicate samples as a calculation according to the following formula:

Total Calories=(Calories from protein)+(Calories from carbohydrate)+Calories from fat)

Where Calories from protein are calculated as 4 Calories per gram of protein (as determined according to the method of Example 24), Calories from carbohydrate are calculated as 4 Calories per gram of carbohydrate (as determined according to the method of Example 25), and Calories from fat are calculated as 9 Calories per gram of fat (as determined according to the method of Example 20). Mean percent changes between the treatment (endophyte-treated seed) and control (seed treated with the formulation but no endophyte) are calculated.

Example 27

Additional Methods for Creating Synthetic Compositions

Osmopriming and Hydropriming

A fungal or bacterial endophyte is inoculated onto seeds during the osmopriming (soaking in polyethylene glycol solution to create a range of osmotic potentials) and/or hydropriming (soaking in de-chlorinated water) process. Osmoprimed seeds are soaked in a polyethylene glycol solution containing a bacterial and/or fungal endophyte for one to eight days and then air dried for one to two days. Hydroprimed seeds are soaked in water for one to eight days containing a bacterial and/or fungal endophyte and maintained under constant aeration to maintain a suitable dissolved oxygen content of the suspension until removal and air drying for one to two days. Talc and or flowability polymer are added during the drying process.

Foliar Application

A fungal or bacterial endophyte is inoculated onto aboveground plant tissue (leaves and stems) as a liquid suspension in dechlorinated water containing adjuvants, sticker-spreaders and UV protectants. The suspension is sprayed onto crops with a boom or other appropriate sprayer.

Soil Inoculation

A fungal or bacterial endophyte is inoculated onto soils in the form of a liquid suspension either; pre-planting as a soil drench, during planting as an in furrow application, or during crop growth as a side-dress. A fungal or bacterial endophyte is mixed directly into a fertigation system via drip tape, center pivot or other appropriate irrigation system.

Hydroponic and Aeroponic Inoculation

A fungal or bacterial endophyte is inoculated into a hydroponic or aeroponic system either as a powder or liquid suspension applied directly to the rockwool substrate, or applied to the circulating or sprayed nutrient solution.

Vector-mediated Inoculation

A fungal or bacterial endophyte is introduced in power form in a mixture containing talc or other bulking agent to the entrance of a beehive (in the case of bee-mediation) or near the nest of another pollinator (in the case of other insects or birds. The pollinators pick up the powder when exiting the hive and deposit the inoculum directly to the crop's flowers during the pollination process.

Root Wash

The method includes contacting the exterior surface of a plant's roots with a liquid inoculant formulation containing a purified bacterial population, a purified fungal population, or a mixture of purified bacteria and fungi. The plant's roots are briefly passed through standing liquid microbial formulation or liquid formulation is liberally sprayed over the roots, resulting in both physical removal of soil and microbial debris from the plant roots, as well as inoculation with microbes in the formulation.

Seedling Soak

The method includes contacting the exterior surfaces of a seedling with a liquid inoculant formulation containing a purified bacterial population, a purified fungal population, or a mixture of purified bacteria and fungi. The entire seedling is immersed in standing liquid microbial formulation for at least 30 seconds, resulting in both physical removal of soil and microbial debris from the plant roots, as well as inoculation of all plant surfaces with microbes in the formulation. Alternatively, the seedling can be germinated from seed in or transplanted into media soaked with the microbe(s) of interest and then allowed to grow in the media, resulting in soaking of the plantlet in microbial formulation for much greater time totaling as much as days or weeks. Endophytic microbes likely need time to colonize and enter the plant, as they explore the plant surface for cracks or wounds to enter, so the longer the soak, the more likely the microbes will successfully be installed in the plant.

Wound Inoculation

The method includes contacting the wounded surface of a plant with a liquid or solid inoculant formulation containing a purified bacterial population, a purified fungal population, or a mixture of purified bacteria and fungi. Plant surfaces are designed to block entry of microbes into the endosphere, since pathogens attempting to infect plants in this way. In order to introduce beneficial endophytic microbes to plant endospheres, we need a way to access the interior of the plant which we can do by opening a passage by wounding. This wound can take a number of forms, including pruned roots, pruned branches, puncture wounds in the stem breaching the bark and cortex, puncture wounds in the tap root, puncture wounds in leaves, and puncture wounds seed allowing entry past the seed coat. Wounds can be made using needles, hammer and nails, knives, drills, etc. Into the wound can then be contacted the microbial inoculant as liquid, as powder, inside gelatin capsules, in a pressurized capsule injection system, in a pressurized reservoir and tubing injection system, allowing entry and colonization by microbes into the endosphere. Alternatively, the entire wounded plant can be soaked or washed in the microbial inoculant for at least 30 seconds, giving more microbes a chance to enter the wound, as well as inoculating other plant surfaces with microbes in the formulation—for example pruning seedling roots and soaking them in inoculant before transplanting is a very effective way to introduce endophytes into the plant.

Injection

The method includes injecting microbes into a plant in order to successfully install them in the endosphere. Plant surfaces are designed to block entry of microbes into the endosphere, since pathogens attempting to infect plants in this way. In order to introduce beneficial endophytic microbes to endospheres, we need a way to access the interior of the plant which we can do by puncturing the plant surface with a need and injecting microbes into the inside of the plant. Different parts of the plant can be inoculated this way including the main stem or trunk, branches, tap roots, seminal roots, buttress roots, and even leaves. The injection can be made with a hypodermic needle, a drilled hole injector, or a specialized injection system, and through the puncture wound can then be contacted the microbial inoculant as liquid, as powder, inside gelatin capsules, in a pressurized capsule injection system, in a pressurized reservoir and tubing injection system, allowing entry and colonization by microbes into the endosphere.

Example 28

Identification of Sequence Variants Across Core Genes

Phylogenomic analysis of whole genome sequences of endophytes can be used to identify distinguishing sequence variants. Sets of genes suitable for phylogenomic analysis as well as methods for identifying the same are well known in the art, for example Floutas et al. (2012) The Paleozoic origin of enzymatic lignin decomposition reconstructed from 31 fungal genomes. Science, 336(6089):1715-9. doi: 10.1126/science.1221748 and James T Y, Pelin A, Bonen L, Ahrendt S, Sain D, Corradi N, Stajich J E. Shared signatures of parasitism and phylogenomics unite Cryptomycota and microsporidia. Curr Biol. 2013; 23(16):1548-53. doi: 10.1016/j.cub.2013.06.057. Orthologous genes to the reference set are identified in protein data bases derived from the genome of each species. Orthologous genes can be identified in the genomes using methods well known including reciprocal best hits (Ward N, Moreno-Hagelsieb G. Quickly Finding Orthologs as Reciprocal Best Hits with BLAT, LAST, and UBLAST: How Much Do We Miss? de Crecy-Lagard V, ed. *PLoS ONE*. 2014; 9(7):e101850. doi:10.1371/journal.pone.0101850) and Hidden Markov Models (HMMs). The best hits are extracted and a multiple sequence alignment generated for each set of orthologous genes. The alignments are used to build phylogenetic trees using methods well known in the art including Bayesian inference and maximum likelihood methods, for example using software tools MrBayes (Huelsenbeck, J. P. & Ronquist (2001) MRBAYES: Bayesian inference of phylogenetic trees. Bioinformatics, 17(8):754-755) and RAxML (Stamatakis, A. (2014) RAxML version 8: a tool for phylogenetic analysis and post-analysis of large phylogenies. *Bioinformatics*, 30 (9): 1312-1313. doi: 10.1093/bioinformatics/btu033). Sequence variants which distinguish between closely related species are identified.

Example 29

Identification of Unique Genes in an Endophyte of Interest

Whole genome analysis of endophytes can be used to identify genes whose presence, absence or over or under representation ("differential abundance") are associated with desirable phenotypes. To identify genes with differential abundance in the genome of an endophyte of interest, protein sequences predicted from the genomes of the endophyte and closely related species compared in an all-vs-all pairwise comparison (for example, using BLAST) followed by clustering of the protein sequences based on alignment scores (for example, using MCL: Enright A. J., Van Dongen S., Ouzounis C. A. An efficient algorithm for large-scale detection of protein families. Nucleic Acids Research 30(7): 1575-1584 (2002)). Additional software tools useful for this analysis are well known in the art and include OMA, OrthoMCL and TribeMCL (Roth A C, Gonnet G H, Dessimoz C. Algorithm of OMA for large-scale orthology inference. BMC Bioinformatics. 2008; 9:518. doi: 10.1186/1471-2105-9-518, Enright A J, Kunin V, Ouzounis C A. Protein families and TRIBES in genome sequence space. Nucleic Acids Res. 2003; 31(15):4632-8.; Chen F, Mackey A J, Vermunt J K, Roos D S. Assessing performance of orthology detection strategies applied to eukaryotic genomes. PLoS One. 2007; 2(4):e383.). The protein clusters are queried to identify clusters with differential abundance of proteins derived from endophytes having desirable phenotypes. Proteins of these clusters define the unique properties of these endophytes, and the abundance of genes encoding these proteins may be used to identify endophytes of the present invention.

Having illustrated and described the principles of the present invention, it should be apparent to persons skilled in the art that the invention can be modified in arrangement and detail without departing from such principles. It is to be understood that while the invention has been described in conjunction with the detailed description thereof, the foregoing description is intended to illustrate and not limit the scope of the invention, which is defined by the scope of the appended claims. Other embodiments, advantages, and modifications are within the scope of the following claims.

I claim:

1. A synthetic composition comprising a plant element and an endophyte, wherein the endophyte is heterologously disposed to the plant element, wherein the endophyte is a member of the genus *Periconia* and comprises at least one polynucleotide sequence at least 97% identical to a sequence selected from the group consisting of SEQ ID NO: 32 and 33, wherein the region of alignment is at least 85% of the length of the query sequence, and wherein said synthetic composition is capable of providing an improved trait of agronomic importance as compared to a reference plant element not further comprising the endophyte.

2. The synthetic composition of claim 1, wherein the plant element is of the genus *Triticum* and the improved trait of agronomic importance is selected from the group consisting of germination rate, dry shoot biomass, and yield.

3. The synthetic composition of claim 1, wherein the plant element is of the genus *Glycine* and the improved trait of agronomic importance is selected from the group consisting of root length and root area.

4. The synthetic composition of claim 1, wherein the plant element is of the genus *Zea* and the improved trait of agronomic importance is yield.

5. The synthetic composition of claim 1, wherein the plant element is a seed.

6. The synthetic composition of claim 5, wherein the seed is modified.

7. The synthetic composition of claim 1, further comprising a formulation that comprises one or more of the following: a stabilizer, a preservative, a carrier, a surfactant, an anticomplex agent, a fungicide, a nematicide, a bactericide, an insecticide, a herbicide, or any combination thereof.

8. The synthetic composition of claim 1, wherein the synthetic composition is shelf-stable.

9. The synthetic composition of claim 1, wherein the endophyte is a member of the genus *Periconia* as deposited under NRRL Culture Deposit No. 67466.

10. The synthetic composition of claim 1, wherein the endophyte is a modified endophyte of the genus *Periconia* obtained from the endophyte as deposited under NRRL Culture Deposit No. 67466.

11. The synthetic composition of claim 1, wherein the at least one polynucleotide sequence is 100% identical to SEQ ID NO: 32.

12. The synthetic composition of claim 1, wherein the at least one polynucleotide sequence is 100% identical to SEQ ID NO: 33.

13. The synthetic composition of claim 1, comprising a polynucleotide sequence that is at least 97% identical to SEQ ID NO: 32 and a polynucleotide sequence that is at least 97% identical to SEQ ID NO: 33.

14. The synthetic composition of claim 1, comprising a polynucleotide sequence that is 100% identical to SEQ ID NO: 32 and a polynucleotide sequence that is 100% identical to SEQ ID NO: 33.

15. The synthetic composition of claim 1, comprising a polynucleotide sequence that is at least 97% identical to SEQ ID NO: 33.

* * * * *

SEQUENCE LISTING

```
<160> NUMBER OF SEQ ID NOS: 51

<210> SEQ ID NO 1
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 1
agagtttgat ymtggctcag                                            20

<210> SEQ ID NO 2
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 2
```
ggttaccttg ttacgactt                                                19

<210> SEQ ID NO 3
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 3
gtgycagcmg ccgcggtaa                                                19

<210> SEQ ID NO 4
<211> LENGTH: 20
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 4
ggactacnvg ggtwtctaat                                               20

<210> SEQ ID NO 5
<211> LENGTH: 22
<212> TYPE: DNA
<213> ORGANISM: Artificial sequence
<220> FEATURE:
<223> OTHER INFORMATION: Synthetic Polynucleotide

<400> SEQUENCE: 5
cttggtcatt tagaggaagt aa                                            22

<210> SEQ ID NO 6
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 6
gctgcgttct tcatcgatgc                                               20

<210> SEQ ID NO 7
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 7
gcatcgatga agaacgcagc                                               20

<210> SEQ ID NO 8
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 8
tcctgaggga aacttcg                                                  17

```
<210> SEQ ID NO 9
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 9
tggtcaacta gcgaacgtgt                                                     20

<210> SEQ ID NO 10
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 10
agaggcgaac gggtacact                                                      19

<210> SEQ ID NO 11
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 11
aaatgttgtt catgcgacca                                                     20

<210> SEQ ID NO 12
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 12
tctcccagga gctttcgtta                                                     20

<210> SEQ ID NO 13
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 13
tgctggtagt gcgaatgaaa                                                     20

<210> SEQ ID NO 14
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 14
ctttcgggtt ccatcaggt                                                      19

<210> SEQ ID NO 15
<211> LENGTH: 19
<212> TYPE: DNA
<213> ORGANISM: Artificial sequence
<220> FEATURE:
<223> OTHER INFORMATION: Synthetic Polynucleotide
```

<400> SEQUENCE: 15
ccagtttcct gtccaccaa    19

<210> SEQ ID NO 16
<211> LENGTH: 22
<212> TYPE: DNA
<213> ORGANISM: Artificial sequence
<220> FEATURE:
<223> OTHER INFORMATION: Synthetic Polynucleotide

<400> SEQUENCE: 16
taggcgttgt tgttgttgtt gt    22

<210> SEQ ID NO 17
<211> LENGTH: 18
<212> TYPE: DNA
<213> ORGANISM: Artificial sequence
<220> FEATURE:
<223> OTHER INFORMATION: Synthetic Polynucleotide

<400> SEQUENCE: 17
acgatctcgg cgggtaat    18

<210> SEQ ID NO 18
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 18
gttcggagcc ctatgttgg    19

<210> SEQ ID NO 19
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 19
cccatrgcyt gyttmcccat dgc    23

<210> SEQ ID NO 20
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 20
gtbcacctyc araccggyca rtg    23

<210> SEQ ID NO 21
<211> LENGTH: 26
<212> TYPE: DNA
<213> ORGANISM: Artificial sequence
<220> FEATURE:
<223> OTHER INFORMATION: Synthetic Polynucleotide

<400> SEQUENCE: 21
ccrgaytgrc craaracraa gttgtc    26

<210> SEQ ID NO 22
<211> LENGTH: 20

```
<212> TYPE: DNA
<213> ORGANISM: Artificial sequence
<220> FEATURE:
<223> OTHER INFORMATION: Synthetic Polynucleotide

<400> SEQUENCE: 22
gaygaymgwg atcayttygg                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 23
cccatwgcyt gcttmcccat                                               20

<210> SEQ ID NO 24
<211> LENGTH: 19
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: n is a, c, g, or t

<400> SEQUENCE: 24
ghgacaagcg tttctcngg                                                19

<210> SEQ ID NO 25
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 25
cttvavytgg aacttgatgg t                                             21

<210> SEQ ID NO 26
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 26
acccgctgaa cttaagc                                                  17

<210> SEQ ID NO 27
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 27
tcctgaggga aacttcg                                                  17

<210> SEQ ID NO 28
<211> LENGTH: 20
<212> TYPE: DNA
<213> ORGANISM: Artificial sequence
<220> FEATURE:
```

<223> OTHER INFORMATION: Synthetic Polynucleotide

<400> SEQUENCE: 28
cttccgtcaa ttcctttaag                                         20

<210> SEQ ID NO 29
<211> LENGTH: 21
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (13)..(13)
<223> OTHER INFORMATION: n is Queuosine

<400> SEQUENCE: 29
tacctggttg atnctgccag t                                       21

<210> SEQ ID NO 30
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 30
tcgcgttcgt taacaaaatg gaccgtat                                28

<210> SEQ ID NO 31
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 31
tcgccagacg gcccagagcc agacccat                                28

<210> SEQ ID NO 32
<211> LENGTH: 1456
<212> TYPE: DNA
<213> ORGANISM: Periconia macrospinosa

<400> SEQUENCE: 32
tcttggtcat ttagaggaag taaaagtcgt aacaaggttt ccgtaggtga acctgcggaa    60
ggatcattac acattcgggg cgcttcggcg ctccttatac acccaccctc tgcctacgtg   120
tacctctata gcttcctcgg cgggctcgcc cgccgccagg aacccacgaa accccttgca   180
ttatacgcga aaacttctga taacaaacct aaattatcac aactttcaac aatggatctc   240
ttggttctgg catcgatgaa gaacgcagcg aaatgcgata agtagtgtga attgcagaat   300
tcagtgaatc atcgaatctt tgaacgcaca ttgcggccat aggtattcct ttggccatgc   360
ctgttcgagc gtcatttaca ccctcaagcc tagcttggtg ttgggcgtct gtcccgccgt   420
tctcgcgcgc ggactcgcct caaagtcatt ggcggcggtc gtgccggccc cctcgcgcag   480
cacatttgcg cttctcggag gccggcgga tccgcgctcc agcaagacct ttcacgactt   540
gacctcggat caggtaggga tacccgctga acttaagcat atcaataagc ggaggaaaag   600
aaaccaacag ggattgccct agtaacggcg agtgaagcgg caacagctca aatttgaaat   660
ctggcccctt ggggtccga gttgtaattt gcagagggtg ctttggcgtt ggcggcggtc   720
taagttcctt ggaacaggac atcgcagagg gtgagaatcc cgtatgtggt cgcatgcctt   780

```
cgccgtgtaa agcccctcg acgagtcgag ttgtttggga atgcagctct aaatgggagg      840
taaatttctt ctaaagctaa ataccggcca gagaccgata gcgcacaagt agagtgatcg     900
aaagatgaaa agcactttgg aaagagagtc aaacagcacg tgaaattgtt gaaagggaag    960
cgcttgcagc cagacttgcc tgtagttgct caccgggct cctgcccggg gcactcttct      1020
gcaggcaggc cagcatcagt ttgggcggtc ggataaaggg ctctgacacg tacttcccct    1080
cggggttgac atacagggga gccgcaatgc gaccagcccg gactgaggtc cgcgcatctg    1140
ctaggatgct ggcgtaatgg ctgtaagcgg cccgtcttga aacacggacc aaggagtcta    1200
acatctatgc gagtgtttgg gtgtcaagcc cgagcgcgca atgaaagtga acggaggtgg    1260
gagcccctcg gggtgcacca tcgaccgatc ctgatgtctt cggatggatt tgagtaagag    1320
catagctgtt gggacccgaa agatggtgaa ctatgcttga ataggtgaa gccagaggaa     1380
actctggtgg aggctcgcag cggttctgac gtgcaaatcg atcgtcaaat ttgggcatag    1440
gggcgaaaga ctaatc                                                    1456
```

<210> SEQ ID NO 33
<211> LENGTH: 599
<212> TYPE: DNA
<213> ORGANISM: Periconia macrospinosa

<400> SEQUENCE: 33

```
tggtcaacta gcgaacgtgt ttggccgcag gtctcctctt atttattgcg ttgcgctttt    60
cgctttgggg agtgggattg ctggaggcgc ccataatcct ggaatgttaa tatctggacg    120
tacagtacaa ggtgtaggcg caggaggcat atatgtcctc cttgatatcg tgtgctgcga    180
tctggtacca ctccgcgagc gtggaaaata tgtcggccta atgaactcat gggccggtgt    240
tgctgctgga attgggcctg tcataggtgg agccttggcc gatactaact ggcgctggat    300
attctatctc aatcttccga tctgtgggct ggcgttaggc gtggttttgc ttttcatgcg    360
aatgaaaact ggtacgcagg gcgaaggcgt gttgaagctt cgccaaattg attatctggg   420
gagttttatt ttcataccga gtatgatcgc acttctatac ggcttgatca ctggaggcat    480
tcaatatccg tggtcatcgt ggcggattat tctcccattg gtgattggcg ttgccggctg    540
gatactattc cacatccaac agttcttcac ggacgtccca agtgtacccg ttcgcctct     599
```

<210> SEQ ID NO 34
<211> LENGTH: 1465
<212> TYPE: DNA
<213> ORGANISM: Curvularia spicifera

<400> SEQUENCE: 34

```
tcttggtcat ttagaggaag taaaagtcgt aacaaggtct ccgtaggtga acctgcggag    60
ggatcattac acaataaaat acgaaggccg ttcgcggctg gactatttat tacccttgtc    120
ttttgcgcac ttgttgtttc ctgggcgggt tcgctcgcca ccaggaccac aatataaacc   180
tttttatgc agttgcaatc agcgtcagta taacaaatgt aaatcattta caactttcaa    240
caacggatct cttggttctg gcatcgatga agaacgcagc gaaatgcgat acgtagtgtg    300
aattgcagaa ttcagtgaat catcgaatct ttgaacgcac attgcgccct tggtattcc    360
aaagggcatg cctgttcgag cgtcatttgt accctcaagc tttgcttggt gttgggcgtt    420
tttgtctttg gccgccaaa gactcgcctt aaaatgattg gcagccggcc tactggtttc   480
gcagcgcagc acatttttgc gcttgcaatc agcaaaagag gacggcaatc catcaagact   540
```

```
ccttctcacg tttgacctcg gatcaggtag ggatacccgc tgaacttaag catatcaata      600
agcggaggaa aagaaaccaa cagggattgc cctagtaacg gcgagtgaag cggcaacagc      660
tcaaatttga aatctggctc tttcagagtc cgagttgtaa tttgcagagg gcgctttggc      720
tttggcagcg gtccaagttc cttggaacag gacgtcacag agggtgagaa tcccgtacgt      780
ggtcgctagc tattgccgtg taaagcccct tcgacgagtc gagttgtttg ggaatgcagc      840
tctaaatggg aggtaaattt cttctaaagc taaatattgg ccagagaccg atagcgcaca      900
agtagagtga tcgaaagatg aaaagcactt tggaaagaga gtcaaacagc acgtgaaatt      960
gttgaaaggg aagcgcttgc agccagactt gcttgcagtt gctcatccgg gcttttgccc     1020
ggtgcactct tctgcaggca ggccagcatc agtttgggcg gtgggataaa ggtctctgtc     1080
acgtaccttc cttcgggttg gccttatagg ggagacgcca taccaccagc ctggactgag     1140
gtccgcgcat ctgctaggat gctggcgtaa tggctgtaag cggcccgtct tgaaacacgg     1200
accaaggagt ctaacatcta tgcgagtgtt tgggtgtcaa gcccgagcgc gtaatgaaag     1260
tgaacgaggg tgggaacccg caagggtgca ccatcgaccg atcctgaagt ttacggaagg     1320
atttgagtaa gagcatggct gttgggaccc gaaagatggt gaactatgct gaatagggt      1380 gaagccagag gaaactctgg tggaggctcg cagcggttct gacgtgcaaa tcgatcgtca     1440
aatttgggca tagggggcgaa agact                                          1465

<210> SEQ ID NO 35
<211> LENGTH: 1197
<212> TYPE: DNA
<213> ORGANISM: Curvularia spicifera

<400> SEQUENCE: 35
cccatagctt gcttacccat ggcagattgg tatgtgttac ggggcgactg gttgtgatct       60
gggaagggaa tgatactagc gcaaataccc aagatcatag ctgggtgaat ctcacaatgg      120
gtgtaggcgt ggatgcgagg atccggtagt ggcttgaggc ggcggagtcg atccttgcct      180
tcagtagatc gctcagctgc gggcaagccc atcttcattt ctcgccattc ttccaaatcc      240
tcgggagaga atgttatcat tgcagttcct tcttcctcgg catcgaggta ttcaacgaca      300
ccgtcttgaa tgagacctct ccagccgtat gtagcctgct cgacttcctc ttgactccag      360
ccttgtcttg tgctggtctc ttgctgttca gccttgagct tgttgctgat ttccttggta      420
aagatgaggt ggttccggtt tggcttccga atatcgtttt ctacgacgaa caaaggcctc      480 atgcacgac ccgcatctgt gaagatcttg aactctctgt cgcgaatatc acgaatcaaa       540
ctcatctcgt aagacagagt accattgcgg cgaagctcct gcacgactgt gacaagctgc      600
tgagcatttg aatgaacacc aacccagaca ccgttaacga agaccttggt cgcatccggg      660
ttctgattct ggtcgtactc ctcgagaagt tgcatgttac gttgtgtcat gaagtcgata      720
atgggcgatg catcgctacc aacactgaca taacacataa gagacaagtt cttgaccaga      780
ccgcaagcct gtccttcggg cgtctcagca gggcagacaa gaccccaatg agagttgtga      840
agctgtcgcg gctttgccaa cttaccatca cgtccaacgg gggtgttcgt tcgacgcaga      900
tgggacagtg tggaggcata ggtgtatcgg ttcaacacct gcgaaacacc agccttggca      960
gatgcagcct tcttctgatc accccaattg cctgtagcca gagagtactt caggccgttt     1020
gtgatgatgc tggcttttcac agccatttga acgttgaagt cttggttgtt ttccacgcac     1080
cgctggaggt acttgtagac atccttggtg agcttcagga acaagattcg gaacaagttg     1140
gcaatcagag gtccagccag atctagtcgc ttctttccaa agtgatcacg atcgtcc         1197
```

<210> SEQ ID NO 36
<211> LENGTH: 1197
<212> TYPE: DNA
<213> ORGANISM: Curvularia spicifera

<400> SEQUENCE: 36

| | | | | | |
|---|---|---|---|---|---|
| cccatagctt | gcttacccat | ggcagattgg | tatgtgttac | ggggcgactg | gttgtgatct | 60 |
| gggaagggaa | tgatactagc | gcaaataccc | aagatcatag | ctgggtgaat | ctcacaatgg | 120 |
| gtgtaggcgt | ggatgcgagg | atccggtagt | ggcttgaggc | ggcggagtcg | atccttgcct | 180 |
| tcagtagatc | gctcagctgc | gggcaagccc | atcttcattt | ctcgccattc | ttccaaatcc | 240 |
| tcgggagaga | atgttatcat | tgcagtttct | tcttcctcgg | catcgaggta | ttcaacgaca | 300 |
| ccgtcttgaa | tgagacctct | ccagccgtat | gtagcctgct | cgacttcctc | ttgactccag | 360 |
| ccttgtcttg | tgctggtctc | ttgctgttca | gccttgagct | tgttgctgat | tccttggta | 420 |
| aagatgaggt | ggttccggtt | tggcttccga | atatcgtttt | ctacgacgaa | caaaggcctc | 480 |
| atgacacgac | ccgcatctgt | gaagatcttg | aactctctgt | cgcgaatatc | acgaatcaaa | 540 |
| ctcatctcgt | aagacagagt | accattgcgc | gaagctcct | gcacgactgt | gacaagctgc | 600 |
| tgagcatttg | aatgaacacc | aacccagaca | ccgttaacga | agaccttggt | cgcatccggg | 660 |
| ttctgattct | ggtcgtactc | ctcgagaagt | tgcatgttac | gttgtgtcat | gaagtcgata | 720 |
| atgggcgatg | catcgctacc | aacactgaca | taacacataa | gagacaagtt | cttgaccaga | 780 |
| ccgcaagcct | gtccttcggg | cgtctcagca | gggcagacaa | gaccccaatg | agagttgtga | 840 |
| agctgtcgcg | gctttgccaa | cttaccatca | cgtccaacgg | gggtgttcgt | tcgacgcaga | 900 |
| tgggacagtg | tggaggcata | ggtgtatcgg | ttcaacacct | gcgaaacacc | agccttggca | 960 |
| gatgcagcct | tcttctgatc | accccaattg | cctgtagcca | gagagtactt | caggccgttt | 1020 |
| gtgatgatgc | tggcttttcac | agccatttga | acgttgaagt | cttggttgtt | ttccacgcac | 1080 |
| cgctggaggt | acttgtagac | atccttggtg | agcttcagga | acaagattcg | gaacaagttg | 1140 |
| gcaatcagag | gtccagccag | atctagtcgc | ttctttccaa | agtgatcacg | atcgtcc | 1197 |

<210> SEQ ID NO 37
<211> LENGTH: 387
<212> TYPE: DNA
<213> ORGANISM: Curvularia spicifera

<400> SEQUENCE: 37

| | | | | | |
|---|---|---|---|---|---|
| cccgactggc | cgaagacgaa | gttgtcgggg | cggaagagct | gaccaaaggg | accagcgcgg | 60 |
| acagcgtcca | tggtaccggg | ctcgagatcg | acgaggacgg | cacggggcac | gaacttgttg | 120 |
| ttggaagcct | gctgcacatc | agtattggtc | ttttgtctgt | tggggcttca | ccagggacg | 180 |
| tacttcgttg | aagtagacgt | tcatgcgctc | gagctgaagg | tcagaggtgc | cgttgtagac | 240 |
| accagagccg | tcgaggccat | gctcgccgga | aatggtctgc | cagaaggcgg | caccaatttg | 300 |
| gttaccctgt | agcggctgtt | agcagtcgtt | cccgtggtgt | tttcaggcgg | cgcgagactt | 360 |
| acgcattgac | cggtctggag | gtgaacc | | | | 387 |

<210> SEQ ID NO 38
<211> LENGTH: 622
<212> TYPE: DNA
<213> ORGANISM: Curvularia spicifera

<400> SEQUENCE: 38

```
aaatgttgtt catgcgacca atggatttgc aagtcatctt gtacccggcc tccgcaagaa        60
gatcgtaggc gcacgagcgc acatgtcggc tcagcgacca ggggaactat tccctaacag       120
tggtggcatg cgctcatgga gtgtgattta tggtggggag tttgactatg tcacccaacg       180
gccttccgcg gacggtgata tccaaggaga tatcatgctt ggaggcggct ttatgcggtc       240
gctaaagaag ggcgtcgacc aaattggact ttatgacgac ggtgatattc ttgagcctct       300
gaccatttcg catatctcag gcgtgtttcc tgcagttttc catcccagat ggggtgctgg       360 tggcggggttg aaacaagtgt ggtctggaat tctgggattg actggtgatt tacttcctct       420
ggtgggccgg ctggatacaa aattgacagg tcgaaattct ccgagtcagc acggcgtagt       480
ggatgcaaag agcagttgtg gagagtgggt tgcagccggc ttctgcgggg aaggcatggt       540
ctgggcctgg ctttgtggag ttgctcttgg aattatggtc gctggaactg aggaacacga       600
tgtaacgaaa gctcctggga ga                                                622

<210> SEQ ID NO 39
<211> LENGTH: 1451
<212> TYPE: DNA
<213> ORGANISM: Aspergillus ruber

<400> SEQUENCE: 39
tcttggtcat ttagaggaag taaaagtcgt aacaaggttt ccgtaggtga acctgcggaa        60
ggatcattac cgagtgcggg ccctctgggt ccaacctccc atccgtgtct atctgtaccc       120
tgttgcttcg gcgtggccac ggcccgccgg agactaacat ttgaacgctg tctgaagttt       180
gcagtctgag ttttttagtta aacaatcgtt aaaactttca acaacggatc tcttggttcc       240
ggcatcgatg aagaacgcag cgaaatgcga taattaatgt gaattgcaga attcagtgaa       300
tcatcgagtc tttgaacgca cattgcgccc cctggtattc cgggggggcat gcctgtccga       360 gcgtcattgc tgcccttcaag cacggcttgt gtgttgggct tccgtccctg caacggggga       420
cgggcccaaa aggcagtggc ggcaccatgt ctggtcctcg agcgtatggg gctttgtcac       480
ccgctcccgt aggtccagct ggcagctagc ctcgcaacca atcttttttaa ccaggttgac       540 ctcggatcag gtagggatac ccgctgaact taagcatatc aataagcgga ggaaaagaaa       600
ccaaccggga ttgcctcagt aacggcgagt gaagcggcaa gagctcaaat ttgaaatctg       660 gccccctccgg ggtccgagtt gtaatttgta gaggatgctt cgggtgcggc cccgtctaa       720 gtgctctgga acgggccatc ggagagggtg agaatcccgt ctgggacggg gtgtccgcgt       780
ccatgtgaag ctccttcgac gagtcgagtt gttggggaat gcagctctaa atgggtggta       840
aatttcatct aaagctaaat actggccgga gaccgatagc gcacaagtag agtgatcgaa       900
agatgaaaag cactttgaaa agagagttaa acagcacgtg aaattgttga agggaagcg       960 cttgcgacca gactcgcttc cggggttcag ccggctttcg ggccggtgta cttccccggg      1020 ggcggggccag cgtcggtttg ggcggccggt caaaggcccc tggaatgtaa cgcctctcgg      1080
ggcgccttat agccaggggt gtcatgcggc cagcctggac cgaggaacgc gcttcggcac      1140
ggacgctggc ataatggtcg taaacgaccc gtcttgaaac acggaccaag gagtctaaca      1200
tctacgcgag tgttcgggtg tcaaacccgt gcgcgcagtg aaagcgaacg gaggtgggag      1260 cccccctcgcg gggcgcacca tcgaccgatc ctgatgtctt cggatggatt tgagtaagag      1320
cgtagctgtg gggacccgaa agatggtgaa ctatgcctga ataggcgaa gccagaggaa      1380 actctggtgg aggctcgcag cggttctgac gtgcaaatcg atcgtcaaat ttgggtatag      1440
gggcgaaaga c                                                            1451
```

<210> SEQ ID NO 40
<211> LENGTH: 1440
<212> TYPE: DNA
<213> ORGANISM: Coniochaeta prunicola

<400> SEQUENCE: 40

```
tcttggtcat ttagaggaag taaaagtcgt aacaaggtct ccgttggtga accagcggag      60
ggatcattac aagaagccga aaggctactt caaaccatcg tgaacttatc caagttgctt     120
cggcggcgcg gctcccctcg cggggtgccg cagccccgcc ccctcggggg tggtgggcgc     180
ccgccggagg tattaaactc tcccgtatta tagtggtatt tctgagtaaa acaaataag      240
ttaaaacttt caacaacgga tctcttggtt ctggcatcga tgaagaacgc agcgaaatgc     300
gataagtaat gtgaattgca gaattcagtg aatcatcgaa tctttgaacg cacattgcgc     360
ccgctagtat tctagcgggc atgcctgttc gagcgtcatt tcaaccctca agccctgctt     420
ggtgttgggg ccctacggct gccgtaggcc ctgaaaagaa gtggcgggct cgctgcaact     480
ccgagcgtag taattcatta tctcgctagg gaggcgcggc ggtgctcctg ccgttaaaga     540
ccatctttaa ccaaaggttg acctcggatc aggtaggaat accgctgaa cttaagcata     600
tcaataagcg gaggaaaaga accaacagg gattgcccta gtaacggcga gtgaagcggc     660
aacagctcaa atttgaaatc tggcttcggc ccgagttgta atttgtagag gatgcttttg     720
gtgaggtgcc ttctgagttc cctggaacgg gacgccagag agggtgagag ccccgtatag     780
tcggccaccg atcctctgta aagctccttc gacgagtcga gtagtttggg aatgctgctc     840
aaaatgggag gtatatctct tctaaagcta aatataggcc agagaccgat agcgcacaag     900
tagagtgatc gaaagatgaa aagcactttg aaaagagggt taaatagcac gtgaaattgt     960
tgaaagggaa gcgcttgtga ccagacttgc gccgggctga tcatccagtg ttctcactgg    1020
tgcactcgac ccggctcagg ccagcgtcgg ttctcgcagg gggataaaag cttcgggaac    1080
gtggcacctt cgggtgtgtt atagcccgct gcttaatacc ccggtgggga ccgaggttcg    1140
cgctctgcaa ggacgctggc ataatggtca tcagcgaccc gtcttgaaac acggaccaag    1200
gagtcgaggt tttgcgcgag tgtttgggtg taaaacccgc acgcgtaatg aaagtgaacg    1260
taggtgagag cttcggcgca tcatcgaccg atcctgatgt attcggatgg atttgagtaa    1320
gagcgtatag cctcggaccc gaaagatggt gaactatgcc tgaatagggg gaagccagag    1380
gaaactctgg tggaggctcg cagcggttct gacgtgcaaa tcgatcgtca aatttgggca    1440
```

<210> SEQ ID NO 41
<211> LENGTH: 922
<212> TYPE: DNA
<213> ORGANISM: Coniochaeta prunicola

<400> SEQUENCE: 41

```
tcctgaggga aacttcggcg gtaaccagct actagatggt tcgattagtc tttcgccccc      60
atgcccaaat ttgacgatcg atttgcacgt cagaaccgct gcgagcctcc accagagttt     120
cctctggctt caccctattc aggcatagtt caccatcttt cgggtccgag gctatacgct     180
cttactcaaa tccatccgaa tacatcagga tcggtcgatg atgcgccgaa gctctcacct     240
acgttcactt tcattacgcg tgcgggtttt acacccaaac actcgcgcaa acctcgact      300
ccttggtccg tgtttcaaga cgggtcgctg atgaccatta tgccagcgtc cttgcagagc     360
gcgaacctcg gtccccacag gggtattaag cagcgggcta taacacaccc gaaggtgcca     420
```

| | |
|---|---:|
| cgttcccgaa gcttttatcc ccctgcgaga accgacgctg gcctgagccg ggtcgagtgc | 480 |
| accagtgaga acactggatg atcagcccgg cgcaagtctg gtcacaagcg cttcccttc | 540 |
| aacaatttca cgtgctattt aaccctcttt tcaaagtgct tttcatcttt cgatcactct | 600 |
| acttgtgcgc tatcggtctc tggcctatat ttagctttag aagagatata cctcccattt | 660 |
| tgagcagcat tcccaaacta ctcgactcgt cgaaggagct ttacagagga tcggtggccg | 720 |
| actatacggg gctctcaccc tctctggcgt cccgttccag ggaactcaga aggcacctca | 780 |
| ccaaaagcat cctctacaaa ttacaactcg ggccgaagcc agatttcaaa tttgagctgt | 840 |
| tgccgcttca ctcgccgtta ctagggcaat ccctgttggt ttcttttcct ccgcttattg | 900 |
| atatgcttaa gttcagcggg ta | 922 |

<210> SEQ ID NO 42
<211> LENGTH: 1151
<212> TYPE: DNA
<213> ORGANISM: Coniochaeta prunicola

<400> SEQUENCE: 42

| | |
|---|---:|
| cttccgtcaa tttctttaag tttcagcctt gcgaccatac tcccccaga acccagaaac | 60 |
| tttactttcg tgtaaggtgc cgaacgagtc aaaatataac atcgtccgat ccctagtcgg | 120 |
| catagtttat ggttaagact acgacggtat ctgatcgtct tcgatcccct aactttcgtt | 180 |
| cctgattaat gaaaacatcc ttggcaaatg ctttcgcagt agttagtctt caataaatcc | 240 |
| aagaatttca cctctgacaa ttgaatactg atgcccccga ctgtccctat taatcattac | 300 |
| ggcggtccta gaaaccaaca aaatagaacc acacgtccta ttctattatt ccatgctaat | 360 |
| gtattcgagc ataggccttc tttaagcgat ctaatttgtt caaagtaaaa gtcctggttc | 420 |
| cccgacacac ccagtgaagg gcatgcggtt ccccagaggg aaaggcccgg ccggaccagt | 480 |
| gcacgcggtg aggcggaccg gccagccagg cccaaggttc aactacgagc ttttaactg | 540 |
| caacaacttt aatatacgct attggagctg gaattaccgc ggctgctggc accagacttg | 600 |
| ccctccaatt gttcctcgtt aagggattta aattgtactc attccaatta caagacccaa | 660 |
| aagagccctg tatcagtatt tattgtcact acctccccga atcgggattg gtaatttgc | 720 |
| gcgcctgctg ccttccttgg atgtagtagc cgtttctcag gctccttctc cggggtcgag | 780 |
| ccctaaccct ccgttacccg ttgtcaccat ggctggccaa gacccagccg tcgaaagttg | 840 |
| ataggggcaga atttgaatg aaccatcgcc ggcgcaaggc cgtgcgattc gagaagttat | 900 |
| tatgaatcac cagagagccc cgaagggcat tggttttaa tctaataaat acatcccttc | 960 |
| cgaagtcggg atttttagca tgtattagct ctagaattac cacggttatc caagtagtaa | 1020 |
| ggtactatca aataaacgat aactgattta atgagccatt cgcagtttcg cggtataatt | 1080 |
| gcttatactt agacatgcat ggcttaatct ttgagacaag catatgacta ctggcagaat | 1140 |
| caaccaggta a | 1151 |

<210> SEQ ID NO 43
<211> LENGTH: 604
<212> TYPE: DNA
<213> ORGANISM: Coniochaeta prunicola

<400> SEQUENCE: 43

| | |
|---|---:|
| tgctggtagt gcgaatgaaa atggctggtt ccaggatata acgggtaatc gactgcactt | 60 |
| taacaaggct atgcgagtac tttgcgacca tggtcttgca gaagcagatc cgccgacgaa | 120 |
| agagcacggt tcggagtctg gagggtacag tgtgcacgga tgtgtgcact cctggatggt | 180 |

```
aaacgtcctc aaccagacag gagatgcgga gatggcacgt ctggctttga ggtgtgtggc    240
tagccatgtg ccaagcacgg aggagggtga gtattggcgg gtacagcggc gcctccttct    300
gcacgcagac caatgcttga aattgatgga agagggtcag gaggaggaag gcaatggatg    360
ggtattccat aatctaggag atctctacaa agcccaaggg cggttcaagg aagcagaagc    420
catgtacgag cgggcgcttc gaggcaagga gaaggcatgg ggaccagacc acacgtcgac    480
actcgacaca gtcaacaatc tgggtctcgt cgccgacaac aaagccagcc acaccaaaca    540
tcaagttcca ttctcgttcc ccgtctttgt cgtgtggcag acaaaacctg atggaacccg    600
aaag                                                                 604

<210> SEQ ID NO 44
<211> LENGTH: 1486
<212> TYPE: DNA
<213> ORGANISM: Pestalotiopsis neglecta

<400> SEQUENCE: 44
tggtcattta gaggaagtaa aagtcgtaac aaggtctccg ttggtgaacc agcggaggga     60
tcattataga gttttctaaa ctcccaaccc atgtgaactt accattgttg cctcggcaga    120
agctacctgg ttaccttacc ttggaacggc ctaccctgta gcgccttacc ctggaacggc    180
ctaccctgta acgctgccg gtggactacc aaactcttgt tattatattg taatctgagc     240
gtcttatttt aataagtcaa aactttcaac aacggatctc ttggttctgg catcgatgaa    300
gaacgcagcg aaatgcgata agtaatgtga attgcagaat tcagtgaatc atcgaatctt    360
tgaacgcaca ttgcgcccat tagtattcta gtgggcatgc ctgttcgagc gtcatttcaa    420
cccttaagcc tagcttagtg ttgggagcct actgcttttg ctagcggtag ctcctgaaat    480
acaacggcgg atctgcgata tcctctgagc gtagtaattt ttatctcgct tttgactgga    540
gttgcagcgt ctttagccgc taaaccccc aattttttaat ggttgacctc ggatcaggta    600 ggaataccg ctgaacttaa gcatatcaat aagcggagga aaagaaacca acagggattg     660
ccttagtaac ggcgagtgaa gcggcaacag ctcaaatttg aaatctggcc ctcgggtccg    720
aattgtaatt tgtagaggat gattttggtg cggtatcttc cgagttcctt ggaacaggac    780
gccttagagg gtgagagccc cgtacggttg aatgcctagc ctctgtaaat ctccttcgac    840
gagtcgagta gtttgggaat gctgctctaa atgggaggta aatttcttct aaagctaaat    900
attggccaga gaccgatagc gcacaagtag agtgatcgaa agatgaaaag cactttgaaa    960
agagggttaa atagcacgtg aaattgttga aaggaaggga tttgtgacca gacttttttct   1020 gggcggatca tccggggttc tctccggtgc actttgccca gtaaaggcca gcatcgattt   1080
tcggcggcgg ataaaagcag tgggaatgtg gctccctacg gggagtgtta tagcccattg   1140
tataatacgc tgctggggat cgaggtacgc gcttctgcaa ggatgctggc gtaatggtta   1200
tcaatcaccc gtcttgaaac acggaccaag gagtcgaaca tttatgcgag tgtttgggtg   1260
ttaaaccctc acgcgtaatg aaagtgaacg gaggtgagag cccgtacggg tgcatcatcg   1320
accgatcctg aagttttcgg atggatttga gtaagagcat aactgttcgg acccgaaaga   1380
tggtgaacta tgcgtggata gggtgaagcc agaggaaact ctggtggagg ctcgcagcgg   1440
ttctgacgtg caaatcgatc gtcaaatctg cgcatgggggg cgaaag                 1486

<210> SEQ ID NO 45
<211> LENGTH: 610
<212> TYPE: DNA
```

<213> ORGANISM: Pestalotiopsis neglecta

<400> SEQUENCE: 45

| | | |
|---|---|---|
| ccagtttcct gtccaccaag gtggcagtcg acgcattcac agaatgcttc actggcgcat | 60 |
| cctgcacgac cccagcgacg agcgccgcgc cctcggcaac ttctactgcc tcgacgtcgt | 120 |
| caggagcaag cacctctagc gcggcagcat cggggtccag ctcggggtcc agcggcctct | 180 |
| ccacgggcgc catcgtcggc atcgccgtcg cctgcggcgt cgtgggcctg gccctgatcg | 240 |
| gcgccgccgt ctggttcctg tgcttccgcc gccggcgccg ccacggcgac cactcggccc | 300 |
| tggcgcagca gcagcagtta caaaacggca gctacaacat gtcggacggc gggctgcccc | 360 |
| acaaggccgg catgatgatg acgcgcagcg acaaggacct gccacacgtc gccaccgaca | 420 |
| gcccgcagtc ggcgtacgcc ccgagccgcg tgctgcgcga tcgatgggc agcggggccg | 480 |
| tcggggccgg cctgatgagc gggaacggca acgaccacgt ccacgtccac caccaccacc | 540 |
| accagcacgc cagcgtcgac atggaccacg gcggcgagag cgaaaacgac aacaacaaca | 600 |
| acaacgccta | 610 |

<210> SEQ ID NO 46
<211> LENGTH: 461
<212> TYPE: DNA
<213> ORGANISM: Pestalotiopsis neglecta

<400> SEQUENCE: 46

| | | |
|---|---|---|
| cttcagctgg aacttgatgg tggacttgac ctcgttgatc ctgccagtaa ggtcgtcgga | 60 |
| gtgggagaca ggggtaggga acttgccggc tgtgaggttc aagttagta caagtcaaga | 120 |
| ggatcagaac tgaaagtgtc gcgacttacc cttggacaga ccaggaccca agagacgggg | 180 |
| gatctgcttg atcagagagt ccgaagcgac gaaagcatcg tacttgcgag cgagcttctt | 240 |
| gatcagcttc ttgttcttgt tcagcttctt caggtcatcg gcgctcatct aggtcgcgta | 300 |
| ttagctcggc tgacatgccc attgaaaact gtgtatctta cggcgtcgac accaccgtgc | 360 |
| ttggcacggt cgagatcgtg ctggtcacca agaatgcaga tggccatgtt ggggcggggg | 420 |
| atggtcggca ggcggacggt acccgagaaa cgcttgtcac g | 461 |

<210> SEQ ID NO 47
<211> LENGTH: 1227
<212> TYPE: DNA
<213> ORGANISM: Pestalotiopsis neglecta

<400> SEQUENCE: 47

| | | |
|---|---|---|
| cccatggctt gtttacccat ggccgactgg taagtgttac gaggagactg tagattgggt | 60 |
| cagttttgaa ttcacagcg cgggattcct tgtgaactta cctggttgtg atctgggaac | 120 |
| ggaatgatgc ttgcgcaaat acccagcagc atgctcggat ggatctcgca atgggtgtac | 180 |
| atgtgcgtgg tagggttgag cttttgtcttc aatctggcat tgagatcctc gcccacatcc | 240 |
| tggctgacat cgatgccctg cttggctagt cgataagttt ccaaatcttc aggcgtcatg | 300 |
| cagatcatgg cggtctcttc ttcttcggca tcaaggtatt caatgactcc ctcgttgaca | 360 |
| agaccttgcc agccgaaaaa gtcctcgctg ccggggggaa gcgtagcgtc tcgttccaga | 420 |
| cgtcggatca tgtccttgtt gagaaccaaa ttgccagctt cgacaccgcg gtcggggtcg | 480 |
| tcctcctgtt ccacaacgaa cagcgggcgc atgacacgcc ctgcgtcgga gaaaatcttg | 540 |
| aactcgcggt cgcgaatgtc gcggaccagg gaaacctcgg caggaatttg gttactacgc | 600 |
| cggagctgct gaacatccct aactagagcc ttggggtcct ggtgaacacc aatccaggat | 660 |

```
ccgttgagga agatcttggt agcgttggga taacgcacgg catcatactc ttcgagtact      720
tccatgtttc tagtaatcat gtagtcgatg ataggttccg tgctagtacc cacactcaca      780
gagcacatga gggacagatt cttgacaaga ccacaggcct gaccttctgg cgtctctgca      840
ggacacacca agccccaatg cgtgttgtgc agctggcgag gctttgcaag ttttccgtca      900
cgtccaatgg gcgtgtttgt tcgtcgcaaa tgggatagtg tagatgcaaa ggtatatctg      960
ttcaagacct gcgagacacc agctgtcgag ctcatggcct tcttctggtc gccccagttt     1020
ccagtggcga gagagtactt cagaccgttc gtgacaatac cagacttgat accgaactgg     1080
acctggaagt ccttgttctg ctcaacacaa cgtttgagag tcatcgtgat ctcgttggtg     1140
agcttccgaa caatgttgcg gaagagcttg gcaagtaggg ggccggccag atccagacgc     1200
ttcttgccaa agtgatcacg atcgtcc                                         1227

<210> SEQ ID NO 48
<211> LENGTH: 530
<212> TYPE: DNA
<213> ORGANISM: Pestalotiopsis neglecta

<400> SEQUENCE: 48
gttcacctcc agaccggtca atgcgtaagt acatgccaaa tcccgcgata gcgtgcccaa       60
aacaccagag ctcacattca ccaacagggt aaccaaattg gtgctgcctt ttggtatgta      120
gcccatctac ctcgacacgc tcaatacga caacccccg caactcgaca cgacgttct       180
caacaagtgc ttgcttggaa acaagggaaa gacttgatac tgaccggtcc ctgataggca      240
aaccatctct ggcgagcacg gtctcgacag caatggagtg tacgtaccct tccttggct      300
acttgctttc ccacgaacat ctcagctaac actcgtggtt gttcagctac aacggtacct      360
ccgagctcca gctcgagcgc atgagcgtct acttcaacga ggcttccggc aacaagtacg      420
ttcctcgtgc cgtcctcgtc gatctcgagc ccggtaccat ggatgccgtc cgcgccggtc      480
cttcggtca gctcttccgc cctgacaact tcgtcttcgg tcagtccggt       530

<210> SEQ ID NO 49
<211> LENGTH: 907
<212> TYPE: DNA
<213> ORGANISM: Enterobacter cowanii

<400> SEQUENCE: 49
tcgcgttcgt taacaaaatg daccgcatgg gcgctaactt cctgaaagtt gttgatcaga       60
tcaaacccg tctgggcgcg aacccggttc cgctgcagct ggcaattggc gctgaagaag      120
gtttcaccgg tgttgttgac ctggtgaaaa tgaaagcgat caactggaac gatgctgacc      180
agggcgttac cttcgtttac gaagatatcc cggctgagat gcaggacctg gctgacgaat      240
ggcaccagaa cctgatcgaa tctgcggcgg aagcttcaga agagctgatg gagaaatacc      300
tgggtggtga agacctgact gaagaagaga tcaaaactgc tcttcgtcag cgtgttctga      360
caacgaaat catcctggta acctgtggtt ctgcgtttaa gaacaaaggc gttcaggcga      420
tgctggatgc ggtaattgat tacctgccgt ccccgactga cgttccggcg atcaacggta      480
tgctggacga tggtaaagat accccggccg agcgtcacgc aagcgacgaa gagccgttct      540
ctgcactggc gttcaaaatc gcaactgacc cgttcgtagg taacctgacc ttcttccgcg      600
tgtactccgg tgtggttaac tctggtgata ccgtactgaa ctccgtgaaa tctgcacgtg      660
agcgtttcgg tcgtatcgtt cagatgcacg ctaacaaacg tgaagagatc aagaagttc      720
```

```
gcgcgggcga tatcgctgca gcgatcggtc tgaaagacgt gatcaccggt gacaccctgt    780
gtgatccgga caacccgatc attctggagc gtatggaatt cccggagccg gtaatctcca    840
tcgctgtaga accgaaaacc aaagctgacc aggaaaaaat gggtctggct ctgggccgtc    900
tggctaa                                                              907
```

<210> SEQ ID NO 50
<211> LENGTH: 1465
<212> TYPE: DNA
<213> ORGANISM: Enterobacter cowanii

<400> SEQUENCE: 50

```
tgctcagatt tgaacgctgg cggcaggcct aacacatgca agtcgaacgg taacaggaag     60
cagcttgctg cttcgctgac gagtggcgga cgggtgagta atgtctggga aactgcctga    120
tggaggggga taactactgg aaacggtagc taataccgca taacgtcgca agaccaaaga    180
gggggacctt cgggcctctt gccatcagat gtgcccagat gggattagct agtaggtggg    240
gtaacggctc acctaggcga cgatccctag ctggtctgag aggatgacca gccacactgg    300
aactgagaca cggtccagac tcctacggga ggcagcagtg gggaatattg cacaatgggc    360
gcaagcctga tgcagccatg ccgcgtgtat gaagaaggcc ttcgggttgt aaagtacttt    420
cagcggggag gaaggcgatg tggttaataa ccgcgtcgat tgacgttacc cgcagaagaa    480
gcaccggcta actccgtgcc agcagccgcg gtaatacgga gggtgcaagc gttaatcgga    540
attactgggc gtaaagcgca cgcaggcggt ctgtcaagtc ggatgtgaaa tccccgggct    600
caacctggga actgcatccg aaactggcag gcttgagtct cgtagagggg ggtagaattc    660
caggtgtagc ggtgaaatgc gtagagatct ggaggaatac cggtggcgaa ggcggccccc    720
tggacgaaga ctgacgctca ggtgcgaaag cgtggggagc aaacaggatt agataccctg    780
gtagtccacg ccgtaaacga tgtcgacttg gaggttgtgc ccttgaggcg tggcttccgg    840
agctaacgcg ttaagtcgac cgcctgggga gtacggccgc aaggttaaaa ctcaaatgaa    900
ttgacggggg cccgcacaag cggtggagca tgtggtttaa ttcgatgcaa cgcgaagaac    960
cttacctggt cttgacatcc acagaacttt ccagagatgg attggtgcct tcgggaactg   1020
tgagacaggt gctgcatggc tgtcgtcagc tcgtgttgtg aaatgttggg ttaagtcccg   1080
caacgagcgc aacccttatc ctttgttgcc agcggtccgg ccgggaactc aaaggagact   1140
gccagtgata aactggagga aggtggggat gacgtcaagt catcatggcc cttacgacca   1200
gggctacaca cgtgctacaa tggcgcatac aaagagaagc aaactcgcga gagccagcgg   1260
acctcataaa gtgcgtcgta gtccggattg gagtctgcaa ctcgactcca tgaagtcgga   1320
atcgctagta atcgtgaatc agaatgtcac ggtgaatacg ttcccgggcc ttgtacacac   1380
cgcccgtcac accatgggag tgggttgcaa agaagtaggt agcttaacct tcggggaggg   1440
cgcttaccac tttgtgatca tgact                                         1465
```

<210> SEQ ID NO 51
<211> LENGTH: 591
<212> TYPE: DNA
<213> ORGANISM: Enterobacter cowanii

<400> SEQUENCE: 51

```
acgatctcgg cgggtaataa ccctgcaccg cgatgcaggc acgtagtgcg atctgcggtg     60
acagcgtgtt gatgggcgtg gctgcgccag tgttgttcac cgtcgcagtt gcgccagcca    120
tactcattgt cacaccggcc agcgggacct gtgtgccgcc cgcaggcgca taaatacttg    180
```

-continued

```
ttcccgggtt ttgtgttgcc gccagtcggt tgttagttgc tgacggggta ttggatacac    240
ccggagcagt tgtcgcactg atagaaaacg cgccagttcc gagcatcgcc tggtgagaat    300
ggaccggcat ctgagagatg ctcattacag ccgtttccgc accgcgcgtc tgccccagcg    360
atagcacatt gttattgggc ccaacaccgg ctccgaccgg gcttctgcct cgcatatccg    420
gcagattaaa ggaggtattc gccgtcgatg aagggtata aaggcgggta attagggaat    480
acaacgcctg ggattgttgt actggaatcg tctgaccgtt cgcttccagg tagccgcgcg    540
gacaaaagct tgctgctgta aagcaaaccg cgccaacata gggctccgaa c             591
```